US010195289B2

(12) United States Patent
Farias et al.

(10) Patent No.: US 10,195,289 B2
(45) Date of Patent: Feb. 5, 2019

(54) ENGINEERED POLYPEPTIDE CONJUGATES USING TRANSGLUTAMINASE

(71) Applicant: RINAT NEUROSCIENCE CORP., South San Francisco, CA (US)

(72) Inventors: Santiago Esteban Farias, San Francisco, CA (US); Meritxell Galindo Casas, Mountain View, CA (US); Pavel Strop, San Mateo, CA (US)

(73) Assignee: RINAT NEUROSCIENCE CORP., South San Francisco, CA (US)

( * ) Notice: Subject to any disclaimer, the term of this patent is extended or adjusted under 35 U.S.C. 154(b) by 16 days.

(21) Appl. No.: 14/908,492

(22) PCT Filed: Jul. 30, 2014

(86) PCT No.: PCT/IB2014/063566
§ 371 (c)(1),
(2) Date: Jan. 28, 2016

(87) PCT Pub. No.: WO2015/015448
PCT Pub. Date: Feb. 5, 2015

(65) Prior Publication Data
US 2016/0193356 A1   Jul. 7, 2016

Related U.S. Application Data

(60) Provisional application No. 61/860,757, filed on Jul. 31, 2013, provisional application No. 62/028,236, filed on Jul. 23, 2014.

(51) Int. Cl.
*A61K 47/68* (2017.01)

(52) U.S. Cl.
CPC .......... *A61K 47/6803* (2017.08); *A61K 47/68* (2017.08); *A61K 47/6805* (2017.08); *A61K 47/6809* (2017.08); *A61K 47/6817* (2017.08)

(58) Field of Classification Search
None
See application file for complete search history.

(56) References Cited

U.S. PATENT DOCUMENTS

| | | | |
|---|---|---|---|
| 6,919,076 | B1 | 7/2005 | Green et al. |
| 7,208,171 | B2 | 4/2007 | Messersmith et al. |
| 7,375,078 | B2 | 5/2008 | Feng |
| 7,521,541 | B2 | 4/2009 | Eigenbrot et al. |
| 8,871,908 | B2 | 10/2014 | Liu et al. |
| 2004/0266690 | A1 | 12/2004 | Pool |
| 2006/0019258 | A1 | 1/2006 | Yeakley |
| 2007/0184537 | A1 | 8/2007 | Schibli et al. |
| 2008/0279868 | A1 | 11/2008 | Boyd et al. |
| 2010/0278750 | A1 | 11/2010 | Krippner et al. |
| 2011/0184147 | A1 | 7/2011 | Kamiya et al. |

FOREIGN PATENT DOCUMENTS

| | | |
|---|---|---|
| EP | 0725145 A1 | 8/1996 |
| WO | 0043492 A2 | 7/2000 |
| WO | 2009059278 A1 | 5/2009 |
| WO | 2010002042 A1 | 1/2010 |
| WO | 2010011096 A2 | 1/2010 |
| WO | 2010045270 A2 | 4/2010 |
| WO | 2010080124 A2 | 7/2010 |
| WO | 2011069164 A2 | 6/2011 |
| WO | 2011090305 A2 | 7/2011 |
| WO | 2011090306 A2 | 7/2011 |
| WO | 2011122922 A2 | 10/2011 |
| WO | 2012059882 A2 | 5/2012 |
| WO | 2013068946 A2 | 5/2013 |
| WO | 2013092998 A1 | 6/2013 |

OTHER PUBLICATIONS

Colman et al., Research in Immunology (145(1):33-36, 1994.*
Lederman et al., Molecular Immunology 28:1171-1181, 1991.*
Stancovski et al., PNAS, 88: 8691-8695, 1991.*
Strop et al., Chemistry & Biology 20: 161-167, Feb. 21, 2013.*
Dosio, F., et al., "Immunotoxins and Anticancer Drug Conjugate Assemblies: The Role of the Linkage between Components," 2011, Toxins, 848-883, vol. 3.
Plagmann, I., et al., "Transglutaminase-catalyzed covalent multimerization of camelidae anti-human TNF single domain antibodies improves neutralizing activity," 2009, Journal of Biotechnology, 170-178, vol. 142.
Yu, L., et al., "Interaction between Bevacizumab and Murine VEGF-A: A Reassessment," 2008, Investigative Ophthalmology & Visual Science, 522-527, vol. 49, No. 2.
Carter, P., "Bispecitic human IgG by design," Journal of Immunological Methods, 2001, 7-15, vol. 248.
International Search Report for Appln. No. PCT/IB2014/063566 completed Jan. 29, 2015.
Written Opinion of the International Searching Authority for Appln. No. PCT/IB2014/063566 completed on Jan. 29, 2015.
Doronina, S., et al., "Novel Peptide Linkers for Highly Potent Antibody—Auristatin Conjugate," Bioconjugate Chemistry, 2008, 1960-1963, vol. 19, No. 10.
Farias, S., et al., "Mass Spectrometric Characterization of Transglutaminase Based Site-Specific Antibody-Drug Conjugates," Bioconjugate Chemistry, 2014, 240-250, vol. 25, No. 2.
Fontana, A., et al., "Site-specific modification and PEGylation of pharmaceutical proteins mediated by transglutaminase," Advanced Drug Delivery Reviews, 2008, 13-28, vol. 60.

(Continued)

*Primary Examiner* — Phuong Huynh
(74) *Attorney, Agent, or Firm* — Jenny J. Yeh

(57) ABSTRACT

The present invention provides engineered polypeptide conjugates (e.g., antibody-drug-conjugates) comprising specific acyl donor glutamine-containing tags and amine donor agents. The invention also provides methods of making such engineered polypeptide conjugates using transglutaminase and methods of using thereof.

17 Claims, 14 Drawing Sheets
Specification includes a Sequence Listing.

(56) References Cited

OTHER PUBLICATIONS

Gentle, I., et al., "Direct Production of Proteins with N-Terminal Cysteine for Site-Specific Conjugation," Bioconjugate Chemistry, 2004, 658-663, vol. 15, No. 3.

Gomez, N., et al., "Triple Light Chain Antibodies: Factors That Influence Its Formation in Cell Culture," Biotechnology and Bioengineering, 2010, 748-760, vol. 105, No. 4.

Jeger, S., "Site-Specific Conjugation of Tumour-Targeting Antibodies Using Transglutaminase," A Dissertation Submitted to ETH Zurich for the Degree of Doctor of Sciences, DISS. ETH 18696, 2009, 51-85.

Jeger, S., et al., "Site-Specific and Stoichiometric Modification of Antibodies by Bacterial Transglutaminase," Angewandte Chemie International Edition, 2010, 9995-9997, vol. 49, No. 51.

Josten, A., et al., "Use of microbial transglutaminase for the enzymatic biotinylation of antibodies," Journal of Immunological Methods, 2000, 47-54, vol. 240.

Junutula, J., et al., "Site-specific conjugation of a cytotoxic drug to an antibody improves the therapeutic index," Nature Biotechnology, 2008, 925-932, vol. 26, No. 8.

Kamiya, N., et al., "Site-specific cross-linking of functional proteins by transglutamination," Enzyme and Microbial Technology, 2003, 492-496, vol. 33.

Lin, C., et al., "Transglutaminase-Catalyzed Site-Specific Conjugation of Small-Molecule Probes to Proteins in Vitro and on the Surface of Living Cells," Journal of the American Chemical Society, 2006, 4542-4543, vol. 128.

Mero, A., et al., "Transglutaminase-Mediated PEGylation of Proteins: Direct Identification of the Sites of Protein Modification by Mass Spectrometry using a Novel Monodisperse PEG," Bioconjugate Chemistry, 2009, 384-389, vol. 20, No. 2.

Meusel, M. (2004). "Synthesis of Hapten-Protein Conjugates Using Microbial Transglutaminase." In C. M. Niemeyer (Ed.), "Methods in Molecular Biology, vol. 283: Bioconjugation Protocols: Strategies and Methods" (pp. 109-123). Totowa, NJ: Humana Press Inc.

Mindt T. et al., "Modification of Different IgG1 Antibodies via Glutamine and Lysine using Bacterial and Human Tissue Transglutaminase," Bioconjugate Chemistry, 2008, 271-278, vol. 19, No. 1.

Ohtsuka, T., et al., "Comparison of Substrate Specificities of Transglutaminases Using Synthetic Peptides as Acyl donors," Bioscience, Biotechnology, and Biochemistry, 2000, 2608-2613, vol. 64, No. 12.

Russell, D., et al., "Transglutaminase May Mediate Certain Physiological Effects of Endogenous Amines and of Amine-Containing Therapeutic Agents," Life Sciences, 1982, 1499-1508, vol. 30, No. 18.

Sato, H., "Enzymatic procedure for site-specific pegylation of proteins," Advanced Drug Delivery Reviews, 2002, 187-504, vol. 54.

Strop, P., et al., "Location Matters: Site of Conjugation Modulates Stability and Pharmacokinetics of Antibody Drug Conjugates," Chemistry & Biology, 2013, 161-167, vol. 20, No. 2.

Takazawa, T., et al., "Enzymatic Labeling of a Single Chain Variable Fragment of an Antibody With Alkaline Phosphatase by Microbial Transglutaminase," Biotechnology and Bioengineering, 2004, 399-404, vol. 86, No. 4.

Tanaka, T., et al., "N-terminal glycine-specific protein conjugation catalyzed by microbial transglutaminase," FEBS Letters, 2005, 2092-2096, vol. 579, No. 10.

Tanaka, T., et al., "Peptidyl Linkers for Protein Heterodimerization Catalyzed by Microbial Transglutaminase," Bioconjugate Chemistry, 2004, 491-497, vol. 15, No. 3.

Veronese, F., et al., "PEGylation, successful approach to drug delivery," Drug Discovery Today, 2005, 1451-1458, vol. 10, No. 21.

* cited by examiner

US 10,195,289 B2

ENGINEERED POLYPEPTIDE CONJUGATES USING TRANSGLUTAMINASE

RELATED APPLICATIONS

This application is a § 371 filing of PCT/IB2014/063566 filed Jul. 30, 2014, which claims the benefits of U.S. Provisional Application No. 61/860,757, filed Jul. 31, 2013, and U.S. Provisional Application No. 62/028,236, filed Jul. 23, 2014, which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC72025A_SEQListing_ST25.txt" created on Jan. 28, 2016 and having a size of 9KB. The sequence listing contained in this .txt file is part of the specification and is herein incorporated by reference in its entirety.

FIELD

The present invention relates generally to engineered polypeptide conjugates (e.g., antibody-drug conjugates) comprising specific acyl donor glutamine-containing tags and amine donor agents. The invention also relates to methods for making such engineered polypeptide conjugates using transglutaminase and methods of using thereof.

BACKGROUND

Antibody therapy provides targeted therapeutic treatment in patients with various disorders, such as cancers and immunological diseases, and therefore has played an important role in biological research. Different approaches of targeted antibody therapy, including antibody-drug conjugates (ADC), have been explored. See, e.g., Doronian et al., *Bioconj. Chem.* 19:1960-1963 (2008); and Junutula et al., *Nature Biotechnology* 26: 925-932 (2008).

In the case of antibody-drug conjugates (i.e., immunoconjugates), cytotoxic small molecules (drugs) are generally linked or conjugated to antibodies for targeted local delivery of the drug moieties to tumors. Chemical modification has been widely used for conjugating drugs to antibodies either through lysine side chain amines or through cysteine sulfhydryl groups activated by reducing interchain disulfide bonds. However, these types of "residue-specific" conjugation lead to a heterogeneous mixture of conjugates having different molar ratios of drug to antibody, different and non-specific conjugation sites, different efficiency, safety, and pharmacokinetics, and different clearance of antibody drug conjugates. See, e.g., Tanaka et al, *FEBS Letters* 579:2092-2096 (2005); and Wang et al., *Protein Sci.* 14: 2436-2446 (2005). Further, inclusion bodies or incorrect disulfide bridges may also be formed in cysteine-introduced antibodies. See, e.g., Gentle et al., *Bioconj. Chem.* 15:658-663 (2004). Reactive cysteine residues engineered at specific sites of antibodies (e.g., THIOMAB) for specific drug conjugation with defined stoichiometry has also been explored. See Junutula et al., *Nature Biotechnology*, 26: 925-932 (2008). However, expression and conjugation of such cysteine engineered antibodies and antibody-drug conjugates are complicated processes which require lengthy reaction procedures (e.g., reductions and oxidations). See, e.g., Gomez et al., *Biotechnology and Bioengineering*, 105 (4): 748-760 (2009). Antibody aggregates may also be generated during the process of making the cysteine engineered antibodies and the antibody-drug conjugates.

Enzymatic approaches using a transglutaminase for protein conjugation have been explored recently as an alternative to "residue-specific" conjugation of antibodies/proteins and drugs. Transglutaminases (EC2.3.2.13; protein-glutamine:gamma-glutamyltransferse; protein-glutamine:amine γ-glutamyltransferase; CAS 80146-85-6) belong to a family of enzymes that catalyze the acyl addition to a primary amine wherein the gamma-carboxamide group of peptide-bound γ-glutanyl residue is the acyl donor and the primary amine is the acyl acceptor and the amine donor. Transglutaminases have been used, for example, for the attachment of proteins to proteins. See, e.g., Tanaka et al, *FEBS Letters* 579:2092-2096 (2005). Enzymatic modification of antibodies using transglutaminases has also been reported. See Josten et al. *J. of Immunological Methods* 240:47-54 (2000); Takazawa et al., *Biotechnology and Bioengineering* 86(4): 399-404 (2004); Mindt et al., *Bioconj. Chem* 19:271-27 (2008), and Jeger et al., *Angewandte Chemie*, 49(51): 9995-9997 (2010). Protein conjugation or modification using transglutaminase provides the advantages of high selectivity, simplified reaction procedures, and mild reaction conditions. WO2012059882 describes site-specific conjugation of antibodies and small molecules mediated by a transglutaminase.

All publications, patents, and patent applications cited herein are hereby incorporated by reference herein in their entirety for all purposes to the same extent as if each individual publication, patent, and patent application were specifically and individually indicated to be so incorporated by reference. In the event that one or more of the incorporated literature and similar materials differs from or contradicts this application, including but not limited to defined terms, term usage, described techniques, or the like, this application controls.

SUMMARY

The present invention provides transglutaminase-mediated antibody drug conjugates comprising a specific acyl donor glutamine-containing tag engineered at a specific site of the antibody and an amine donor agent (e.g., linker-payload). The invention also provides a homogenous site-specific transglutaminase-mediated antibody drug conjugate (e.g., at least about 99.8% site-specific) comprising the amino acid substitution from glutamine (Q) to asparagine (N) at position 295 of the antibody (Q295N; EU numbering scheme).

In one aspect, this invention provides an engineered polypeptide conjugate comprising the formula: polypeptide-T-A, wherein T is an acyl donor glutamine-containing tag engineered at a specific site, wherein A is an amine donor agent, wherein the amine donor agent is site-specifically conjugated to the acyl donor glutamine-containing tag at a carboxyl terminus, an amino terminus, or at an another site in the polypeptide, and wherein the acyl donor glutamine-containing tag comprises an amino acid sequence GGLLQGPP (SEQ ID NO:13), LLQGPA (SEQ ID NO:4), or LLQGPP (SEQ ID NO:11).

In another aspect, the invention provides an engineered Fc-containing polypeptide conjugate comprising the formula: (Fc-containing polypeptide-T-A), wherein T is an acyl donor glutamine-containing tag engineered at a specific site, wherein A is an amine donor agent, wherein the amine donor agent is site-specifically conjugated to the acyl donor glutamine-containing tag at a carboxyl terminus, an amino terminus, or at an another site in the Fc-containing polypeptide, wherein the acyl donor glutamine-containing tag comprises an amino acid sequence XXQX (SEQ ID NO:35), wherein X is any amino acid (e.g., X can be the same or different amino acid), and wherein the engineered Fc-containing polypeptide conjugate comprises an amino acid substitution from glutamine to asparagine at position 295 (Q295N; EU numbering scheme). In some embodiments, the acyl donor glutamine-containing tag is LLQGPA (SEQ ID NO:4), LLQGP (SEQ ID NO:5), LLQGPP (SEQ ID NO:11) or GGLLQGPP (SEQ ID NO:13).

In some embodiments, the acyl donor glutamine-containing tag is not spatially adjacent to a reactive Lys (i.e., the ability to form a covalent bond as an amine donor in the presence of an acyl donor and a transglutaminase) in the polypeptide or the Fc-containing polypeptide.

In some embodiments, the polypeptide or the Fc-containing polypeptide comprises an amino acid modification at the last amino acid position in the carboxyl terminus relative to a wild-type polypeptide at the same position. The amino acid modification can be an amino acid deletion, insertion, substitution, mutation, or any combination thereof.

In some embodiments, the polypeptide conjugate comprises a full length antibody heavy chain and an antibody light chain, wherein the acyl donor glutamine-containing tag is located at the carboxyl terminus of a heavy chain, a light chain, or both the heavy chain and the light chain.

In some embodiments, the polypeptide conjugate comprises an antibody, wherein the antibody is a monoclonal antibody, a polyclonal antibody, a human antibody, a humanized antibody, a chimeric antibody, a bispecific antibody, a minibody, a diabody, or an antibody fragment. In some embodiments, the antibody is an IgG.

In some embodiments, the amine donor agent comprises the formula: X-Y-Z, wherein X is an amine donor unit; Y is a linker; and Z is an agent moiety. In some embodiments, the amine donor unit-linker (X-Y) is a branched unit (e.g., at least 2 units) and the agent moiety comprises at least about 2 agent moieties.

In some embodiments, the amine donor unit-linker (X-Y) is selected from the group consisting of Ac-Lys-Gly, aminocaproic acid, Ac-Lys-β-Ala, amino-PEG2-C2, amino-PEG3-C2, amino-PEG6-C2, Ac-Lys-Val-Cit-PABC, amino-PEG6-C2-Val-Cit-PABC, aminocaproyl-Val-Cit-PABC, [(3R,5R)-1-{3-[2-(2-aminoethoxy)ethoxy]propanoyl}piperidine-3,5-diyl]bis-Val-Cit-PABC, [(3S,5S)-1-{3-[2-(2-aminoethoxy)ethoxy]propanoyl}piperidine-3,5-diyl]bis-Val-Cit-PABC, putrescine, and Ac-Lys-putrescine.

In some embodiments, the agent moiety is a cytotoxic agent, including, but not limited to, an anthracycline, an auristatin, a camptothecin, a combretastatin, a dolastatin, a duocarmycin, an enediyne, a geldanamycin, an indolinobenzodiazepine dimer, a maytansine, a puromycin, a pyrrolobenzodiazepine dimer, a taxane, a *vinca* alkaloid, a tubulysin, a hemiasterlin, a spliceostatin, a pladienolide, and stereoisomers, isosteres, analogs, or derivatives thereof. For example, the cytotoxic agent is MMAD (Monomethyl Auristatin D) or 0101 (2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide).

In some embodiments, the amine donor agent (X-Y-Z) includes, but is not limited to, Alexa 488 cadaverine, 5-FITC cadaverine, Alexa 647 cadaverine, Alexa 350 cadaverine, 5-TAMRA cadaverine, 5-FAM cadaverine, SR101 cadaverine, 5,6-TAMRA cadaverine, 5-FAM lysine, Ac-Lys-Gly (acetyl-lysine-glycine)-MMAD, amino-PEG3-C2-MMAD, amino-PEG6-C2-MMAD, amino-PEG3-C2-amino-nonanoyl-MMAD, aminocaproyl-Val-Cit-PABC-MMAD, amino-PEG-C2-Val-Cit-PABC-MMAD, Ac-Lys-Val-Cit-PABC (acetyl-lysine-valine-citrulline-p-aminobenzyloxycarbonyl)-MMAD, aminocaproyl-MMAD, Ac-Lys-β-Ala-MMAD, amino-PEG2-C2-MMAE, aminocaproyl-MMAE, amino-PEG3-C2-MMAE, aminocaproyl-MMAF, aminocaproyl-Val-Cit-PABC-MMAE, amino-PEG-6-C2-Val-Cit-PABC-MMAE, Ac-Lys-Val-Cit-PABC-MMAE, aminocaproyl-Val-Cit-PABC-MMAF, amino-PEG-6-C2-Val-Cit-PABC-MMAF, Ac-Lys-Val-Cit-PABC-MMAF, Ac-Lys-Val-Cit-PABC-0101, putrescinyl-geldanamycin, Ac-Lys-putrescinyl-geldanamycin, aminocaproyl-3377, amino-PEG6-C2-3377, aminocaproyl-0131, amino-PEG6-C2-0131, [(3R,5R)-1-{3-(2-(2-aminoethoxy)ethoxy]propanoyl}piperidine-3,5-Val-Cit-PABC-MMAD, [(3R,5R)-1-{3-[2-(2-aminoethoxy)ethoxy]propanoyl}piperidine-3,5-diyl]bis-Val-Cit-PABC-MMAE, and 2-aminoethoxy-PEG6-NODAGA.

In another aspect, the invention provides a method for preparing an engineered Fc-containing polypeptide conjugate comprising the formula: (Fc-containing polypeptide-T-A), wherein T is an acyl donor glutamine-containing tag engineered at a specific site, wherein A is an amine donor agent, wherein the amine donor agent is site-specifically conjugated to the acyl donor glutamine-containing tag at a carboxyl terminus, an amino terminus, or at an another site in the Fc-containing polypeptide, wherein the acyl donor glutamine-containing tag comprises an amino acid sequence XXQX (SEQ ID NO:35), wherein X is any amino acid (e.g., X can be the same or a different amino acid), and wherein the engineered Fc-containing polypeptide conjugate comprises an amino acid substitution from glutamine to asparagine at position 295 (Q295N; EU numbering scheme), comprising the steps of: a) providing an engineered (Fc-containing polypeptide)-T molecule comprising the Fc-containing polypeptide and the acyl donor glutamine-containing tag; b) contacting the amine donor agent with the engineered (Fc-containing polypeptide)-T molecule in the presence of a transglutaminase; and c) allowing the engineered (Fc-containing polypeptide)-T to covalently link to the amine donor agent to form the engineered Fc-containing polypeptide conjugate. In some embodiments, the engineered Fc-containing polypeptide-T is expressed in CHO cells In another aspect, the invention provides a method for preparing an engineered polypeptide conjugate comprising the formula: polypeptide-T-A, wherein T is an acyl donor glutamine-containing tag engineered at a specific site, wherein A is an amine donor agent, wherein the amine donor agent is site-specifically conjugated to the acyl donor glutamine-containing tag at a carboxyl terminus, an amino terminus, or at an another site in the polypeptide, and wherein the acyl donor glutamine-containing tag comprises an amino acid sequence LLQGPX, wherein X is A or P (SEQ ID NO:14), or GGLLQGPP (SEQ ID NO:13), comprising the steps of: a) providing an engineered polypeptide-T molecule comprising the polypeptide and the acyl donor glutamine-containing tag; b) contacting the amine donor agent with the engineered polypeptide-T molecule in the presence of a transglutaminase; and c) allowing the engineered polypeptide-T to covalently link to the amine donor agent to form the engineered Fc-containing polypeptide conjugate. In some embodiments, the engineered polypeptide-T molecule is expressed in CHO cells.

In some embodiments, the engineered polypeptide conjugate (e.g., the engineered Fc-containing polypeptide conjugate, the engineered Fab-containing polypeptide conjugate, or the engineered antibody conjugate) as described herein has conjugation efficiency of at least about 51%.

In another aspect, the invention provides a pharmaceutical composition comprising the engineered polypeptide conjugate as described herein (e.g., the engineered Fc-containing polypeptide conjugate, the engineered Fab-containing polypeptide conjugate, or the engineered antibody conjugate) and a pharmaceutically acceptable excipient.

In another aspect, the invention provides a method of treating a cancer in a subject in need thereof, comprising administering to the subject an effective amount of the pharmaceutical composition comprising the engineered polypeptide conjugate (e.g., the engineered Fc-containing polypeptide conjugate, the engineered Fab-containing polypeptide conjugate, or the engineered antibody conjugate) as described herein.

In another aspect, the invention provides a method of inhibiting tumor growth or progression in a subject in need thereof, comprising administering to the subject an effective amount of the pharmaceutical composition comprising the engineered polypeptide conjugate (e.g., the engineered Fc-containing polypeptide conjugate, the engineered Fab-containing polypeptide conjugate, or the engineered antibody conjugate) as described herein.

In another aspect, the invention provides a method of diagnosing cancer in a subject suspected of suffering from cancer, comprising a) contacting a sample of the subject with the engineered polypeptide conjugate (e.g., the engineered Fc-containing polypeptide conjugate, the engineered Fab-containing polypeptide conjugate, or the engineered antibody conjugate) as described herein under conditions that result in binding of the engineered polypeptide conjugate with a cancer-related protein, and b) determining binding of the engineered polypeptide conjugate to the cancer-related protein.

In another aspect, the invention provides an engineered polypeptide conjugate (e.g., the engineered Fc-containing polypeptide conjugate, the engineered Fab-containing polypeptide conjugate, or the engineered antibody conjugate) purified by the methods described herein.

BRIEF DESCRIPTION OF THE DRAWINGS

FIG. 1A depicts the results of the glutamine tag TG6 (SEQ ID NO: 1) in Ab-TG6. FIG. 1B depicts the results of the glutamine tag TG9 (SEQ ID NO:4) in Ab-TG9. FIG. 1C depicts the results of the glutamine tag TG10 (SEQ ID NO:5) in Ab-TG10. FIG. 1D depicts the results for the glutamine tag TG17 (SEQ ID NO:11) in Ab-TG17.

DETAILED DESCRIPTION

Figure 1A:
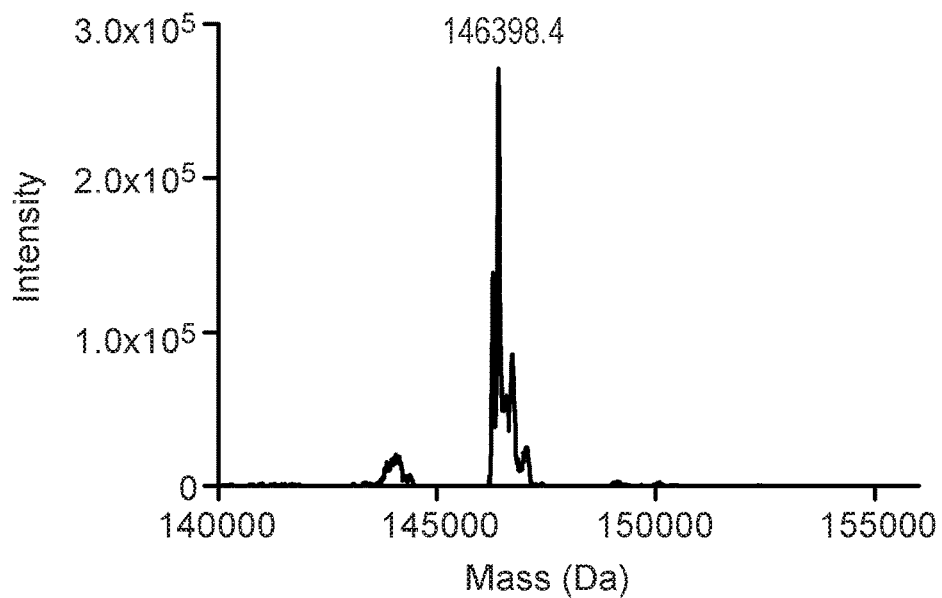
FIGS. 1A-1D depict graphs showing different percentages of the clipping of four different acyl donor glutamine-containing tags (the "glutamine tags") expressed in CHO cells.
Figure 1A:
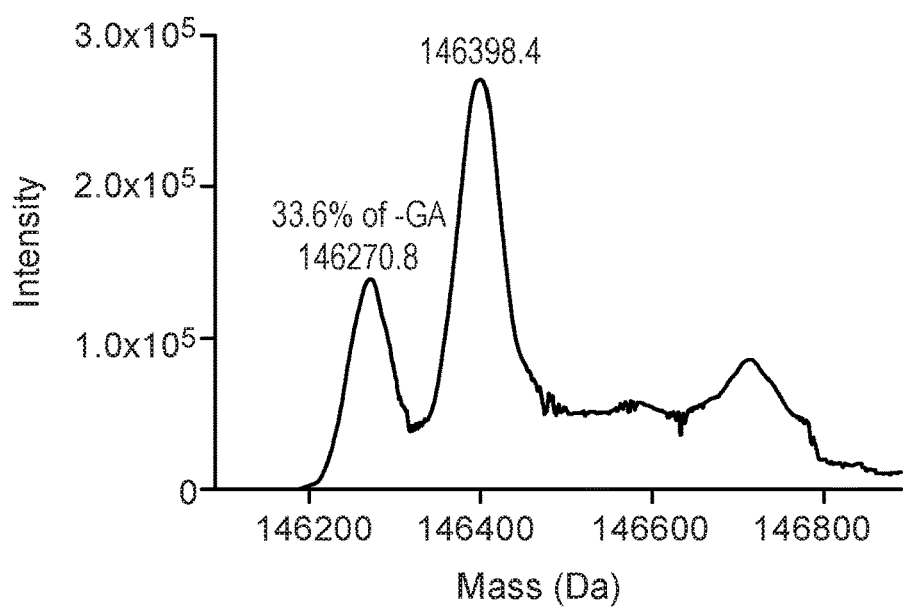
Figure 1B:
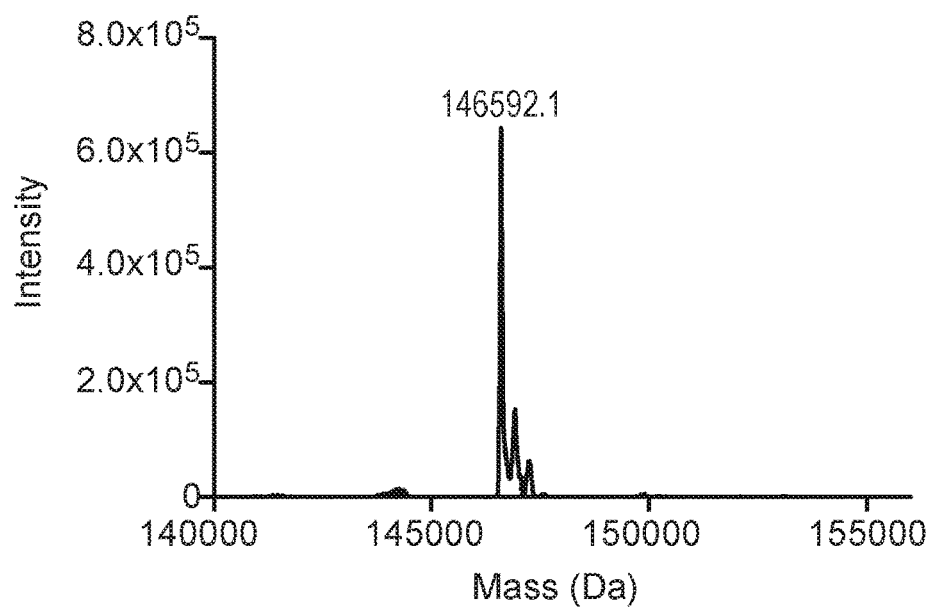
Figure 1B:
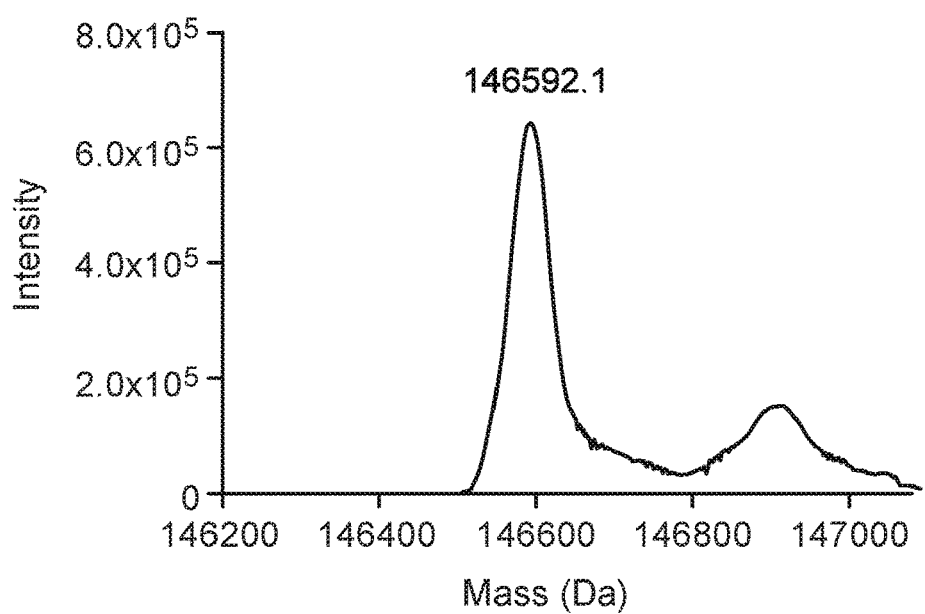
Figure 1C:
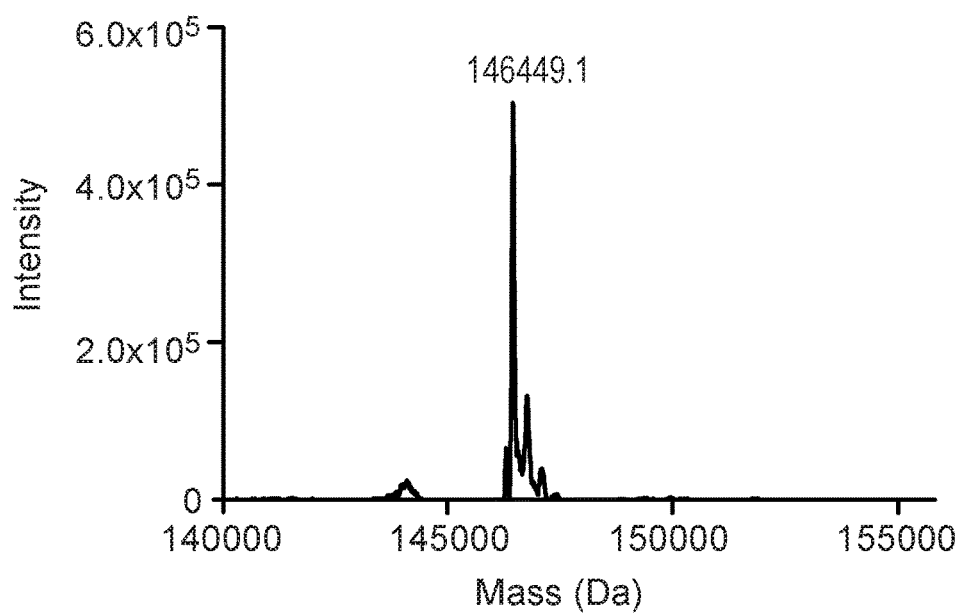
Figure 1C:
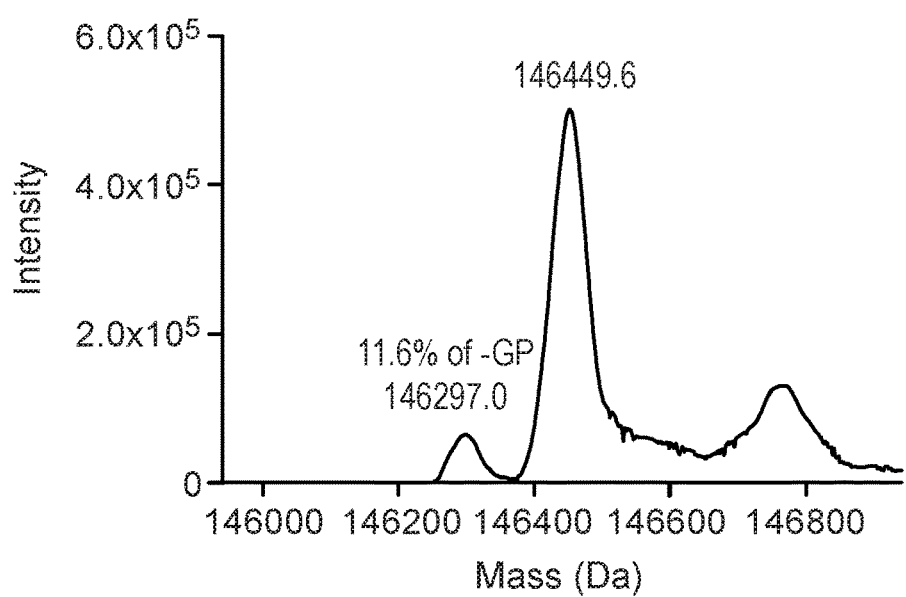
Figure 1D:
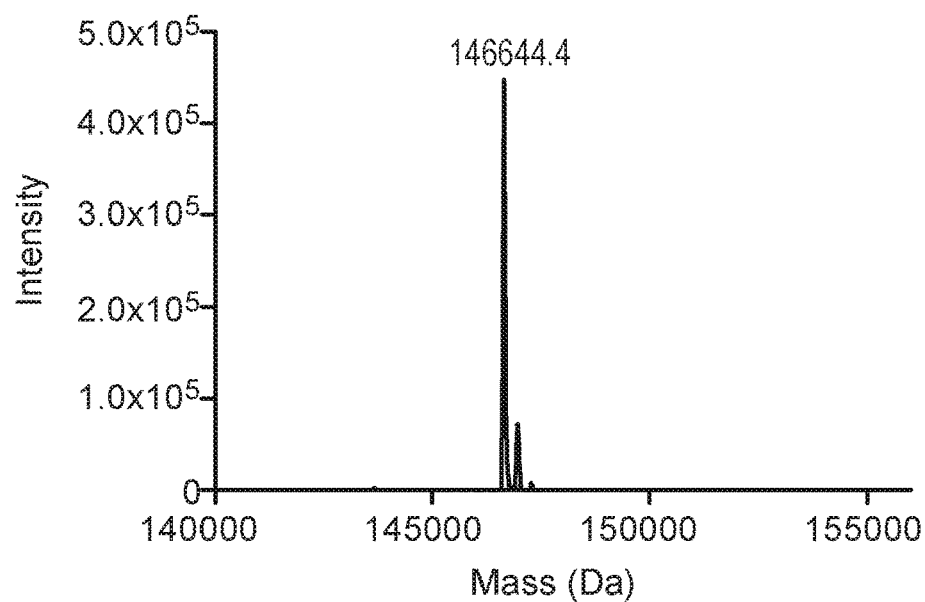
Figure 1D:
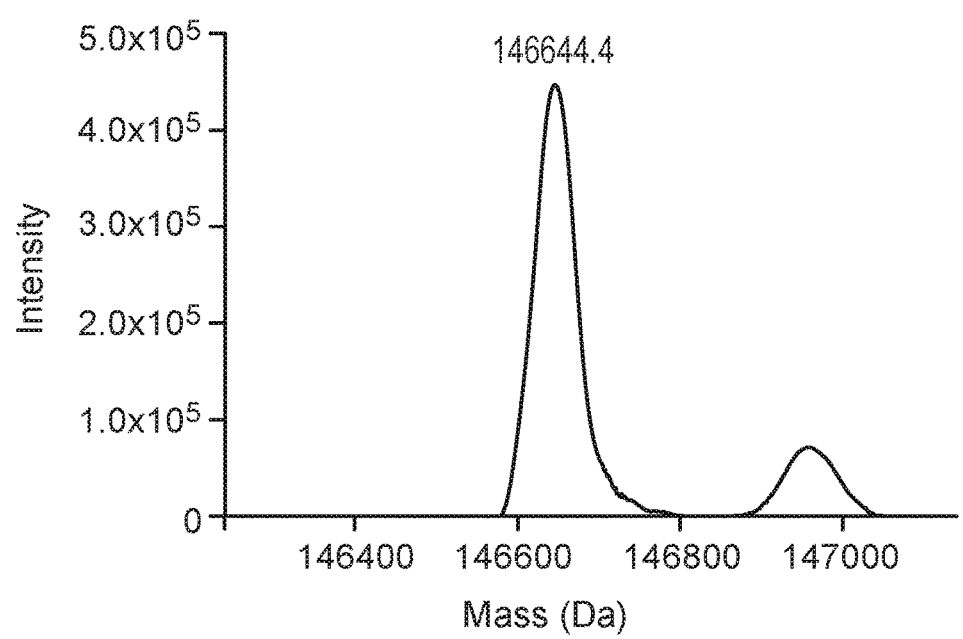

The present invention provides transglutaminase-mediated antibody-drug conjugates comprising a specific acyl donor glutamine-containing tag engineered at a specific site of the antibody and an amine donor agent (e.g., linker-payload). The invention also provides a homogenous site-specific transglutaminase-mediated antibody-drug conjugate comprising the amino acid substitution from glutamine (Q) to asparagine (N) at position 295 (Q295N; EU numbering scheme). The inventors have discovered that proteolysis of an acyl donor glutamine-containing tag engineered at C-terminus of an antibody's heavy chain or light chain, when expressed in CHO cells, can be prevented by using several newly designed glutamine-containing tags having unique sequences (e.g., LLQGPA (SEQ ID NO:4), LLQGPP (SEQ ID NO:11), and GGLLQGPP (SEQ ID NO:13)). The inventors have also discovered that mutation at position 295 (i.e., Q295N; EU numbering scheme) of the antibody drug conjugate eliminates the off-target conjugation of a small percentage of aglycosylated antibody at position 295 and yields highly homogenous conjugates that are better than 99.8% site-specific.

Accordingly, in one aspect, the invention provides an engineered polypeptide conjugate comprising the formula: polypeptide-T-A, wherein T is an acyl donor glutamine-containing tag engineered at a specific site; wherein A is an amine donor agent; wherein the amine donor agent is site-specifically conjugated to the acyl donor glutamine-containing tag at a carboxyl terminus, an amino terminus, or at an another site in the polypeptide, and wherein the acyl donor glutamine-containing tag comprises an amino acid sequence LLQGPX, wherein X is A or P (SEQ ID NO:14), or GGLLQGPP (SEQ ID NO:13). In some embodiments, the polypeptide is an Fc-containing polypeptide or a Fab-containing polypeptide.

In another aspect, the invention provides an engineered Fc-containing polypeptide conjugate comprising the formula: (Fc-containing polypeptide)-T-A, wherein T is an acyl donor glutamine-containing tag engineered at a specific site; wherein A is an amine donor agent; wherein the amine donor agent is site-specifically conjugated to the acyl donor glutamine-containing tag at a carboxyl terminus, an amino terminus, or at an another site in the Fc-containing polypeptide, wherein the acyl donor glutamine-containing tag comprises an amino acid sequence XXQX (SEQ ID NO:35), wherein X is any amino acid, and wherein the engineered Fc-containing polypeptide conjugate comprises an amino acid substitution from glutamine to asparagine at position 295 (Q295N; EU numbering scheme).

In another aspect, the invention provides a method for preparing an engineered polypeptide conjugate comprising the formula: polypeptide-T-A, wherein T is an acyl donor glutamine-containing tag engineered at a specific site, wherein A is an amine donor agent; wherein the amine donor agent is site-specifically conjugated to the acyl donor glutamine-containing tag at a carboxyl terminus, an amino terminus, or at an another site in the polypeptide, and wherein the acyl donor glutamine-containing tag comprises an amino acid sequence LLQGPX, wherein X is A or P (SEQ ID NO:14), or GGLLQGPP (SEQ ID NO:13), comprising the steps of: a) providing an engineered polypeptide-T molecule comprising the polypeptide and the acyl donor glutamine-containing tag; b) contacting the amine donor agent with the engineered polypeptide-T molecule in the presence of a transglutaminase; and c) allowing the engineered polypeptide-T to covalently link to the amine donor agent to form the engineered polypeptide conjugate. In some embodiments, the engineered polypeptide is an Fc-containing polypeptide or a Fab-containing polypeptide. In some embodiments, the engineered polypeptide-T molecule is expressed in CHO cells.

General Techniques and Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, molecular biology, biochemistry, immunology, analytical chemistry, synthetic organic chemistry, and medicinal and pharmaceutical chemistry described herein are those well known and commonly used in the art. Throughout this specification and claims, the word "comprise," or variations such as "comprises" or "comprising," will be understood to imply the inclusion of a stated integer or group of integers but not the exclusion of any other integer or group of integers.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

The term "Fc-containing polypeptide" as used herein refers to a polypeptide (e.g., an antibody or an immunoadhesin) comprising the carboxyl terminal polypeptide sequences of an immunoglobulin heavy chain. The Fc-containing polypeptide may comprise native or variant Fc regions (i.e., sequences). The Fc region of an immunoglobulin generally comprises two constant domains, a CH2 domain and a CH3 domain, and optionally comprises a CH4 domain. An Fc-containing polypeptide may comprise part or all of a wild-type hinge sequence (generally at amino terminus of the Fc-containing polypeptide). An Fc-containing polypeptide may also be a dimer. An Fc-containing polypeptide may be obtained or derived from any suitable immunoglobulin, such as from at least one of the various IgG1, IgG2, IgG3, or IgG4 subtypes, or from IgA, IgE, IgD or IgM. Although the boundaries of the Fc region of an immunoglobulin heavy chain might vary, for example, the human IgG heavy chain Fc region is usually defined to stretch from an amino acid residue at position Glu216, or from Ala231, to the carboxyl-terminus thereof.

An Fc-containing polypeptide may be an Fc-containing fusion polypeptide, wherein one or more polypeptides are operably linked to an Fc-containing polypeptide. An Fc fusion combines the Fc polypeptide of an immunoglobulin with a fusion partner, which in general may be any protein, polypeptide, or small molecule. Virtually any protein or small molecule may be linked to the Fc region to generate an Fc-containing fusion polypeptide. Fc-containing fusion partners may include, but are not limited, the target-binding region of a receptor, an adhesion molecule, a ligand, an enzyme, a cytokine, a chemokine, or some other protein or protein domain.

The term "acyl donor glutamine-containing tag", "glutamine tag," "Q-containing tag", or "Q-tag" as used herein refers to a polypeptide or a protein containing one or more Gln residue(s) that acts as a transglutaminase amine acceptor.

The term "amine donor agent" or "acyl acceptor" as used herein refers to an agent containing one or more reactive amines (e.g., primary amines). For example, the amine donor agent can comprise an amine donor unit (e.g., primary amine $NH_2$), a linker, and an agent moiety (e.g., a small molecule). The amine donor agent can also be a polypeptide (e.g., an antibody) or a biocompatible polymer containing a reactive Lys (e.g., an endogenous Lys).

As used herein, the term "biocompatible polymer" refers to a polymer (e.g., repeating monomeric or structural units) that is suitable for therapeutic or medical treatment in a recipient (e.g., human) without eliciting any undesirable local or systemic effects in the recipient. A biocompatible polymer (synthetic, recombinant, or native) can be a water soluble or water insoluble polymer. A biocompatible polymer can also be a linear or a branched polymer.

As used herein, the term "site specificity," "site-specifically conjugated," or "site-specifically crosslinked" refers to the specific conjugation or crosslinking of the amine donor agent to the polypeptide engineered with an acyl donor glutamine-containing tag at a specific site (e.g., carboxyl terminus or amino terminus of the antibody or toxin polypeptide, accessible site in the antibody (e.g., antibody light chain and/or heavy chain loops) or toxin polypeptide (e.g., polypeptide loops)). The polypeptide engineered with an acyl donor glutamine-containing tag can be an Fc-containing polypeptide, Fab-containing polypeptide, or a toxin polypeptide (e.g., a protein bound to an ion channel). The term "site specificity," "site-specifically conjugated," or "site-specifically crosslinked" can also refer to the specific conjugation or crosslinking of the polypeptide (e.g., toxin polypeptide) to the biocompatible polymer engineered with an acyl donor glutamine-containing tag at a specific site (e.g., an accessible site in the biocompatible polymer). Site specificity can be measured by various techniques, including, but not limited to, mass spectrometry (e.g., matrix-assisted laser-desorption ionization mass spectrometry (MALDI-MS), electrospray ionization mass spectrometry (ESI-MS), tandem mass spectrometry (MS), and time-of-flight mass spectrometry (TOF-MS)), hydrophobic interaction chromatography, ion exchange chromatography, site-directed mutagenesis, fluorescence-labeling, size exclusion chromatography, and X-ray crystallography.

As used herein, the term "spatially adjacent to" refers to interference with the desired transglutaminase reaction (e.g., lysine residue that is located such that it can interfere with the conjugation reaction by serving as an amine donor agent).

As used herein, the term "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, unless otherwise indicated by context, the term is intended to encompass not only intact polyclonal or monoclonal antibodies, but also fragments thereof (such as Fab, Fab', F(ab')$_2$, Fv), single chain (ScFv) and domain antibodies, including shark and camelid antibodies), and fusion proteins comprising an antibody portion, multivalent antibodies, multispecific antibodies (e.g., bispecific antibodies so long as they exhibit the desired biological activity) and antibody fragments as described herein, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. On one aspect, the immunoglobulin is a human, murine, or rabbit immunoglobulin.

The term "Fab containing polypeptide" as used herein refers to a polypeptide comprising a Fab fragment, Fab' fragment, or "(Fab')2 fragment. A Fab-containing polypeptide may comprise part or all of a wild-type hinge sequence (generally at the carboxyl terminus of the Fab portion of the polypeptide). A Fab-containing polypeptide may be obtained or derived from any suitable immunoglobulin, such as from at least one of the various IgG1, IgG2, IgG3, or IgG4 subtypes, or from IgA, IgE, IgD or IgM. A Fab-containing polypeptide may be a Fab-containing fusion polypeptide, wherein one or more polypeptides are operably linked to a Fab-containing polypeptide. A Fab fusion combines the Fab polypeptide of an immunoglobulin with a fusion partner, which in general may be any protein, polypeptide, or small molecule. Virtually any protein or small molecule may be linked to the Fab polypeptide to generate a Fab-containing fusion polypeptide. Fab-containing fusion partners may include, but are not limited to, the target-binding region of a receptor, an adhesion molecule, a ligand, an enzyme, a cytokine, a chemokine, or some other protein or protein domain.

A "Fab fragment" is comprised of one light chain and the CH1 and variable regions of one heavy chain. The heavy chain of a Fab molecule cannot form a disulfide bond with another heavy chain molecule.

A "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form a F(ab')2 molecule.

A "F(ab')2 fragment" contains two light chains and two heavy chains containing a portion of the constant region between the CH1 and CH2 domains, such that an interchain disulfide bond is formed between the two heavy chains. A F(ab')2 fragment thus is composed of two Fab' fragments that are held together by a disulfide bond between the two heavy chains.

"Antibody fragments" as used herein comprise only a portion of an intact antibody, wherein the portion preferably retains at least one, preferably most or all, of the functions normally associated with that portion when present in an intact antibody.

A "multispecific antibody" is one that targets more than one antigen or epitope. A "bispecific," "dual-specific" or "bifunctional" antibody is a hybrid antibody having two different antigen binding sites. Bispecific antibodies are a species of multispecific antibody and may be produced by a variety of methods including, but not limited to, fusion of hybridomas or linking of Fab' fragments. See, e.g., Songsivilai & Lachmann (1990), *Clin. Exp. Immunol.* 79:315-321; and Kostelny et al. (1992), *J. Immunol.* 148:1547-1553. The two binding sites of a bispecific antibody will bind to two different epitopes, which may reside on the same or different protein targets.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Further, in contrast to polyclonal antibody preparations that typically include different antibodies directed against different determinants (epitopes), each monoclonal antibody is directed against a single determinant on the antigen.

The monoclonal antibodies herein may, in certain embodiments, specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Humanized antibodies may, moreover, comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

As used herein, the term "immunoadhesin" designates antibody-like or immunoglobulin-like molecules which combine the "binding domain" of a heterologous protein (an "adhesin", e.g. a receptor, ligand or enzyme) with the effector component of immunoglobulin constant domains (i.e., Fc domain). Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as IgG1, IgG2, IgG3, or IgG4 subtypes, IgA, IgE, IgD or IgM.

The "hinge region," "hinge sequence," and variation thereof, as used herein, includes the meaning known in the art, which is illustrated, for example, Janeway et al., ImmunoBiology: the immune system in health and disease, (Elsevier Science Ltd., NY) ($4^{th}$ ed., 1999); Bloom et al., Protein Science (1997), 6:407-415; Humphreys et al., *J. Immunol. Methods* (1997), 209:193-202.

As used herein, the term "wild-type amino acid," "wild-type IgG," "wild-type bispecific antibody," or "wild-type mAb" refers to a sequence of amino acids or nucleic acids that occurs naturally within a certain population (e.g., human, mice, rats, cells, etc.).

As used herein, the term "conjugation efficiency" or "crosslinking efficiency" is the ratio between the experimentally measured amount of engineered polypeptide conjugate divided by the maximum expected engineered polypeptide conjugate amount. Conjugation efficiency or crosslinking efficiency can be measured by various techniques well known to persons skilled in the art, such as hydrophobic interaction chromatography. Conjugation efficiency can also be measured at different temperature, such as room temperature or 37° C.

The term "effector function" refers to the biological activities attributable to the Fc region of an antibody. Examples of antibody effector functions include, but are not limited to, antibody-dependent cell-mediated cytotoxicity (ADCC), Fc receptor binding, complement dependent cytotoxicity (CDC), phagocytosis, C1q binding, and down regulation of cell surface receptors (e.g., B cell receptor; BCR). See, e.g., U.S. Pat. No. 6,737,056. Such effector functions generally require the Fc region to be combined with a binding domain (e.g., an antibody variable domain) and can be assessed using various assays known in the art for evaluating such antibody effector functions. An exemplary measurement of effector function is through Fcγ3 and/or C1q binding.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, *PNAS (USA)*, 95:652-656.

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods*, 202: 163 (1996), may be performed.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, FcγRIII, and FcγRIV subclasses, including allelic variants and alternatively spliced forms of these receptors. FcγRll receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, *Ann. Rev. Immunol.*, 9:457-92; Capel et al., 1994, *Immunomethods*, 4:25-34; de Haas et al., 1995, *J. Lab. Clin. Med.*, 126:330-41; Nimmerjahn et al., 2005, *Immunity* 23:2-4. "FcR" also includes the neonatal receptor, FcRn, which is responsible for the transfer of maternal IgGs to the fetus (Guyer et al., 1976, *J. Immunol.*, 117:587; and Kim et al., 1994, *J. Immunol.*, 24:249).

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of tumor, cancer remission, decreasing cancer symptoms, increasing the quality of life of those suffering from cancer, decreasing the dose of other medications required to treat cancer, delaying the progression of cancer, curing cancer, and/or prolong survival of a cancer patients.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various cancer-related diseases or conditions (such as gastric, head and neck, lung, ovarian, and pancreatic cancers), decreasing the dose of other medications required to treat the disease, enhancing the effect of another medication, and/or delaying the progression of the cancer in patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

The term "purify," and grammatical variations thereof, is used to mean the removal, whether completely or partially, of at least one impurity from a mixture containing the polypeptide and one or more impurities, which thereby improves the level of purity of the polypeptide in the composition (i.e., by decreasing the amount (ppm) of impurity(ies) in the composition).

Reference to "about" a value or parameter herein includes (and describes) embodiments that are directed to that value or parameter per se. For example, description referring to "about X" includes description of "X." Numeric ranges are inclusive of the numbers defining the range.

An "individual" or a "subject" is a mammal, more preferably, a human. Mammals also include, but are not limited to, farm animals, sport animals, pets, primates, horses, dogs, cats, mice, and rats.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

The residue designations in this application are based on the EU numbering scheme of the constant domain (Edelman et al., *Proc. Natl. Acad. Sci. USA*, 63(1):78-85 (1969)).

Unless otherwise defined, all technical and scientific terms used herein have the same meaning as commonly understood by one of ordinary skill in the art to which this invention belongs. Exemplary methods and materials are described herein, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. The materials, methods, and examples are illustrative only and not intended to be limiting Engineered Polypeptide Conjugates The engineered polypeptide conjugates herein comprise a polypeptide (e.g., Fc-containing polypeptide, Fab-containing polypeptide, or antibody) engineered to a specific acyl donor glutamine-containing tag, wherein the polypeptide is site-specifically conjugated to an amine donor agent (e.g., a small molecule coupled to a linker) via the acyl donor glutamine-containing tag. The engineered polypeptide (e.g., Fc-containing polypeptide or antibody) can also be modified to eliminate the off-target conjugation between the acyl donor glutamine-containing tag and the amine donor agent to achieve highly homogenous polypeptide conjugates that are at least about 99% site-specific.

In one aspect, provided is an engineered polypeptide conjugate comprising the formula: polypeptide-T-A, wherein T is an acyl donor glutamine-containing tag engineered at a specific site, wherein A is an amine donor agent, wherein the amine donor agent is site-specifically conjugated to the acyl donor glutamine-containing tag at a carboxyl terminus, an amino terminus, or at an another site in the polypeptide, and wherein the acyl donor glutamine-containing tag comprises an amino acid sequence LLQGPX, wherein X is A or P (SEQ ID NO:14), or GGLLQGPP (SEQ ID NO:13). In some embodiments, the polypeptide is a Fc-containing polypeptide or a Fab-containing polypeptide.

In another aspect, provided is an engineered Fc-containing polypeptide conjugate comprising the formula: (Fc-containing polypeptide)-T-A, wherein T is an acyl donor glutamine-containing tag engineered at a specific site, wherein A is an amine donor agent, wherein the amine donor agent is site-specifically conjugated to the acyl donor glutamine-containing tag at a carboxyl terminus, an amino terminus, or at an another site in the Fc-containing polypeptide, wherein the acyl donor glutamine-containing tag comprises an amino acid sequence XXQX (SEQ ID NO:35), wherein X is any amino acid, and wherein the engineered Fc-containing polypeptide conjugate comprises an amino acid substitution from glutamine to asparagine at position 295 (e.g., Q295N; EU numbering scheme).

Both the acyl donor glutamine-containing tag and the amine donor agent described herein are substrates for transglutaminase, and the linkage between the acyl donor glutamine-containing tag and the amine donor agent is of the formula $CH_2$—$CH_2$—CO—NH—, wherein NH— is linked to a linker and an agent moiety. The transglutaminase used in the invention described herein can be obtained or made from a variety of sources. In some embodiments, the transglutaminase is a calcium dependent transglutaminase which requires calcium to induce enzyme conformational changes and allow enzyme activity. For example, transglutaminase can be derived from guinea pig liver and obtained through commercial sources (e.g., Sigma-Aldrich (St Louis, Mo.) and MP Biomedicals (Irvine, Calif.)). In some embodiments, the transglutaminase is a calcium independent transglutaminase which does not require calcium to induce enzyme conformational changes and allow enzyme activity. In some embodiments, the transglutaminase is a microbial transglutaminase derived from a microbial genome, such as transglutaminase from *Streptoverticillium* or *Streptomyces* (e.g., *Streptomyces mobarensis* or *Streptoverticillium mobarensis*). Commercially available calcium independent transglutaminase such as ACTIVA™ (Ajinomoto, Japan) is suitable for the present invention. In some embodiments, the transglutaminase is a mammalian protein (e.g., human transglutaminase), a bacterial protein, a plant protein, a fungi protein (e.g., *Oomycetes* and *Actinomicetes* transglutaminases), or a prokaryotic protein. In some embodiments, the transglutaminase is from *Micrococcus, Clostridium, Turolpsis, Rhizopus, Monascus*, or *Bacillus*.

In some embodiments, the transglutaminase used in the invention described herein is an engineered transglutaminase, which catalyzes transamidation of 1) one or more exogenous glutamine residues on the acyl donor glutamine-containing tag and additionally/optionally 2) endogenous glutamine residues in the antibody, with one or more lysine residues or reactive amines in the amine donor agent. For example, one or more wild-type amino acid residues in the naturally occurring transglutaminase are deleted, replaced or substituted with another amino acid residue(s) to make the engineered transglutaminase.

In some embodiments, the transglutaminase used in the invention described herein can also be a recombinant protein produced using recombinant techniques known to persons skilled in the art. In some embodiments, the transglutaminase used in the invention described herein can be a purified protein. For example, the purified transglutaminase is least about 50% pure. As used herein, "pure" or "purified" protein refers to a protein (e.g., transglutaminase) free from other protein contaminants. In some embodiments, the purified transglutaminase is at least about any of 55%-60%, 60%-65%, 65%-70%, 70%-75%, 75%-80%, 80%-85%, 85%-90%, 90%-95%, 95%-98%, or 99% pure. In some embodiments, the purified transglutaminase is about any of 50%, 55%, 60%, 65%, 70%, 75%, 80%, 85%, 90%, 95%, 96%, 97%, 98%, 99%, or 100% pure.

In some embodiments, the acyl donor glutamine-containing tag of the engineered polypeptide (e.g., Fc-containing, Fab-containing polypeptide, or antibody) conjugate as described herein is not spatially adjacent to a reactive Lys in the polypeptide. For example, the acyl donor glutamine-containing tag is not spatially adjacent to a reactive Lys in the carboxyl terminus, the amino terminus, or both the carboxyl and the amino termini of the polypeptide.

In some embodiments, the acyl donor glutamine-containing tag comprises an amino acid sequence XXQX (SEQ ID NO:35), wherein X can be a conventional or nonconventional amino acid, as described herein, and can be the same or a different amino acid. In some embodiments, X is L (Leu), A (Ala), G (Gly), S (Ser), V (Val), F (Phe), Y (Tyr), H (His), R (Arg), N (Asn), E (Glu), D (Asp), C (Cys), Q (Gln), I (Ile), M (Met), P (Pro), T (Thr), K (Lys), or W (Trp). In some embodiments, the acyl donor glutamine-containing tag comprises an amino acid sequence selected from the group consisting of LLQGG (SEQ ID NO:16), LLQG (SEQ ID NO:17), LSLSQG (SEQ ID NO:18), GGGLLQGG (SEQ ID NO:19), GLLQG (SEQ ID NO:20), LLQ, GSPLAQSHGG (SEQ ID NO:21), GLLQGGG (SEQ ID NO:22), GLLQGG (SEQ ID NO:23), GLLQ (SEQ ID NO:24), LLQLLQGA (SEQ ID NO:25), LLQGA (SEQ ID NO:26), LLQYQGA (SEQ ID NO:27), LLQGSG (SEQ ID NO:28), LLQYQG (SEQ ID NO:29), LLQLLQG (SEQ ID NO:30), SLLQG (SEQ ID NO:31), LLQLQ (SEQ ID NO:32), LLQLLQ (SEQ ID NO:33), LLQGR (SEQ ID NO:34), LLQGPP (SEQ ID NO:11), LLQGPA (SEQ ID NO:4), GGLLQGPP (SEQ ID NO:13), GGLLQGA (SEQ ID NO:12), LLQGA (SEQ ID NO:1), LLQGPGK (SEQ ID NO:2), LLQGPG (SEQ ID NO:3), LLQGP (SEQ ID NO:5), LLQP (SEQ ID NO:6), LLQPGK (SEQ ID NO:7), LLQAPGK (SEQ ID NO:8), LLQGAPG (SEQ ID NO:9), and LLQGAP (SEQ ID NO:10). In some embodiments, the acyl donor glutamine-containing tag comprises an amino acid sequence LLQGPA (SEQ ID NO:4), LLQGP (SEQ ID NO:5), LLQGPP (SEQ ID NO:11), or GGLLQGPP (SEQ ID NO:13). In some embodiments, the acyl donor glutamine-containing tag does not comprise an amino acid sequence selected from the group consisting of LGGQGGG (SEQ ID NO:41), GGGQGGL (SEQ ID NO:42), GXGQGGG (SEQ ID NO:43), GGXQGGG (SEQ ID NO:44), GGGQXGG (SEQ ID NO:45), and GGGQGXG (SEQ ID NO:46), wherein X is G, A, S, L, V, F, Y, R, N, or E).

In some embodiments, the polypeptide (e.g., Fc-containing polypeptide, Fab-containing polypeptide, or antibody) of the engineered polypeptide conjugate comprises an amino acid modification at the last amino acid position in the carboxyl terminus relative to a wild-type polypeptide at the same position. In some embodiments, the modification is an amino acid deletion, insertion, substitution, mutation, or any combination thereof. In some embodiments, the substitution comprises replacing a wild type amino acid with another (e.g., a non-wild type amino acid). In some embodiments, the insertion comprises inserting one or more amino acid(s) (e.g., inserting one, two, three or more amino acids). In some embodiments, the other (e.g., non-wild type) or inserted amino acid is Arg. In some embodiments, the other (e.g., non-wild type) amino acid is Ala, Asn, Asp, Cys, Glu, Gln, Gly, His, Ile, Leu, Met, Phe, Pro, Ser, Thr, Trp, Tyr, or Val. For example, in some embodiments, the last amino acid in the carboxyl terminus of the polypeptide (e.g., the heavy chain of an antibody) can be deleted, and the acyl donor glutamine-containing tag engineered to the C-terminus of the polypeptide comprises the amino acid sequence LLQGPA (SEQ ID NO:4) or LLQGPP (SEQ ID NO:11).

In some embodiments, the polypeptide (e.g., Fc-containing polypeptide or antibody) of the engineered polypeptide conjugate comprises an amino acid modification at position 222, 340, or 370 (EU numbering) relative to the wild-type polypeptide at the same position. In some embodiments, the modification is an amino acid deletion, insertion, substitution, mutation, or any combination thereof. In some embodiments, the substitution comprises replacing a wild type amino acid with another (e.g., a non-wild type amino acid). In some embodiments, the other (e.g., non-wild type) or inserted amino acid is Arg (e.g., K222R, K340R, or K370R (EU numbering)). In some embodiments, the insertion comprises inserting one or more amino acid(s) (e.g., inserting one, two, three or more amino acids). In some embodiments, the other (e.g., non-wild type) amino acid is Ala, Asn, Asp, Cys, Glu, Gln, Gly, His, Ile, Leu, Met, Phe, Pro, Ser, Thr, Trp, Tyr, or Val. For example, in some embodiments, the polypeptide (e.g., an antibody) comprising the K222R substitution is engineered to the acyl donor glutamine-containing tag at the C-terminus of the light chain of the antibody, wherein the glutamine-containing tag comprises an amino acid sequence of GGLLQGPP (SEQ ID NO:13).

In some embodiments, the polypeptide (e.g., Fc-containing polypeptide, Fab-containing polypeptide, or antibody) comprises an amino acid modification at the first amino acid position in the amino terminus relative to a wild-type polypeptide at the same position. In some embodiments, the modification is an amino acid deletion, insertion, substitution, mutation, or any combination thereof. In some embodiments, the substitution comprises replacing a wild type amino acid with another (e.g., non-wild type) amino acid. In some embodiments, the insertion comprises inserting an amino acid. In some embodiments, the non-wild type or inserted amino acid is Arg. In some embodiments, the other (non-wild type or inserted) amino acid is Ala, Asn, Asp, Cys, Glu, Gln, Gly, His, Ile, Leu, Met, Phe, Pro, Ser, Thr, Trp, Tyr, or Val.

In some embodiments, the polypeptide conjugate described herein comprises a full length antibody heavy chain and an antibody light chain. In some embodiments, the acyl donor glutamine-containing tag is linked to/located at the polypeptide at the carboxyl terminus of a heavy chain, a light chain, or both the heavy chain and the light chain. For example, the acyl donor glutamine-containing tag GGLLQGPP (SEQ ID NO:13) is linked to the polypeptide at the carboxyl terminus of a light chain. In one variation, the acyl donor glutamine-containing tag GGLLQGPP (SEQ ID NO:13) is linked to the polypeptide comprising the Q295N mutation (EU numbering scheme) at the carboxyl terminus of a light chain. In another variation, the acyl donor glutamine-containing tag LLQGPA (SEQ ID NO:4), LLQGP (SEQ ID NO:5), or LLQGPP (SEQ ID NO:11) is linked to the polypeptide comprising the Q295N mutation at the carboxyl terminus of a heavy chain.

In some embodiments, the polypeptide described herein is a monoclonal antibody, a polyclonal antibody, a human antibody, a humanized antibody, a chimeric antibody, a bispecific antibody, a minibody, a diabody, or an antibody fragment.

In some embodiments, the antibody is an IgG. In some embodiments, the IgG is selected from the group consisting of IgG1, IgG2, IgG3, and IgG4.

In some embodiments, the antibody is an IgA, IgE, IgD, or IgM.

In some embodiments, the acyl donor glutamine-containing tag is located in the polypeptide by insertion or by replacement of one or more wild-type amino acid(s) at another site on the polypeptide described herein (e.g., Fc-containing polypeptide, Fab-containing polypeptide, or antibody), wherein the other site is not an amino or a carboxyl terminus. For example, the acyl donor glutamine-containing tag is part of an antibody loop. The acyl donor glutamine-containing tag can be linked to one or more heavy chain loop(s). The acyl donor glutamine-containing tag can also be linked to one or more light chain loop(s) of the antibody. In some embodiments, the acyl donor glutamine-containing tag is located at both a heavy chain and a light chain loops. In some embodiments, the another site is amino acid position(s) 108, 135, 160, 168, 189-192, 190-192, 200-202, 222-223, 251-254, 252-253, 222-223, 293-297, 294-297, 295, 297, or 385 (EU numbering scheme) of the human IgG1 antibody.

In some embodiments, the effector function (e.g., as measured by Fcγ3 and/or C1q binding) of the engineered polypeptide (e.g., Fc-containing polypeptide or antibody) conjugate described herein decreases no greater than about any of 1-fold, 2-fold, 3-fold, 4-fold, or 5-fold relative to a wild type polypeptide (e.g., Fc-containing polypeptide or antibody). In some embodiments, the engineered polypeptide conjugate is an IgG, wherein the effector function of the IgG decreases no greater than about 2-fold relative to a wild type IgG. In other embodiments, the effector function of the IgG decreases about 2-fold relative to a wild type IgG. In other embodiments, the effector function of the IgG decreases more than about 2-fold relative to a wild type IgG. In some embodiments, the engineered Fc-containing polypeptide conjugate is an IgG, wherein the effector function of the IgG decreases no greater than about 1-fold relative to a wild type IgG. In other embodiments, the effector function of the IgG decreases about 1-fold relative to a wild type IgG. In some embodiments, the effector function of the IgG decreases more than about any of 1-fold, 3-fold, 4-fold, or 5-fold relative to a wild type IgG.

In some embodiments, the effector function (e.g., as measured by Fcγ3 and/or C1q binding) of the engineered polypeptide (Fc-containing polypeptide or antibody) conjugate described herein increases at least about 1-fold to 3000-fold relative to a wild type polypeptide (e.g., Fc-containing polypeptide or antibody). In some embodiments, the effector function of the engineered polypeptide (e.g., Fc-containing polypeptide or antibody) conjugate increases at least about any of 1- to 5-fold, 6- to 10-fold, 11- to 15-fold, 16- to 20-fold, 21- to 25-fold, 26- to 30-fold, 31- to 35-fold, 36- to 40-fold, 41- to 45-fold, 46- to 50-fold, 51- to 55-fold, 56- to 60-fold, 61- to 65-fold, 66- to 70-fold, 71- to 75-fold, 76- to 80-fold, 81- to 85-fold, 86- to 90-fold, 91- to 95-fold, 96- to 100-fold, 101- to 200-fold, 201- to 300-fold, 301- to 500-fold, 501- to 1000-fold, 1001- to 1500-fold, 1501- to 2000-fold, 2001- to 2500-fold, 2501- to 3000-fold relative to a wild type polypeptide (e.g., Fc-containing polypeptide or antibody). In some embodiments, the engineered polypeptide conjugate is an IgG, wherein the effector function of the IgG increases about 1-fold to 300-fold relative to a wild type IgG. In some embodiments, the effector function of the IgG increases about any of 2-fold, 3-fold, 4-fold, 5-fold, 10-fold, 15-fold, 20-fold, 40-fold, 60-fold, 80-fold, 100-fold, 150-fold, 200-fold, 250-fold, 300-fold, 400-fold, 500-fold, 600-fold, 700-fold, 800-fold, 900-fold, 1000-fold, 1500-fold, 2000-fold, 2500-fold, or 3000-fold relative to a wild type IgG.

In some embodiments, the amine donor agent has the formula: X-Y-Z, wherein X is an amine donor unit; Y is a linker; and Z is an agent moiety.

The number of the amine donor agents which may be conjugated via the acyl donor glutamine-containing tag to the polypeptide (e.g., Fc-containing polypeptide, Fab-containing polypeptide, or antibody) is dependent on the number of acyl donor glutamine-containing tags which are linked/inserted to the polypeptide(s) as well as the number of Gln on the acyl donor glutamine-containing tag. For example, two amine donor agents may be site-specifically conjugated to an antibody at the carboxyl termini of the two heavy chains and/or two amine donor agents may be site-specifically conjugated to the same antibody at the carboxyl termini of the two light chains.

The amine donor unit of the present invention is a primary amine ($NH_2$) that provides a substrate for transglutaminase to allow conjugation of the agent moiety to the polypeptide via the acyl donor glutamine-containing tag. Accordingly, the linkage between the acyl donor glutamine-containing tag and the amine donor unit is of the formula $CH_2$—$CH_2$—CO—NH—, wherein NH— is linked to a linker and an agent moiety.

The linker of the present invention can be a cleavable or a non-cleavable linker. For example, the linker (with amine donor unit) or the amine donor agent can be released from the polypeptide. In some embodiments, the linker can be a peptide linker (e.g., conventional or nonconventional amino acid(s)) and/or a non-peptide linker. Examples of a non-peptide linker include an alkyl linker and a PEG linker.

In some embodiments, the amine donor unit-linker (e.g., X-Y) is a linear unit comprising an agent moiety. In other embodiments, the amine donor unit-linker is a branched unit (e.g., at least 2 units) comprising at least about 2, 3, 4, 5, 6, 7, 8, 9, 10, 11, 12, or more agent moieties.

Exemplary amine donor unit-linkers include, but are not limited to, Ac-Lys-Gly, aminocaproic acid, Ac-Lys-β-Ala, amino-PEG2-C2, amino-PEG3-C2, amino-PEG6-C2, Ac-Lys-Val-Cit (citrulline)-PABC (p-aminobenzyloxycarbonyl), aminocaproyl-Val-Cit-PABC, amino-PEG6-C2-Val-Cit-PABC, aminocaproyl-Val-Cit-PABC, [(3R,5R)-1-{3-(2-(2-aminoethoxy)ethoxy]propanoyl}piperidine-3 s-Val-Cit-PABC, [(3S,5S)-1-{3-[2-(2-aminoethoxy)ethoxy]propanoyl}piperidine-3,5-diyl]bis-Val-Cit-PABC-, Ac-Lys-putrescine, or 2-aminoethoxy.

The agent moiety of the engineered polypeptide of the present invention includes a small molecule, a protein or polypeptide, and a biocompatible polymer.

In some embodiments, a small molecule is a cytotoxic agent, an immunosuppressive agent, or an imaging agent (e.g., a fluorophore). In some embodiments, the cytotoxic agent is a chemotherapeutic agent.

Examples of a cytotoxic agent include, but are not limited to, an anthracycline, an auristatin, a camptothecin, a combretastatin, a dolastatin, a duocarmycin, an enediyne, a geldanamycin, an indolino-benzodiazepine dimer, a maytansine, a puromycin, a taxane, a *vinca* alkaloid, SN-38, a tubulysin, a hemiasterlin, a spliceostatin, a pladienolide, and stereoisomers, isosteres, analogs, or derivatives thereof.

The anthracyclines are derived from bacteria *Strepomyces* and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., *Antimicrob. Agents Chemother.* 42:2961-2965, 1998. Exemplary dolastatins and auristatins include, but are not limited to, dolastatin 10, auristatin E, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other novel auristatins (such as the ones described in U.S. Publication No. 2013/0129753). In some embodiments, the auristatin is 0101 (2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide) having the following structure:

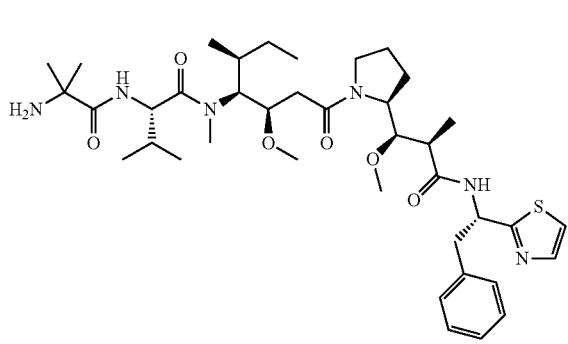

In some embodiments, the auristatin is 3377 (N,2-dimethylalanyl-N-{(1S,2R)-4-{(2S)-2-[(1R,2R)-3-{[(1S)-1-carboxyl-2-phenylethyl]amino}-1-methoxy-2-methyl-3-oxopropyl]pyrrolidin-1-yl}-2-methoxy-1-[(1 S)-1-methylpropyl]-4-oxobutyl}-N-methyl-L-valinamide) having the following structure:

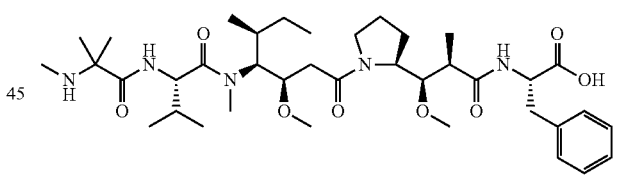

In other embodiments, the auristatin is 0131 (2-methyl-L-proly-N-[(3R,4S,5S)-1-{(2S)-2-[(1R,2R)-3-{[(1S)-1-carboxy-2-phenyl ethyl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

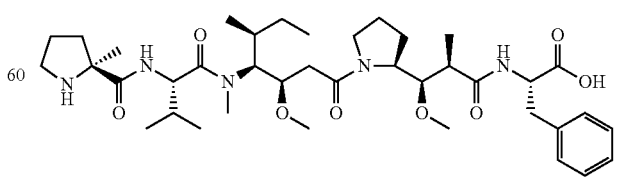

In other embodiments, the auristatin is 0121 (2-methyl-L-proly-N-[(3R,4S,5S)-1-{(2S)-2-[(1R,2R)-3-{[(2 S)-1- methoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

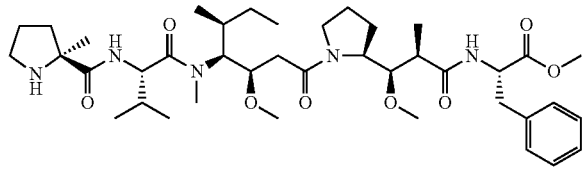 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@]1(C)CCCN1)C(C)C]

Camptothecin is a cytotoxic quinoline alkaloid which inhibits the enzyme topoisomerase I. Examples of camptothecin and its derivatives include, but are not limited to, topotecan and irinotecan, and their metabolites, such as SN-38.

Combretastatins are natural phenols with vascular disruption properties in tumors. Exemplary combretastatins and their derivatives include, but are not limited to, combretastatin A-4 (CA-4) and ombrabulin.

Duocarmycins are DNA alkylating agents with cytotoxic potency. See Boger and Johnson, *PNAS* 92:3642-3649 (1995). Exemplary duocarmycins include, but are not limited to, duocarmycin A, duocarmycin B1, duocarmycin B2, duocarmycin C1, duocarmycin C2, duocarmycin D, duocarmycin SA, and CC-1065.

Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, and dynemicin.

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethyl-aminoethylamino-17-demethoxygeldanamycin).

Hemiasterlin and its analogues (e.g., HTI-286) bind to the tubulin, disrupt normal microtubule dynamics, and, at stoichiometric amounts, depolymerize microtubules.

Maytansines or their derivatives maytansinoids inhibit cell proliferation by inhibiting the microtubules formation during mitosis through inhibition of polymerization of tubulin. See Remillard et al., *Science* 189:1002-1005 (1975). Exemplary maytansines and maytansinoids include, but are not limited to, mertansine (DM1) and its derivatives as well as ansamitocin.

Pyrrolobenzodiazepine dimers (PBDs) and indolino-benzodiazepine dimers (IGNs) are anti-tumor agents that contain one or more immine functional groups, or their equivalents, that bind to duplex DNA. PBD and IGN molecules are based on the natural product athramycin, and interact with DNA in a sequence-selective manner, with a preference for purine-guanine-purine sequences. Exemplary PBDs and their analogs include, but are not limited to, SJG-136.

Spliceostatins and pladienolides are anti-tumor compounds which inhibit splicing and interact with spliceosome, SF3b. Examples of spliceostatins include, but are not limited to, spliceostatin A, and FR901464. Examples of pladienolides include, but are not limited to, Pladienolide B, Pladienolide D, and E7107.

Taxanes are diterpenes that act as anti-tubulin agents or mitotic inhibitors. Exemplary taxanes include, but are not limited to, paclitaxel (e.g., TAXOL®) and docetaxel (TAXOTERE®).

Tubulysins are natural products isolated from a strain of myxobacteria that has been shown to depolymerize microtubules and induce mitotic arrest. Exemplary tubulysins include, but are not limited to, tubulysin A, tubulysin B, and tubulysin D.

*Vinca* alkyloids are also anti-tubulin agents. Exemplary vinca alkyloids include, but are not limited to, vincristine, vinblastine, vindesine, and vinorelbine.

In some embodiments, the agent moiety is an immunosuppressive agent. Examples of an immunosuppressive agent include, but are not limited to, gancyclovier, etanercept, tacrolimus, sirolimus, voclosporin, cyclosporine, rapamycin, cyclophosphamide, azathioprine, mycophenolgate mofetil, methotrextrate, and glucocorticoid and its analogs.

In some embodiments, the agent moiety is an imaging agent (e.g., a fluorophore or a chelator), such as fluorescein, rhodamine, lanthanide phosphors, and their derivatives thereof. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101). Examples of chelators include, but are not limited to, 1,4,7,10-tetraazacyclododecane-N,N',N'',N'''-tetraacetic acid (DOTA), 1,4,7-triazacyclononane-1,4,7-triacetic acid (NOTA), 1,4,7-triazacyclononane, 1-glutaric acid-4,7-acetic acid (NODAGA), diethylenetriaminepentaacetic acid (DTPA), and 1,2-bis(o-aminophenoxy)ethane-N,N,N',N'-tetraacetic acid) (BAPTA).

In some embodiments, the agent moiety is a polypeptide. In some embodiments, the polypeptide is an antibody, such as a humanized, human, chimeric, or murine monoclonal antibody.

In some embodiments, the agent moiety is a toxin polypeptide (or a toxin protein). Examples of a toxin polypeptide include, but are not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, tricothecenes, inhibitor cystine knot (ICK) peptides (e.g., ceratotoxins), and conotoxin (e.g., KIIIA or SmIIIa).

In some embodiments, therapeutic radioisotopes or other labels can be incorporated in the agent moiety (e.g., by binding to a chelator) for conjugation of a polypeptide (e.g., a Fc-containing or Fab-containing polypeptide) to an amine donor agent that bears a chelator. Examples of a radioisotope or other labels include, but are not limited to, $^{3}$H, $^{14}$C, $^{15}$N, $^{35}$S, $^{18}$F, $^{32}$P, $^{33}$P, $^{64}$Cu, $^{68}$Ga, $^{89}$Zr, $^{90}$Y, $^{99}$Tc, $^{123}$I, $^{124}$I, $^{125}$I, $^{131}$I, $^{111}$In, $^{131}$In, $^{153}$Sm, $^{186}$Re, $^{188}$Re, $^{211}$At, $^{212}$Bi, and $^{153}$Pb.

In some embodiments, the agent moiety is a biocompatible polymer. The polypeptide can be conjugated to the biocompatible polymer via the acyl donor glutamine-containing tag to improve the biological characteristics of the polypeptide, e.g., to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

In some embodiments, the amine donor agent (X-Y-Z) is

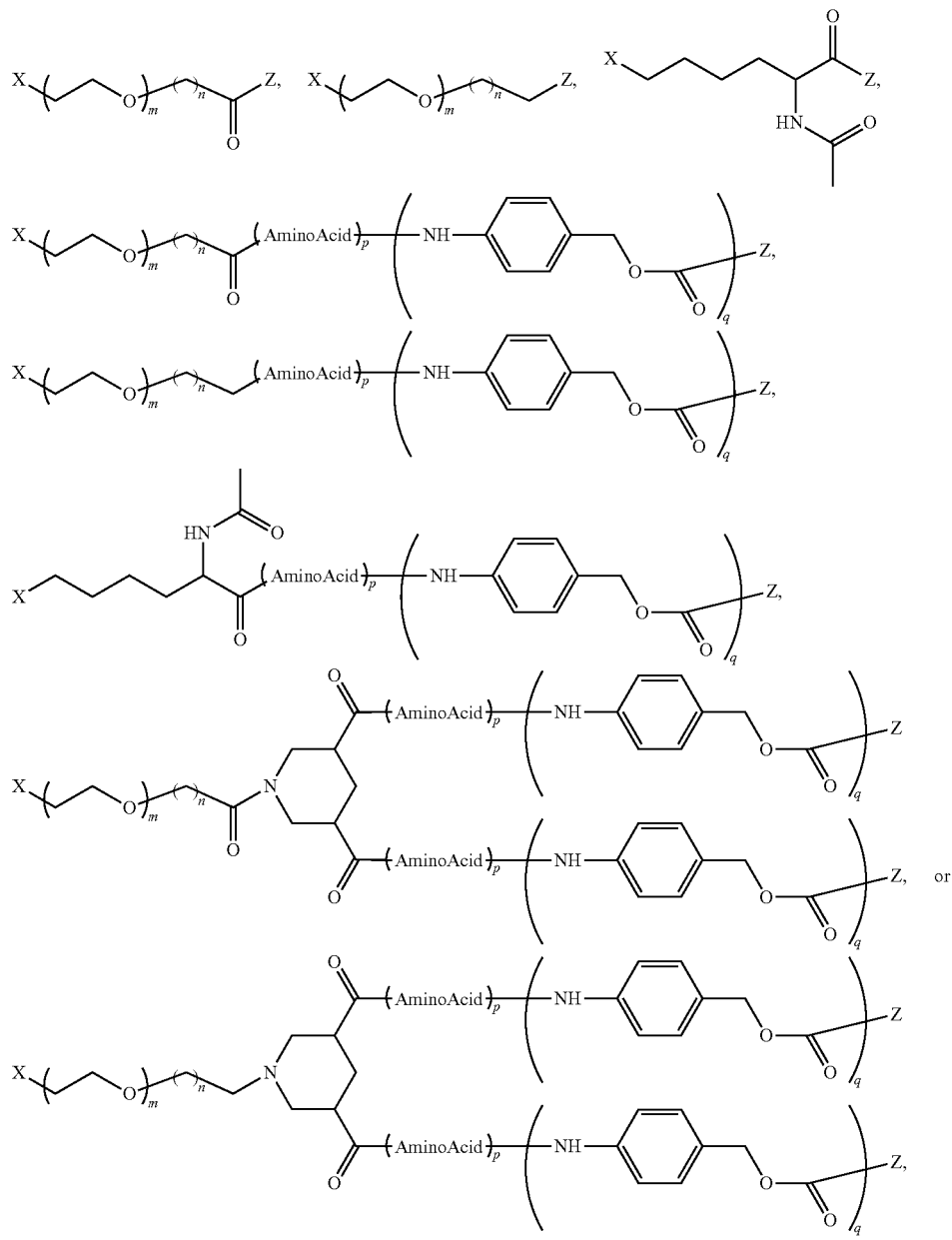

wherein X is $NH_2$ (i.e., thus forming a covalent bond with glutamine as $CH_2$—$CH_2$—CO—NH—), m is a 0 to 20, n is 1 to 8, p is 0 to 3, q is 0 or 1, amino acid is any conventional or nonconventional amino acid and Z is a cytotoxic agent or an imaging agent.

Conventional or naturally occurring amino acids are divided into groups based on common side-chain properties: (1) non-polar: Norleucine, Met, Ala, Val, Leu, Ile; (2) polar without charge: Cys, Ser, Thr, Asn, Gln; (3) acidic (negatively charged): Asp, Glu; (4) basic (positively charged): Lys, Arg; and (5) residues that influence chain orientation: Gly, Pro; and (6) aromatic: Trp, Tyr, Phe, His. Conventional amino acids include L or D stereochemistry.

Unconventional amino acids are non-naturally occurring amino acids. Examples of an unconventional amino acid include, but are not limited to, aminoadipic acid, beta-alanine, beta-aminopropionic acid, aminobutyric acid, piperidinic acid, aminocaprioic acid, aminoheptanoic acid, aminoisobutyric acid, aminopimelic acid, citrulline, diaminobutyric acid, desmosine, diaminopimelic acid, diaminopropionic acid, N-ethylglycine, N-ethylaspargine, hyroxylysine, allo-hydroxylysine, hydroxyproline, isodesmosine, allo-isoleucine, N-methylglycine, sarcosine, N-methylisoleucine, N-methylvaline, norvaline, norleucine, orithine, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and amino acids (e.g., 4-hydroxyproline).

In some embodiments, the amine donor agent is selected from the group consisting of Alexa 488 cadaverine, 5-FITC cadaverine, Alexa 647 cadaverine, Alexa 350 cadaverine, 5-TAMRA cadaverine, 5-FAM cadaverine, SR101 cadaverine, 5,6-TAMRA cadaverine, 5-FAM lysine, Ac-Lys-Gly-MMAD, amino-PEG3-C2-MMAD, amino-PEG6-C2-MMAD, amino-PEG3-C2-amino-nonanoyl-MMAD, aminocaproyl-Val-Cit-PABC-MMAD, Ac-Lys-β-Ala-MMAD, Aminocaproyl-MMAD, amino-PEG6-C2-Val-Cit-PABC-MMAD, Ac-Lys-Val-Cit-PABC-MMAD, Ac-Lys-Val-Cit-PABC-0101, amino-PEG3-C2-Val-Cit-PABC-MMAD, amino-PEG3-C2-Val-Cit-PABC-MMAD, amino-PEG6-C2-Val-Cit-PABC-0101, aminocaproyl-MMAE, amino-PEG3-C2-MMAE, amino-PEG2-C2-MMAE, aminocaproyl-MMAF, aminocaproyl-Val-Cit-PABC-MMAE, amino-PEG6-C2-Val-Cit-PABC-MMAF, aminocaproyl-Val-Cit-PABC-MMAF, amino-PEG2-C2-MMAF, amino-PEG3-C2-MMAF, putrescinyl-geldanamycin, Ac-Lys-putrescinyl-geldanamycin, aminocaproyl-3377, aminocaproyl-0131, amino-PEG6-C2-0131, amino-PEG6-C2-3377, aminocaproyl-0121, amino-PEG6-C2-0121, [(3R,5R)-1-{3-[2-(2-aminoethoxy)ethoxy]propanoyl}piperidine-3,5-diyl] bis-Val-Cit-PABC-MMAD, [(3R,5R)-1-{3-[2-(2-aminoethoxy)ethoxy]propanoyl}piperidine-3,5-diyl]bis-Val-Cit-PABC-MMAE, and 2-aminoethoxy-PEG6-NODAGA (or 2,2'-(7-(1-amino-28-carboxy-25-oxo-3,6,9,12,15,18,21-heptaoxa-24-azaoctacosan-28-yl)-1,4,7-triazonane-1,4-diyl) diacetic acid). In some embodiments, the acyl donor glutamine-containing tag comprises the amino acid sequence LLQGPA (SEQ ID NO:4), LLQGP (SEQ ID NO:5), LLQGPP (SEQ ID NO:11), or GGLLQGPP (SEQ ID NO:13) and the amine donor agent is Ac-Lys-Val-Cit-PABC-MMAD, Ac-Lys-Val-Cit-PABC-0101, or amino-PEG6-C2-MMAD. Exemplary structures of the amine donor agent are listed in Table 1.

TABLE 1
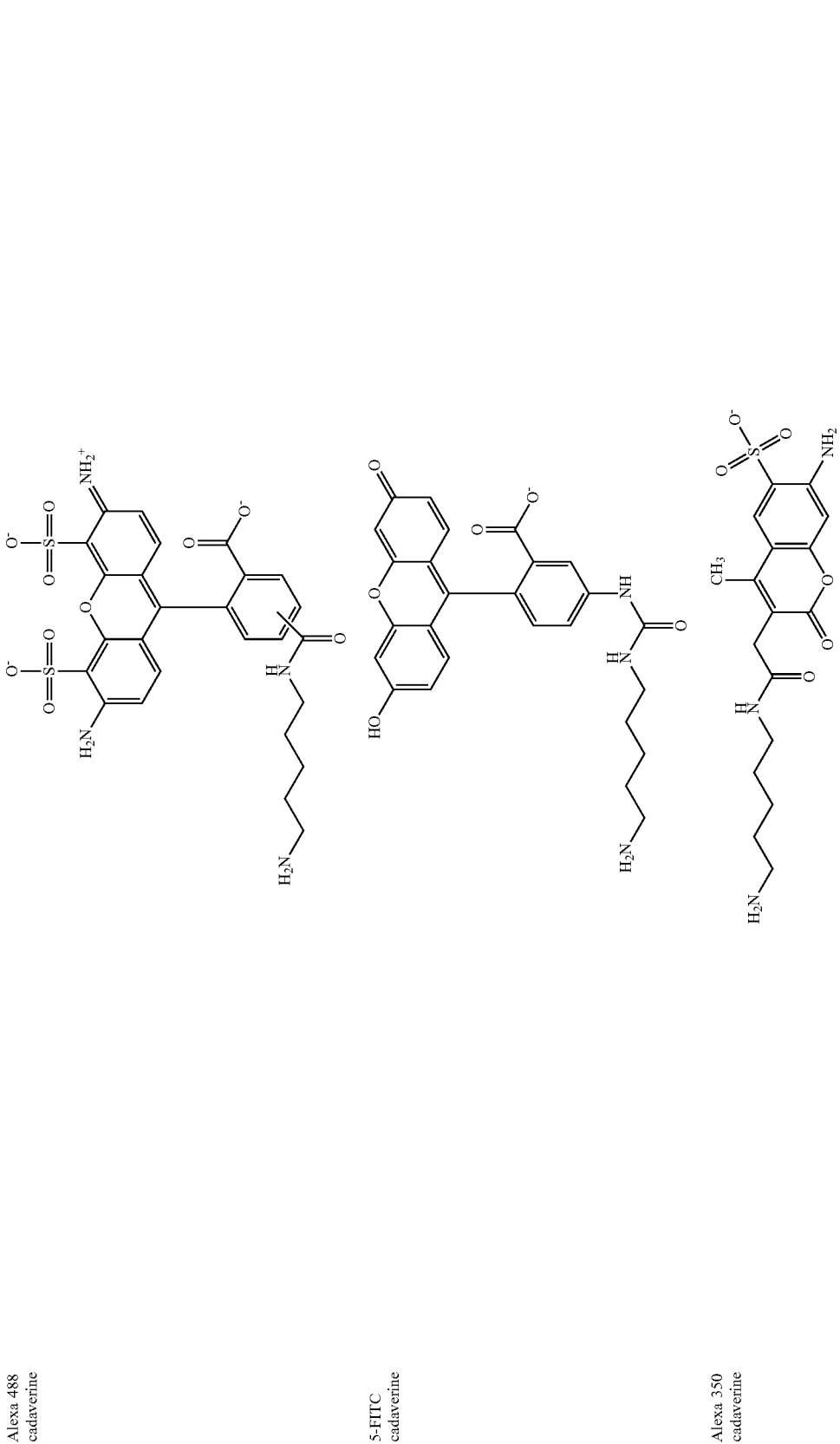

TABLE 1-continued
| | |
|---|---|
| 5-TAMRA cadaverine | 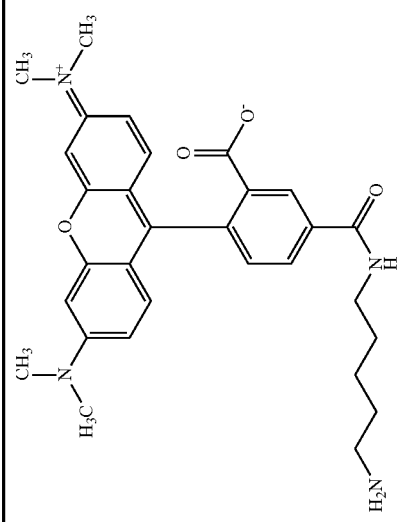 |
| 5-FAM cadaverine | 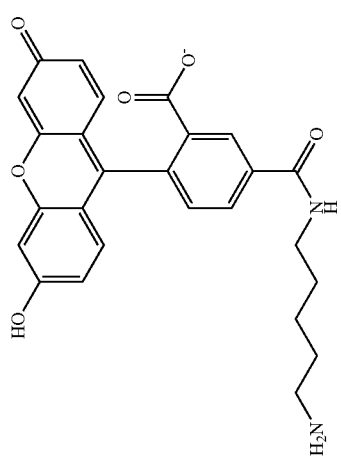 |

TABLE 1-continued
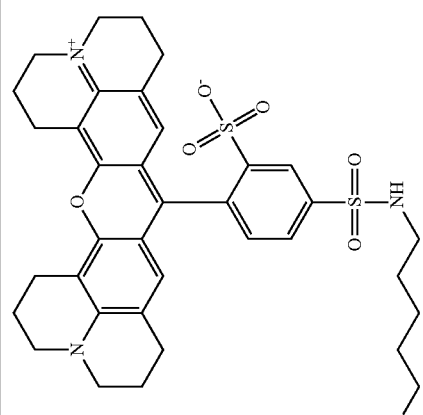
SR101 cadaverine
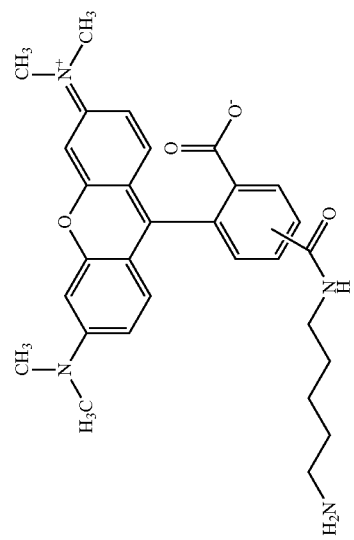
5,6-TAMRA cadaverine

TABLE 1-continued
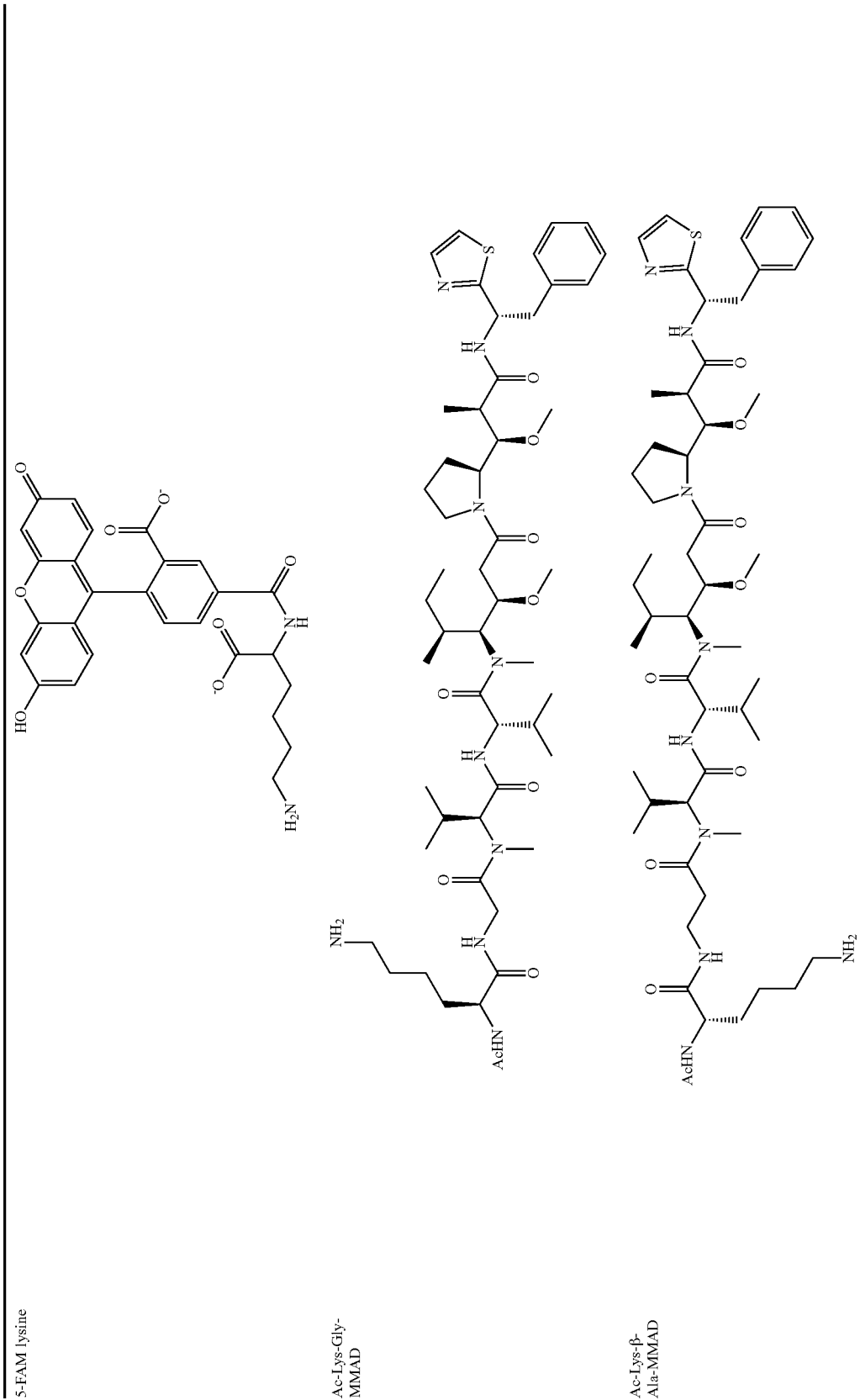
5-FAM lysine
Ac-Lys-Gly-MMAD
Ac-Lys-β-Ala-MMAD

TABLE 1-continued
| | |
|---|---|
| Aminocaproyl-MMAD | 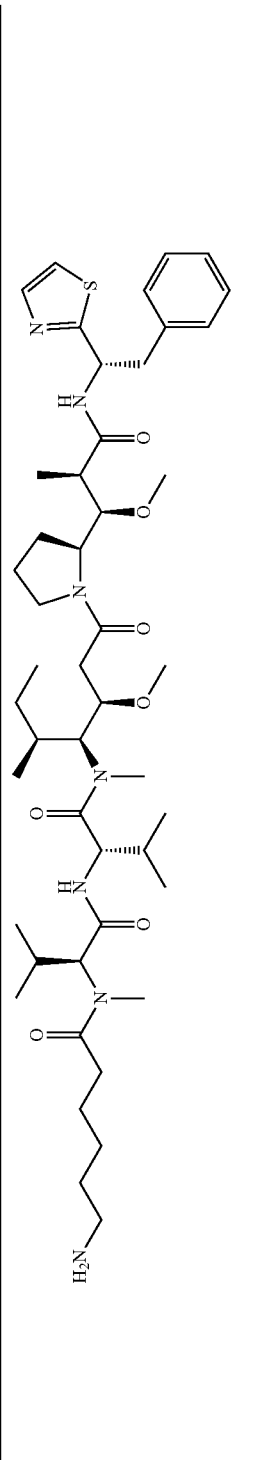 |
| Ac-Lys-Val-Cit-PABC-MMAD | 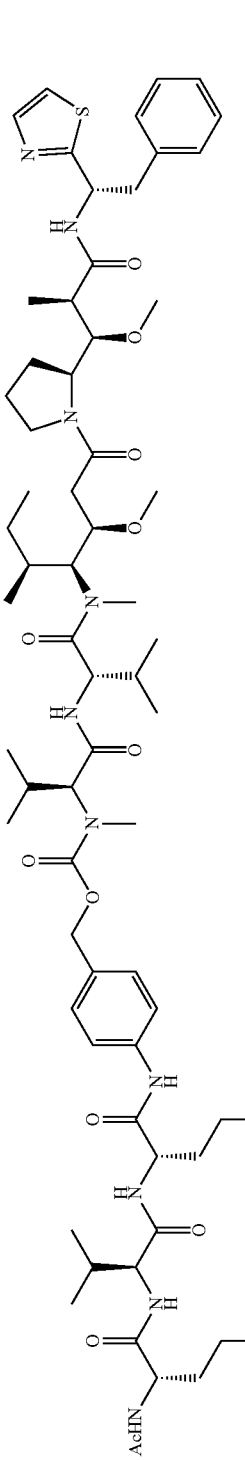 |
| Aminocaproyl-MMAE | 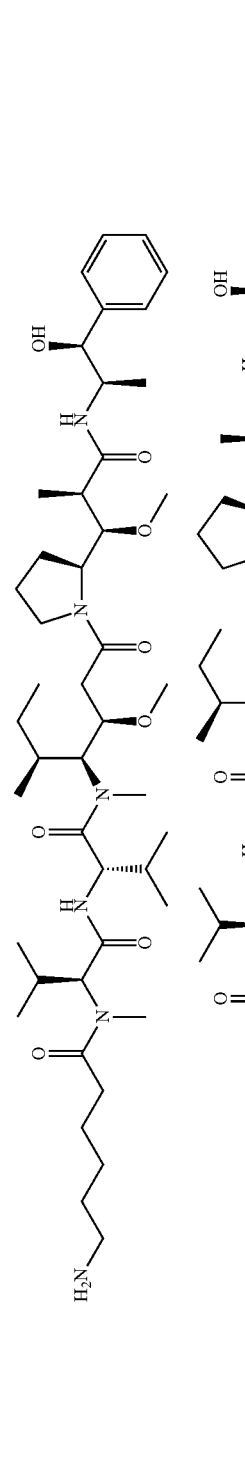 |
| Amino-PEG2-C2-MMAE (or Amino-PEG2-Propionyl-MMAE) | 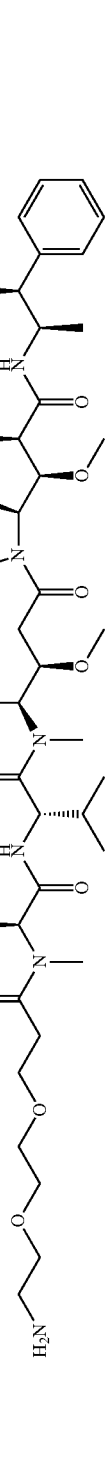 |

TABLE 1-continued
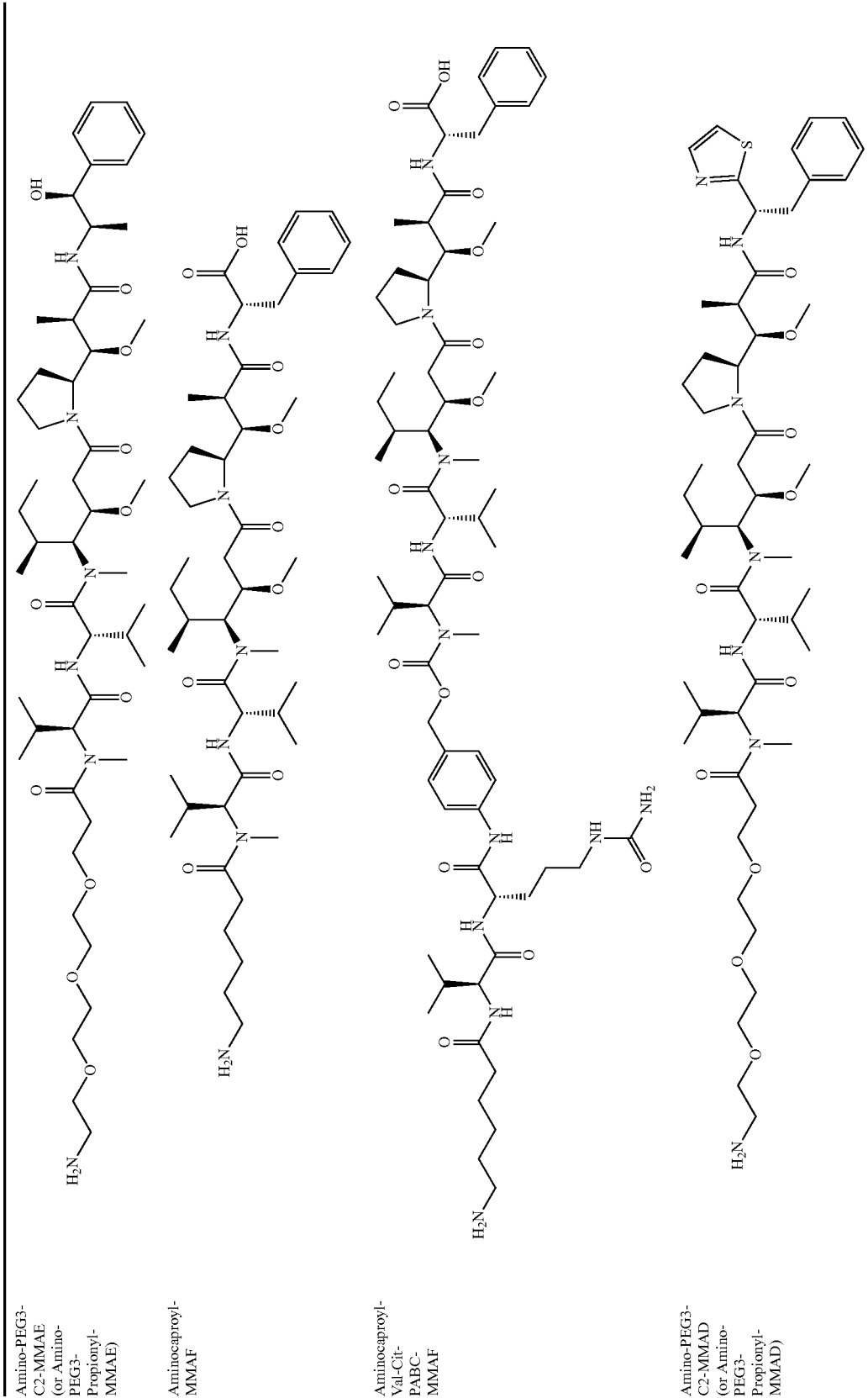

TABLE 1-continued
| | |
|---|---|
| Amino-PEG6-C2-MMAD (or Amino-PEG6-Propionyl-MMAD) | 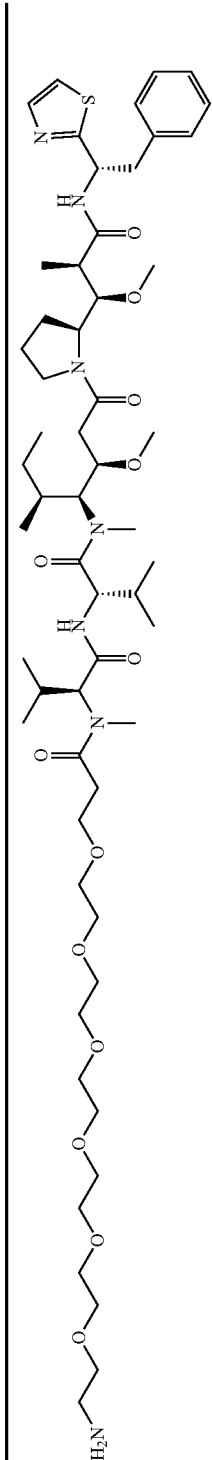 |
| Amino-PEG3-C2-amino-nonanoyl-MMAD (or Amino-PEG3-Propionyl-amino-nonanoyl-MMAD) | 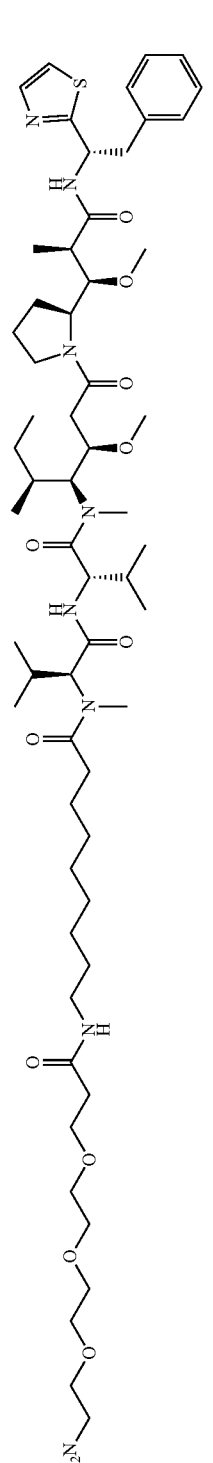 |
| Amino-nonanoyl-MMAD | 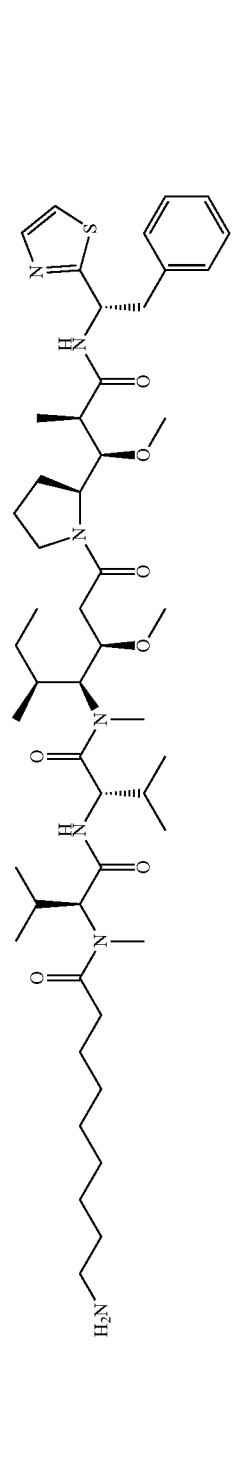 |
| Putrescinyl-Geldanamycin | 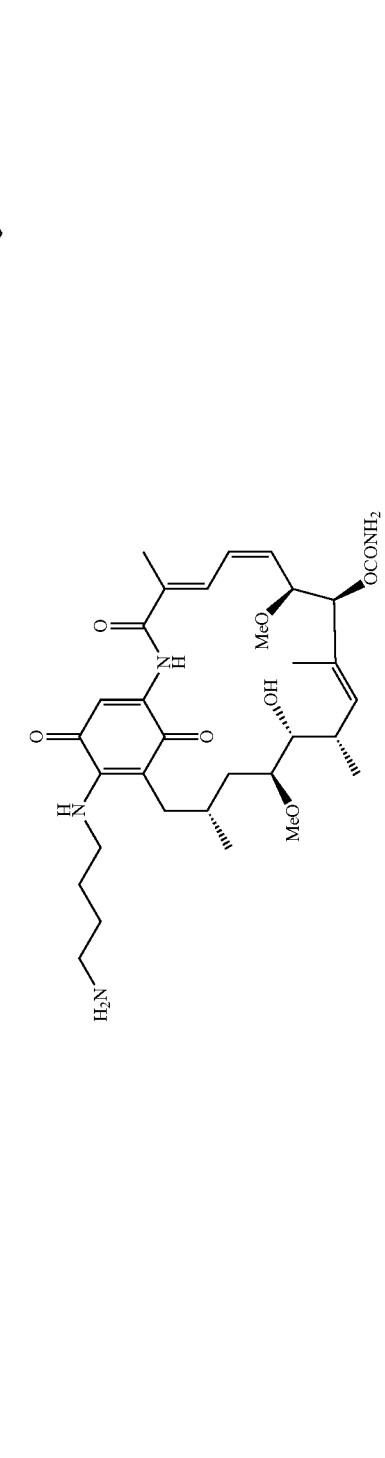 |

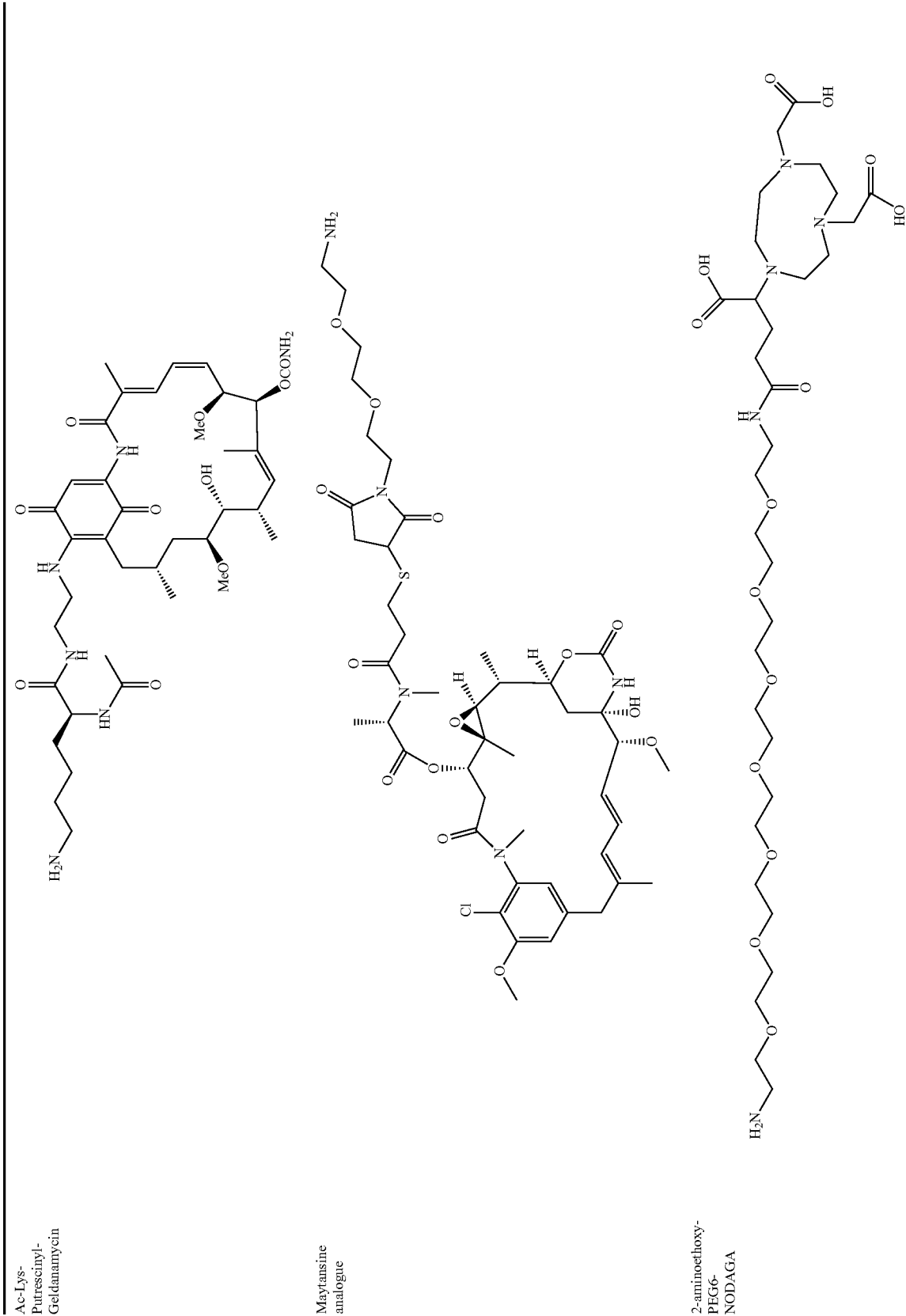

TABLE 1-continued
| | | | |
|---|---|---|---|
| 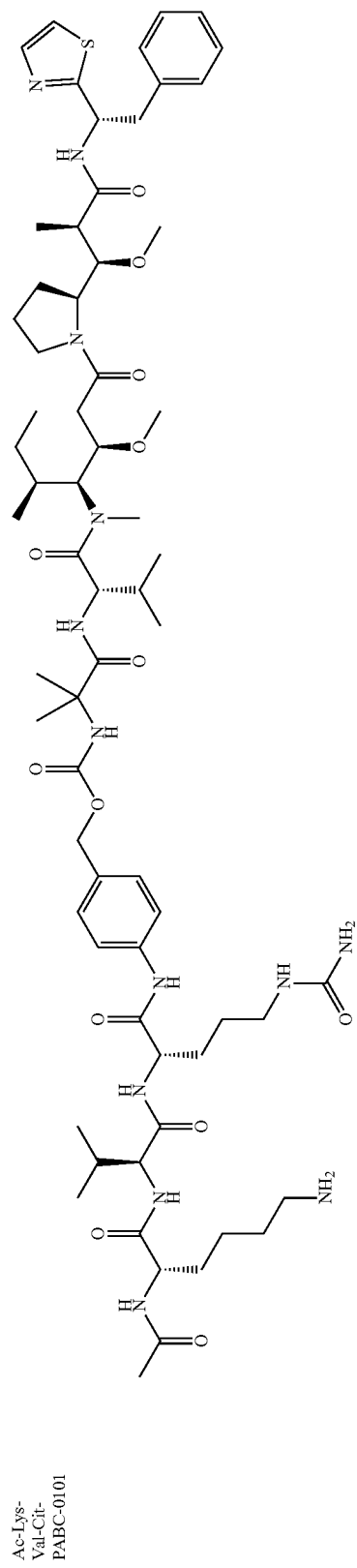 | 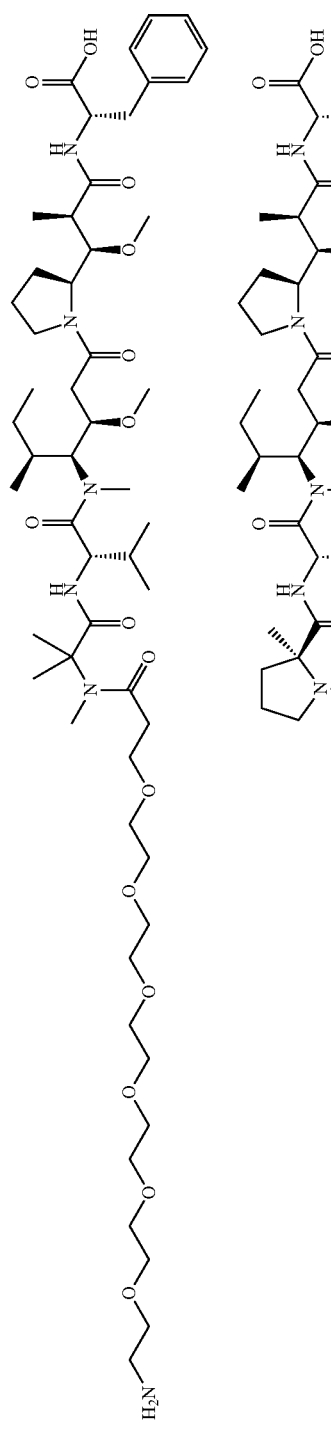 | 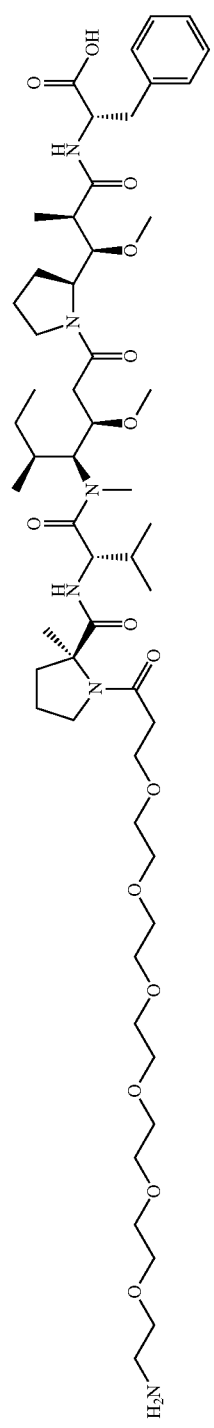 | 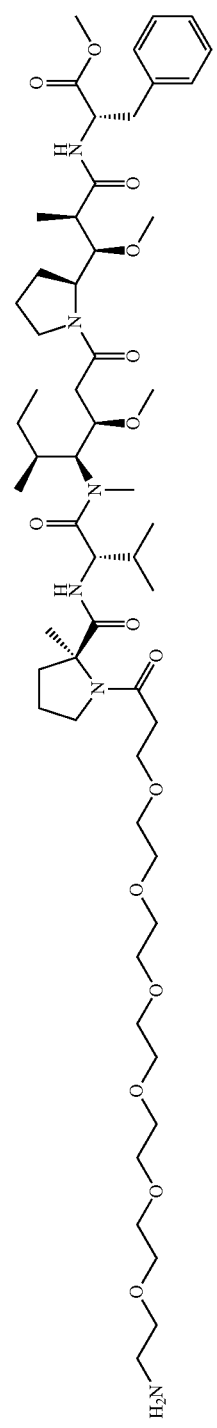 |
| Ac-Lys-Val-Cit-PABC-0101 | Amino-PEG6-C2-3377 | Amino-PEG6-C2-0131 | Amino-PEG6-C2-0121 |

TABLE 1-continued
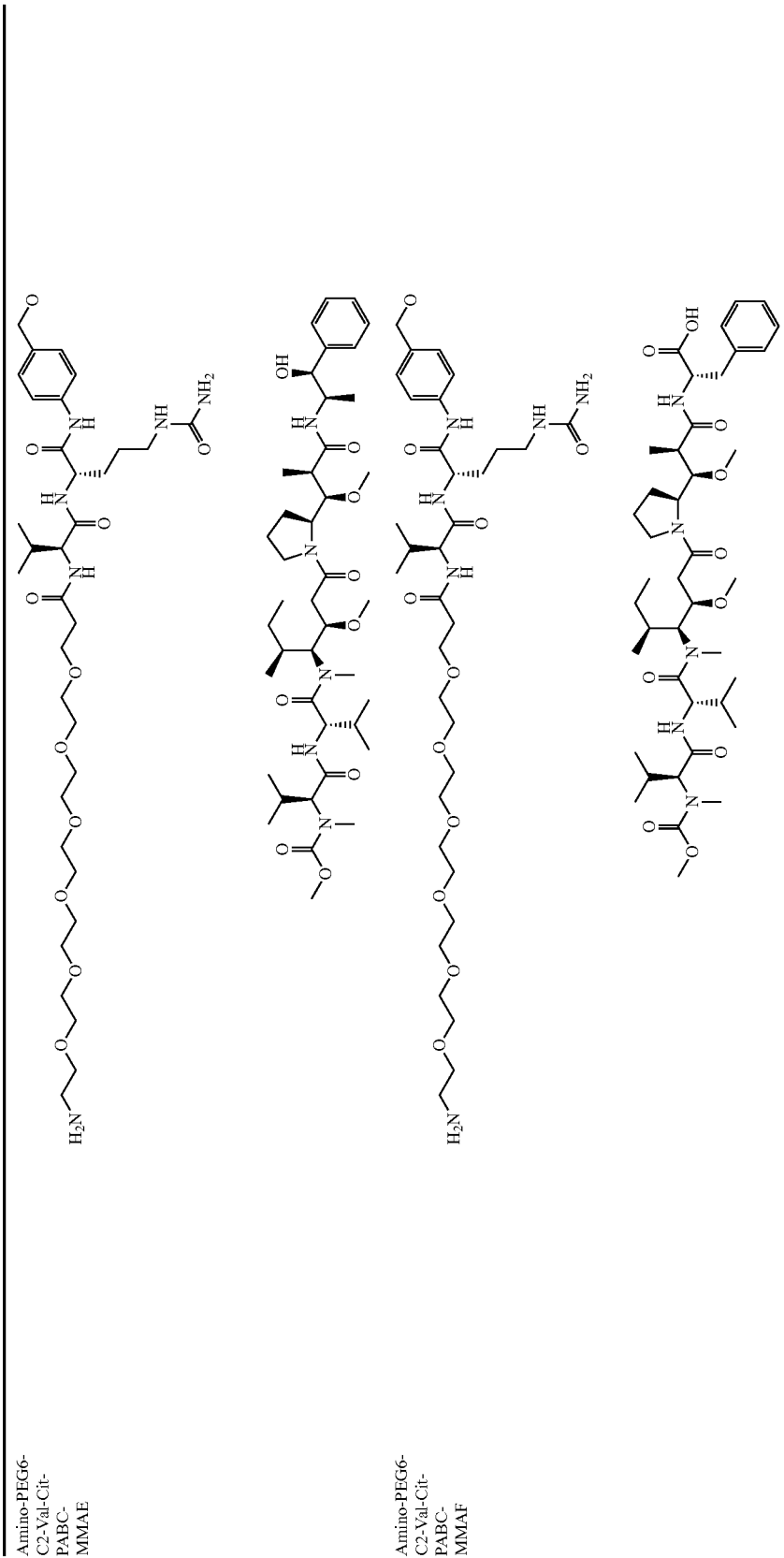
Amino-PEG6-C2-Val-Cit-PABC-MMAE
Amino-PEG6-C2-Val-Cit-PABC-MMAF TABLE 1-continued
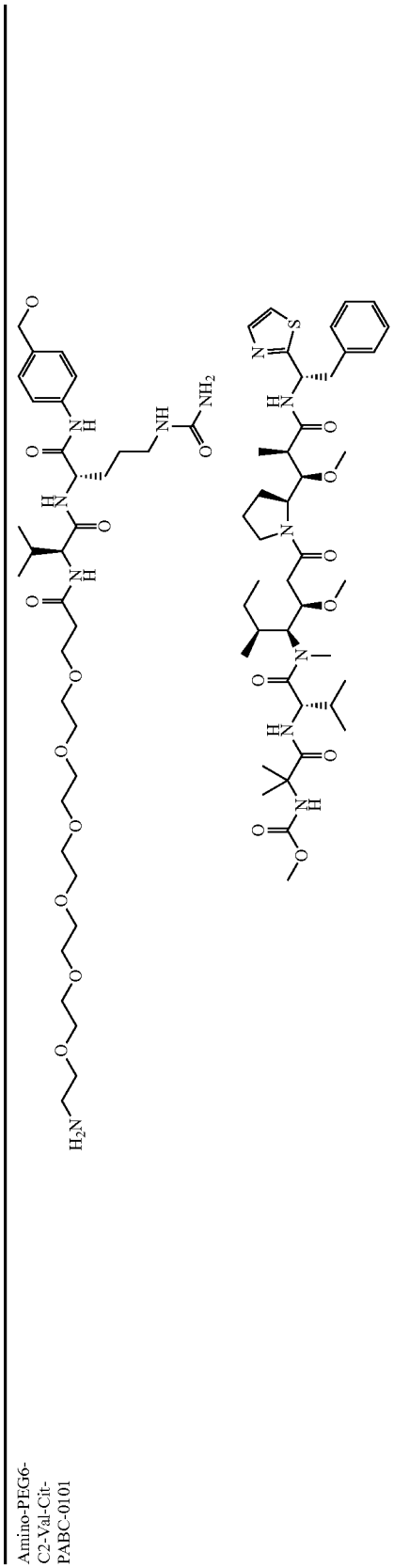
Amino-PEG6-C2-Val-Cit-PABC-0101

TABLE 1-continued
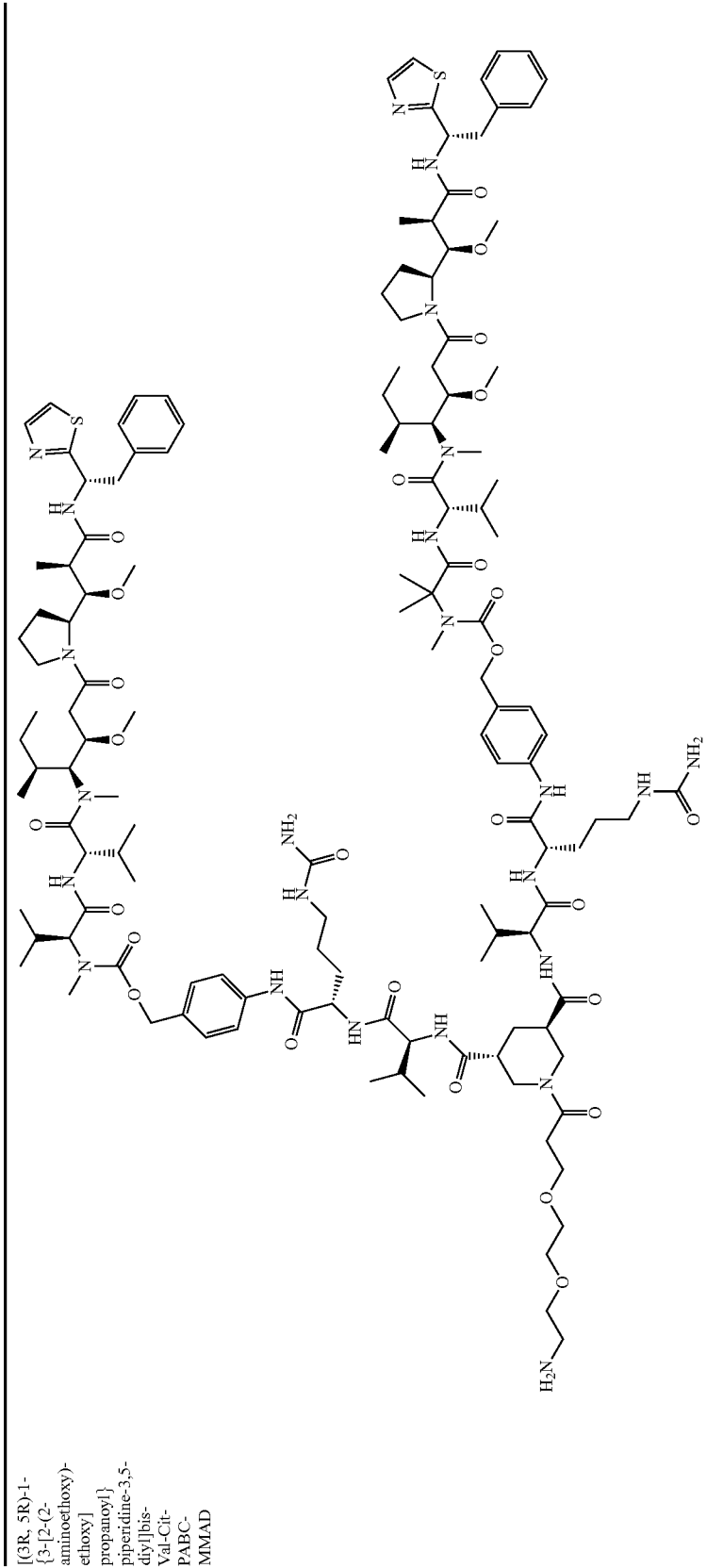
[(3R, 5R)-1-
{3-[2-(2-
aminoethoxy]
ethoxy]
propanoyl}
piperidine-3,5-
diyl]bis-
Val-Cit-
PABC-
MMAD

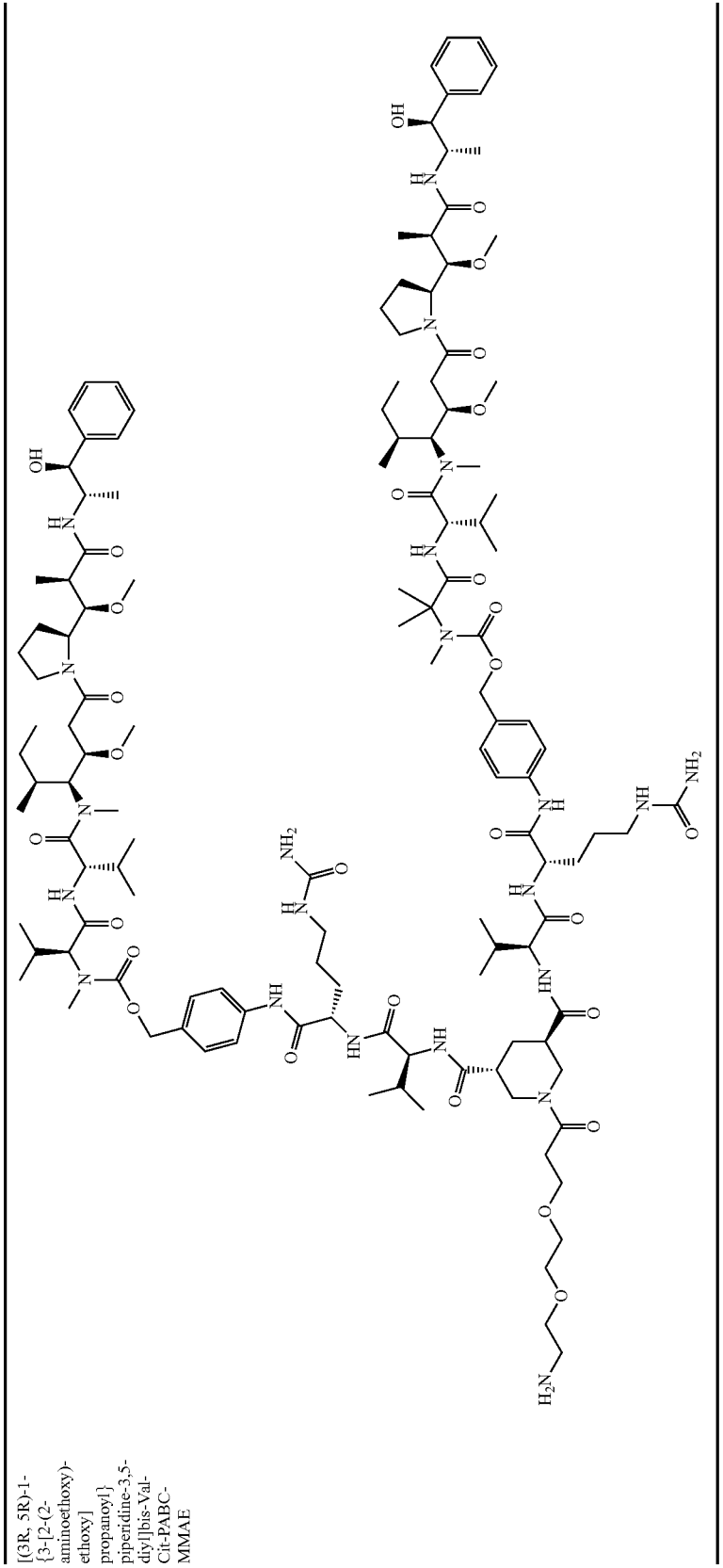
[(3R, 5R)-1-{3-[2-(2-aminoethoxy)ethoxy]propanoyl}piperidine-3,5-diyl]bis-Val-Cit-PABC-MMAE In another aspect, the invention provides an engineered toxin polypeptide conjugate comprising the formula: (toxin polypeptide)-T-A, wherein T is an acyl donor glutamine-containing tag engineered at a specific site, wherein A is an amine donor agent, wherein the amine donor agent is a biocompatible polymer comprising a reactive amine, wherein the biocompatible polymer is site-specifically conjugated to the acyl donor glutamine-containing tag at a carboxyl terminus, an amino terminus, or elsewhere at an another site in the toxin polypeptide, and wherein the acyl donor glutamine-containing tag comprises an amino acid sequence LLQGPX, wherein X is A or P (SEQ ID NO:14), or GGLLQGPP (SEQ ID NO:13). For example, the toxin polypeptide can be site-specifically conjugated to the biocompatible polymer via the acyl donor glutamine-containing tag as described herein to improve the biological characteristics of the toxin polypeptide, e.g., to increase the serum half-life and bioactivity, and/or to extend its in vivo half-lives. In some embodiments, toxin polypeptide is a cerato-toxin or a conotoxin (e.g., KIIIA or SmIIIa). In some embodiments, the biocompatible polymer is a water soluble polymer such as PEG derivative or a zwitterion-containing biocompatible polymer.

Methods for Making the Engineered Polypeptide Conjugates

The methods for making the engineered polypeptide conjugates described herein are also provided in the present invention. In one aspect, the invention provides a method for preparing an engineered polypeptide conjugate comprising the formula: polypeptide-T-A, wherein T is an acyl donor glutamine-containing tag engineered at a specific site, wherein A is an amine donor agent, and wherein the amine donor agent is site-specifically conjugated to the acyl donor glutamine-containing tag at a carboxyl terminus, an amino terminus, or elsewhere at an another site in the polypeptide, and wherein the acyl donor glutamine-containing tag comprises an amino acid sequence LLQGPX, wherein X is A or P (SEQ ID NO:14), or GGLLQGPP (SEQ ID NO:13), comprising the steps of: a) providing an engineered polypeptide-T molecule comprising the polypeptide and the acyl donor glutamine-containing tag; b) contacting the amine donor agent with the engineered polypeptide-T molecule in the presence of a transglutaminase; and c) allowing the engineered polypeptide-T to covalently link to the amine donor agent to form the engineered polypeptide conjugate. In some embodiments, the polypeptide is a Fc-containing or Fab-containing polypeptide, or an antibody. In some embodiments, the engineered polypeptide-T molecule is expressed in CHO cells.

In another aspect, the invention provides a method for preparing an engineered Fc-containing polypeptide conjugate comprising the formula: (Fc-containing polypeptide)-T-A, wherein T is an acyl donor glutamine-containing tag engineered at a specific site; wherein A is an amine donor agent; and wherein the amine donor agent is site-specifically conjugated to the acyl donor glutamine-containing tag at a carboxyl terminus, an amino terminus, or elsewhere at an another site in the Fc-containing polypeptide, wherein the acyl donor glutamine-containing tag comprises an amino acid sequence XXQX (SEQ ID NO: 35), wherein X is any amino acid (e.g., X can be the same or a different amino acid), and wherein the engineered Fc-containing polypeptide conjugate comprises an amino acid substitution from glutamine to asparagine at position 295 (e.g., Q295N; EU numbering scheme), comprising the steps of: a) providing an engineered (Fc-containing polypeptide)-T molecule comprising the Fc-containing polypeptide and the acyl donor glutamine-containing tag; b) contacting the amine donor agent with the engineered (Fc-containing polypeptide)-T molecule in the presence of a transglutaminase; and c) allowing the engineered (Fc-containing polypeptide)-T to covalently link to the amine donor agent to form the engineered Fc-containing polypeptide conjugate. In some embodiments, the engineered (Fc-containing polypeptide)-T is expressed in CHO cells. In some embodiments, the acyl donor glutamine-containing tag comprises an amino acid sequence selected from the group consisting of LLQGG (SEQ ID NO:16), LLQG (SEQ ID NO:17), LSLSQG (SEQ ID NO:18), GGGLLQGG (SEQ ID NO:19), GLLQG (SEQ ID NO:20), LLQ, GSPLAQSHGG (SEQ ID NO:21), GLLQGGG (SEQ ID NO:22), GLLQGG (SEQ ID NO:23), GLLQ (SEQ ID NO:24), LLQLLQGA (SEQ ID NO:25), LLQGA (SEQ ID NO:26), LLQYQGA (SEQ ID NO:27), LLQGSG (SEQ ID NO:28), LLQYQG (SEQ ID NO:29), LLQLLQG (SEQ ID NO:30), SLLQG (SEQ ID NO:31), LLQLQ (SEQ ID NO:32), LLQLLQ (SEQ ID NO:33), LLQGR (SEQ ID NO:34), LLQGPP (SEQ ID NO:11), LLQGPA (SEQ ID NO:4), GGLLQGPP (SEQ ID NO:13), GGLLQGA (SEQ ID NO:12), LLQGA (SEQ ID NO:1), LLQGPGK (SEQ ID NO:2), LLQGPG (SEQ ID NO:3), LLQGP (SEQ ID NO:5), LLQP (SEQ ID NO:6), LLQPGK (SEQ ID NO:7), LLQAPGK (SEQ ID NO:8), LLQGAPG (SEQ ID NO:9), and LLQGAP (SEQ ID NO:10). In some embodiments, the acyl donor glutamine-containing tag comprises an amino acid sequence LLQGPA (SEQ ID NO:4), LLQGP (SEQ ID NO:5), LLQGPP (SEQ ID NO:11), or GGLLQGPP (SEQ ID NO:13).

In some embodiments, the engineered polypeptide conjugate prepared using the methods described herein has conjugation efficiency of at least about 51%. In some embodiments, the engineered polypeptide conjugate has conjugation efficiency of at least about any of 51%-60%, 61%-70%, 71%-80%, 81%-90%, or 91%-100%. In some embodiments, the engineered polypeptide conjugate has conjugation efficiency of about any of 55%, 60%, 65%, 70%, 75%, 80%, 85%, 90%, 91%, 92%, 93%, 94%, 95%, 96%, 97%, 98%, 99%, 99.5%, 99.6%, 99.7%, 99.8%, 99.9%, or 100%. For example, the engineered polypeptide (e.g., Fc-containing polypeptide) comprising the Q295N mutation (EU numbering scheme) has conjugation efficiency of at least about 99.8%.

In some embodiments, the concentration ratio between the amine donor agent contacted and the engineered polypeptide-T molecule contacted is from about 2:1 to about 800:1. For example, the concentration ratio between the amine donor agent (e.g., a cytotoxic drug) and the engineered polypeptide attached to an acyl donor glutamine-containing tag loaded or used for the transglutaminase-catalyzed conjugation reaction can be about 20:1. In some embodiments, the concentration ratio between the amine donor agent contacted and the engineered polypeptide-T molecule contacted is about any of 2:1, 3:1, 4:1, 5:1, 6:1, 7:1, 8:1, 9:1, 10:1, 15:1, 20:1, 25:1, 30:1, 35:1, 40:1, 45:1, 50:1, 60:1, 70:1, 80:1, 90:1, 100:1, 200:1, 300:1, 400:1, 500:1, 600:1, 700:1, or 800:1.

In some embodiments, when a polypeptide (e.g., antibody) is conjugated with an amine donor agent via an acyl donor glutamine-containing tag at a specific site (e.g., C-terminus), the antibody-drug-conjugate is more stable (e.g., longer in vivo half-life). Accordingly, in some embodiments, the engineered polypeptide conjugate as described herein is present in a subject (e.g., a mammal) at least about 50% after at least about 1 day in vivo. For example, the engineered polypeptide conjugate is present in a subject at at least about any of 20%, 25%, 30%, 35%, 40%, 45%, 50%, 55%, 60%, 65%, 70%, 75%, 80%, 85%, 90%, or 95% after at least about any of 2 hours, 2-6 hours, 6-12 hours, 12-18 hours, 18-24 hours, 1 day, 2 days, 3 days, 4 days, 5 days, 6 days, 1 week, or 2 weeks in vivo.

In some embodiments, the methods provided herein further comprise a purification step. The engineered Fc-containing polypeptide conjugates described herein can be purified using various purification methods, such as, e.g., hydroxylapatite chromatography; dialysis; affinity chromatography; hydrophobic interaction chromatography (HIC) (e.g, fractionation on a HIC); ammonium sulphate precipitation; polyethylene glycol or polyethylene glycol derivative precipitation, anion or cation exchange chromatography; reverse phase HPLC; chromatography on silica; chromatofocusing; SDS-PAGE, gel filtration, size exclusion chromatography, and weak partitioning chromatography.

In some embodiments, at least one purification step comprises a step of affinity chromatography method. Protein A ligand (synthetic, recombinant, or native) may be used to affinity purify the engineered Fc-containing polypeptide conjugates described herein. Synthetic or recombinant Protein A ligand may be purchased commercially from GE Healthcare (Piscataway, N.J.), Pierce (Rockford, Ill.), Sigma-Aldrich (St. Louis, Mo.), or Applied Biosystems (Foster City, Calif.), and native Protein A ligand (e.g., MABSELECT™, PROSEP™ Va, and PROSEP™ Ultra Plus) may be purchased commercially from GE Healthcare (Piscataway, N.J.) or Millipore (Billerica, Mass.).

In some embodiments, the purified engineered Fc-containing polypeptide conjugate, the purified engineered Fab-containing polypeptide conjugate, or the purified toxin polypeptide conjugates resulting from the purification step is highly pure, i.e., at least about any of 70%-75%, 75%-80%, 80%-85%, 85%-90%, 90%-95%, 95%-98%, or 99% pure. For example, the purified engineered polypeptide conjugate is about any of 80%, 85%, 90%, 91%, 92%, 93%, 94%, 95%, 96%, 97%, 98%, or 99% pure.

Methods of Using the Engineered Polypeptide Conjugates

The engineered polypeptide conjugates of the present invention are useful in various applications including, but are not limited to, therapeutic treatment methods and diagnostic treatment methods.

In one aspect, the invention provides a method for treating a cancer in a subject. Accordingly, in some embodiments, provided is a method of treating a cancer in a subject in need thereof comprising administering to the subject an effective amount of a composition (e.g., pharmaceutical composition) comprising the engineered polypeptide conjugates as described herein. As used herein, cancers include, but are not limited to, a solid cancer (such as bladder, breast, cervical, choriocarcinoma, colon, esophageal, gastric, glioblastoma, head and neck, kidney, liver, lung (e.g., Non Small Cell Lung Cancer (NSCLC)), oral, ovarian, pancreatic, prostate, and skin cancer); and a liquid cancer (such as acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, and adult T-cell leukemia).

In some embodiments, provided is a method of inhibiting tumor growth or progression in a subject in need thereof, comprising administering to the subject an effective amount of a composition comprising the engineered polypeptide conjugates as described herein. In other embodiments, provided is a method of inhibiting metastasis of cancer cells or tumors (e.g., solid or liquid tumors) in a subject in need thereof, comprising administering to the subject an effective amount of a composition comprising the engineered polypeptide conjugates as described herein. In other embodiments, provided is a method of inducing tumor regression in a subject in need thereof, comprising administering to the subject an effective amount of a composition comprising the engineered polypeptide conjugates as described herein.

In another aspect, provided is a method of detecting, diagnosing, and/or monitoring a condition associated with a cancer-related protein (e.g., Trop-2, BRCA1, BRCA2, HER2, VEGF, CD20, CD25, EFGR, 5T4, CD22, etc.) in vivo or in vitro. Accordingly, in some embodiments, provided is a method of diagnosing cancer in a subject suspected of suffering from cancer, comprising a) contacting a sample of the subject with the engineered polypeptide conjugates as described herein under conditions that result in binding of the engineered polypeptide conjugates with a cancer-related protein, and b) determining binding of the engineered polypeptide conjugates to the cancer-related protein.

The agent moiety in the engineered polypeptide conjugates as described herein can be a detectable moiety such as an imaging agent and an enzyme-substrate label. The engineered polypeptide conjugates as described herein can also be used for in vivo diagnostic assays, such as in vivo imaging (e.g., PET or SPECT), or a staining reagent.

In some embodiments, the methods described herein further comprise a step of treating a subject with an additional form of therapy. In some embodiments, the additional form of therapy is an additional anti-cancer therapy including, but not limited to, chemotherapy, radiation, surgery, hormone therapy, and/or additional immunotherapy.

In some embodiments, the additional form of therapy comprises administering one or more therapeutic agent in addition to the engineered polypeptide conjugates as described herein. The therapeutic agents include, but are not limited to, an antibody-drug conjugate (e.g., brentuximab vedotin (ADCETRIS®) and ado-trastuzumab emtansine (KADCYLA®)), an antibody (e.g., an anti-VEGF antibody, an anti-HER2 antibody, anti-CD25 antibody, and/or an anti-CD20 antibody), an angiogenesis inhibitor, a cytotoxic agent (e.g., docetaxel, cisplatin, doxorubicin, mitomycin, tamoxifen, or fluorouracil), and an anti-inflammatory agent (e.g., prednisone, and progesterone).

Pharmaceutical Compositions

The present invention also provides a pharmaceutical composition comprising the engineered polypeptide conjugates as described herein in a pharmaceutically acceptable excipient or carrier. The engineered polypeptide conjugates can be administered alone or in combination with one or more other engineered polypeptide conjugates of the invention or in combination with one or more other drugs (or as any combination thereof). The pharmaceutical compositions, methods and uses of the invention thus also encompass embodiments of combinations (co-administration) with other active agents, as detailed below.

As used herein, the term "co-administration," "co-administered," or "in combination with" is intended to mean and does refer to the following: (i) simultaneous administration of a combination of an engineered polypeptide conjugate disclosed herein and therapeutic agent(s) to a patient in need of treatment, when such components are formulated together into a single dosage form which releases said components at substantially the same time to said patient; (ii) substantially simultaneous administration of such combination of an engineered polypeptide conjugate disclosed herein and therapeutic agent(s) to a patient in need of treatment, when such components are formulated apart from each other into separate dosage forms which are taken at substantially the same time by said patient, whereupon said components are released at substantially the same time to said patient; (iii) sequential administration of such combination of an engineered polypeptide conjugate disclosed herein and therapeutic agent(s) to a patient in need of treatment, when such components are formulated apart from each other into separate dosage forms which are taken at consecutive times by said patient with a significant time interval between each administration, whereupon said components are released at substantially different times to said patient; and (iv) sequential administration of such combination of an engineered polypeptide conjugate disclosed herein and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

Generally, the engineered polypeptide conjugates disclosed herein are suitable to be administered as a formulation in association with one or more pharmaceutically acceptable excipient(s). The term 'excipient' is used herein to describe any ingredient other than the compound(s) of the invention. The choice of excipient(s) to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In some embodiments, isotonic agents, including, but not limited to, sugars, polyalcohols (e.g., mannitol, sorbitol) or sodium chloride are included in the pharmaceutical composition. Additional examples of pharmaceutically acceptable substances include, but are not limited to, wetting agents or minor amounts of auxiliary substances such as wetting or emulsifying agents, preservatives or buffers, which enhance the shelf life or effectiveness of the antibody.

In some embodiments, the engineered polypeptide conjugates described herein can be deimmunized to reduce immunogenicity upon administration to a subject using known techniques such as those described, e.g., in PCT Publication WO98/52976 and WO00/34317.

Pharmaceutical compositions of the present invention and methods for their preparation are readily apparent to those skilled in the art. Such compositions and methods for their preparation may be found, for example, in Remington's Pharmaceutical Sciences, 22nd Edition (Mack Publishing Company, 2012). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. Any method for administering peptides, proteins or antibodies accepted in the art may suitably be employed for the engineered polypeptide conjugates disclosed herein.

The pharmaceutical compositions of the invention are typically suitable for parenteral administration. Parenteral administration of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. For example, parenteral administration includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. In some embodiments, parenteral administration is the intravenous or the subcutaneous route.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include controlled, delayed, sustained, pulsed, targeted and programmed release formulations. For example, in one aspect, sterile injectable solutions can be prepared by incorporating the engineered Fc-containing polypeptide, e.g., antibody-drug conjugate or bispecific antibody, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the agent moiety (e.g., small molecules such as cytotoxic agent) and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of an engineered polypeptide conjugate disclosed herein is typically in the range of about 0.01 mg to about 1200 mg per patient, depending, of course, on the mode of administration. For example, an intravenous monthly dose may require about 1 to about 1000 mg/patient. The total monthly dose may be administered in single or divided doses and may, at the physician's discretion, fall outside of the typical range given herein.

An exemplary, non-limiting range for a therapeutically or prophylactically effective amount of an engineered polypeptide conjugate, e.g., an Fc-containing polypeptide conjugate, Fab-containing polypeptide conjugate, antibody conjugate, or toxin polypeptide conjugate, disclosed herein is about 0.01 to about 1000 mg/patient/month. In certain embodiments, the engineered Fc-containing polypeptide conjugate may be administered at about 1 to about 200 or about 1 to about 150 mg/patient/month. In some embodiments, the patient is human.

Kits

The invention also provides kits (or articles of manufacture) for use in the treatment of the disorders described above. Kits of the invention include one or more containers comprising a purified engineered polypeptide conjugate and instructions for using the conjugate for treating a disease. For example, the instructions comprise a description of administration of the engineered polypeptide conjugate to treat a disease, such as cancer (e.g., colon, esophageal, gastric, head and neck, lung, ovarian, or pancreatic cancer). The kit may further comprise a description of selecting an individual suitable for treatment based on identifying whether that individual has the disease and the stage of the disease.

The instructions relating to the use of the engineered polypeptide conjugate generally include information as to dosage, dosing schedule, and route of administration for the intended treatment. The containers may be unit doses, bulk packages (e.g., multi-dose packages) or subunit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an engineered polypeptide as described herein. The container may further comprise a second pharmaceutically active agent.

Kits may optionally provide additional components such as buffers and interpretive information. Normally, the kit comprises a container and a label or package insert(s) on or associated with the container.

EXAMPLES

It is understood that the examples and embodiments described herein are for illustrative purposes only and that various modifications or changes in light thereof will be suggested to persons skilled in the art and are to be included within the spirit and purview of this application.

Example 1

Proteolysis of the C-Terminal Heavy Chain TG6 Tag During CHO Expression

Clipping of the last two amino acids (-GA) from an acyl donor glutamine-containing tag (e.g., TG6 tag (LLQGA (SEQ ID NO:1)) was observed when the TG6 tag was positioned at the C-terminus of an antibody's heavy chain (e.g., mAb1, which is an anti-Trop2 antibody as used in all of the examples described herein). Under tested expression conditions, 10-90% of the TG6 tag was found to be proteolyzed. This C-terminal clipping appears specific to CHO cells, as it was not observed during expression of Ab-TG6 in HEK293 cells. When the -GA was lost from the tag, no conjugation of a desired payload (e.g., drug or agent moiety) to the antibody was observed at the clipped TG6 tag (i.e., LLQ) at the C-terminus of the antibody.

A new set of the acyl donor glutamine-containing tags at the end of the C-terminus of an antibody (e.g., mAb1) was created to prevent the observed clipping. TG (transglutaminase) tags TG7-TG17 (SEQ ID NOS: 2-11; Table 1) were designed to contain proline to minimize the proteolysis. The newly designed tags were first expressed in HEK293 cells and tested for homogeneity and conjugatability by HIC (hydrophobic interaction chromatography) and mass spectrometry as described by Strop et al. *Chem Biol.*, 20(2): 161-7 (2013), hereby incorporated by reference herein in its entirety. In contrast to TG6, TG tags (e.g., TG11 and TG12) that contained proline at the C-terminus to the reactive glutamine showed no conjugation to the linker and the desired payload (e.g., AcLys-VC-PABC-0101 (AcLys-VC-PABC is acetyl-lysine-valine-citrulline-p-aminobenzyloxycarbonyl, and 0101 is 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide)). The remaining TG tags were conjugated to high efficiency. Some C-terminal heterogeneity was observed for TG7, TG8, and TG12-15.

TG tags TG9, TG10, and TG17, which appeared homogeneous in HEK293, were expressed in CHO cells to test whether C-terminal clipping would occur. The expression of TG10 (finished in -LLQGP (SEQ ID NO:5)) in CHO cells showed an 11% clipping of -GP. Remaining two tags (TG9 and TG17) did not show any C-terminal clipping under the same condition in which around ~33.6% clipping was observed in the TG6 tag. FIGS. 1A-1D. Accordingly, these results demonstrate that TG9 and TG17 tags prevent proteolysis at the C-terminus of an antibody's heavy chain when expressed in CHO cells.

TABLE 1

| Name | Sequence |
| --- | --- |
| TG6 | LLQGA (SEQ ID NO: 1) |
| TG7 | LLQGPGK (SEQ ID NO: 2) |
| TG8 | LLQGPG (SEQ ID NO: 3) |
| TG9 | LLQGPA (SEQ ID NO: 4) |
| TG10 | LLQGP (SEQ ID NO: 5) |
| TG11 | LLQP (SEQ ID NO: 6) |
| TG12 | LLQPGK (SEQ ID NO: 7) |
| TG14 | LLQGAPGK (SEQ ID NO: 8) |
| TG15 | LLQGAPG (SEQ ID NO: 9) |
| TG16 | LLQGAP (SEQ ID NO: 10) |
| TG17 | LLQGPP (SEQ ID NO: 11) |

Example 2

Proteolysis of the C-Terminal Light Chain LCQ04 Tag During CHO Expression

Clipping of the last two amino acids (-GA) from the LCQ04 tag (GGLLQGA (SEQ ID NO:12)) was also observed when the LCQ04 tag was positioned at the C-terminus of an antibody's light chain having K222R mutation (EU numbering scheme), although at much lesser degree than in the antibody's heavy chain. This C-terminal clipping appears specific to CHO cells, as it was not observed during HEK293 expression. Under tested expression conditions, about 5% of the LCQ04 tag was found to be proteolyzed.

Figure 2A:
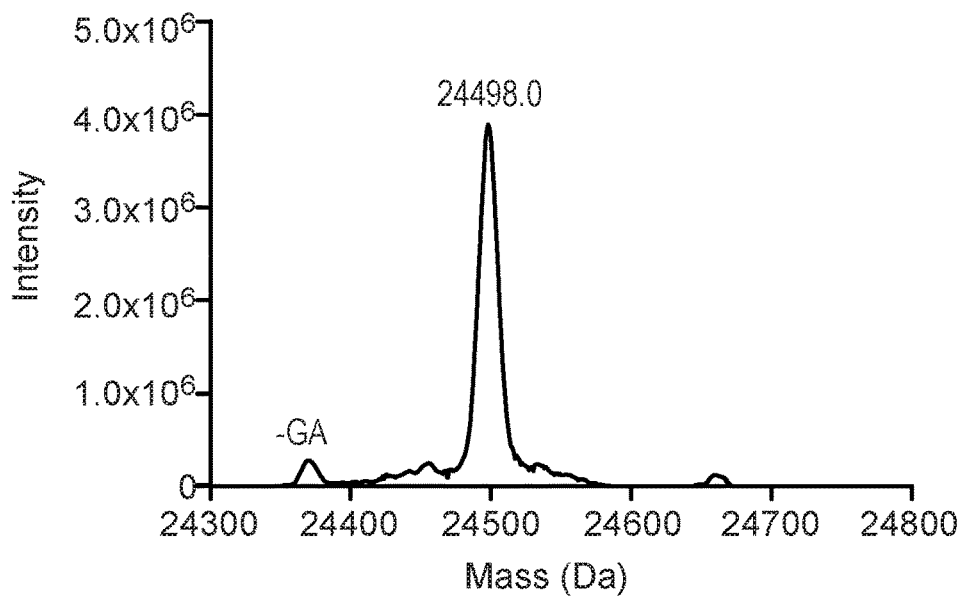
FIGS. 2A-2B show that the glutamine tag LCQ04 (SEQ ID NO:12) expressed in CHO cells was clipped from the C-terminus of an antibody light chain (2A), whereas no clipping was observed in the glutamine tag LCQ05 (SEQ ID NO:13) in Ab-LCQ05 (2B).
Figure 2B:
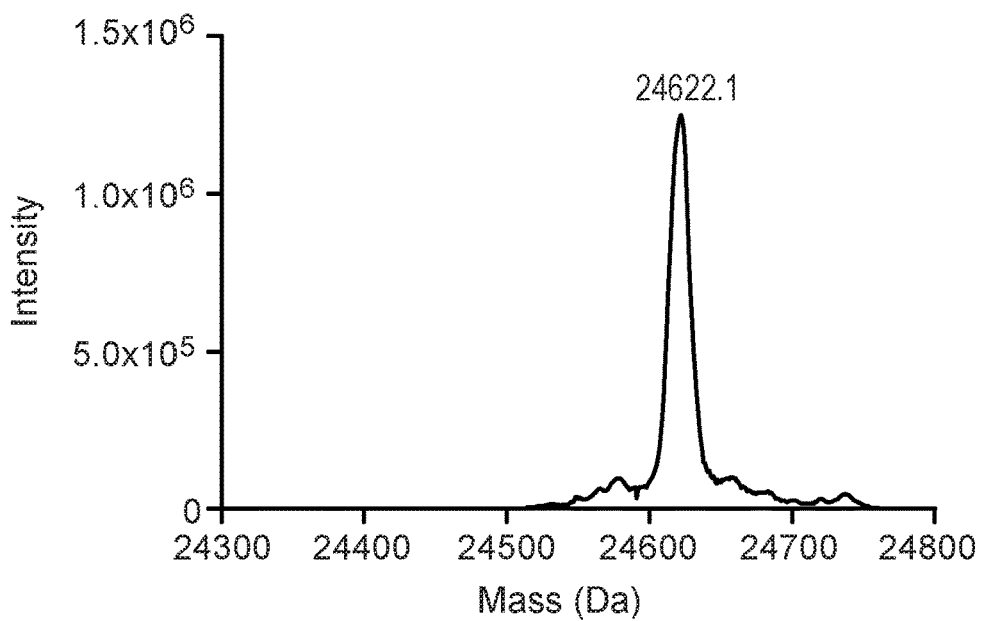

The LCQ05 tag (GGLLQGPP (SEQ ID NO:13)) was created having two prolines similar to the TG17 tag described above. The LCQ05 TG tag appeared homogeneous when expressed in both CHO and HEK293 cells and could be conjugated to the desired linker-payload (e.g., AcLys-VC-PABC-0101) at comparable levels as LCQ04. FIGS. 2A-2B. Accordingly, these results demonstrate that LCQ05 tag prevents proteolysis at the C-terminus of an antibody's light chain when expressed in CHO cells.

Example 3

Biophysical and Efficacy Comparison of TG6 and TG17 Tags

Figure 3A:
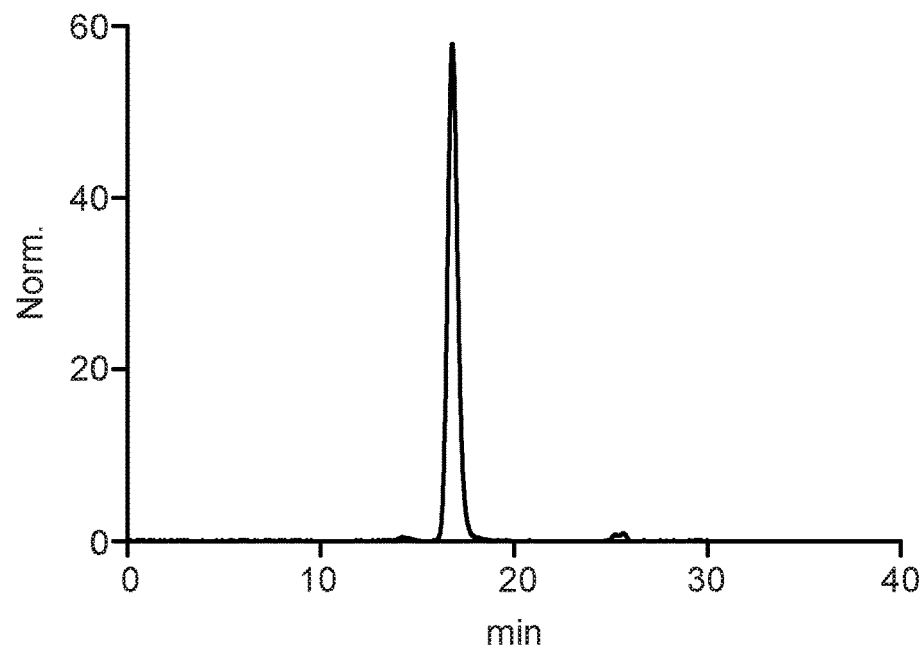
FIGS. 3A-3B show that similar low levels of aggregates were observed for the glutamine tags TG6 (SEQ ID NO:1) and TG17 (SEQ ID NO:11) in Ab-TG6-AcLys-VC-PABC-0101 (FIG. 3A) and Ab-TG17-AcLys-VC-PABC-0101 (FIG. 3B) using analytical size exclusion chromatography (SEC).
Figure 3B:
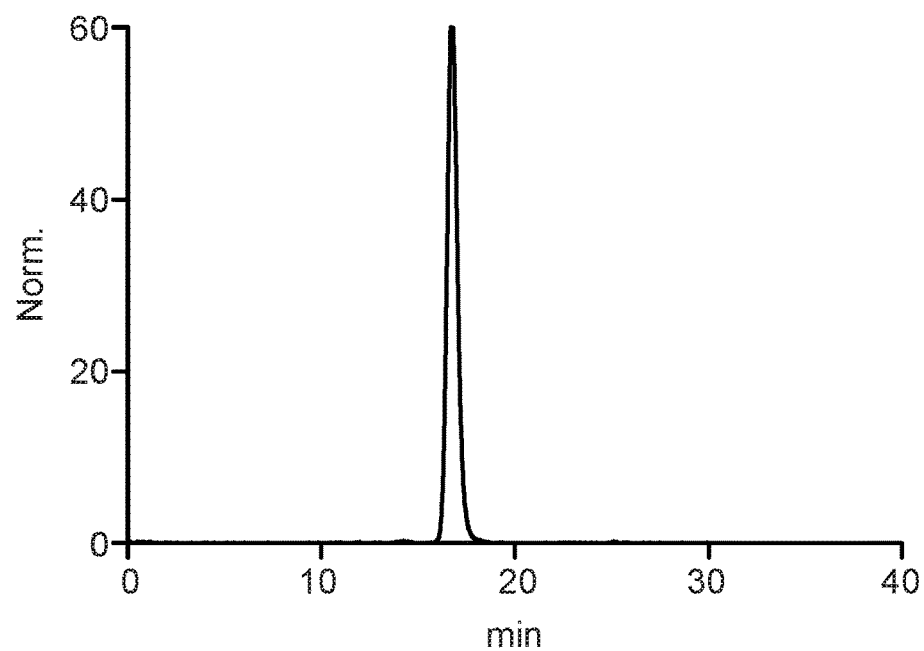
Figure 4A:
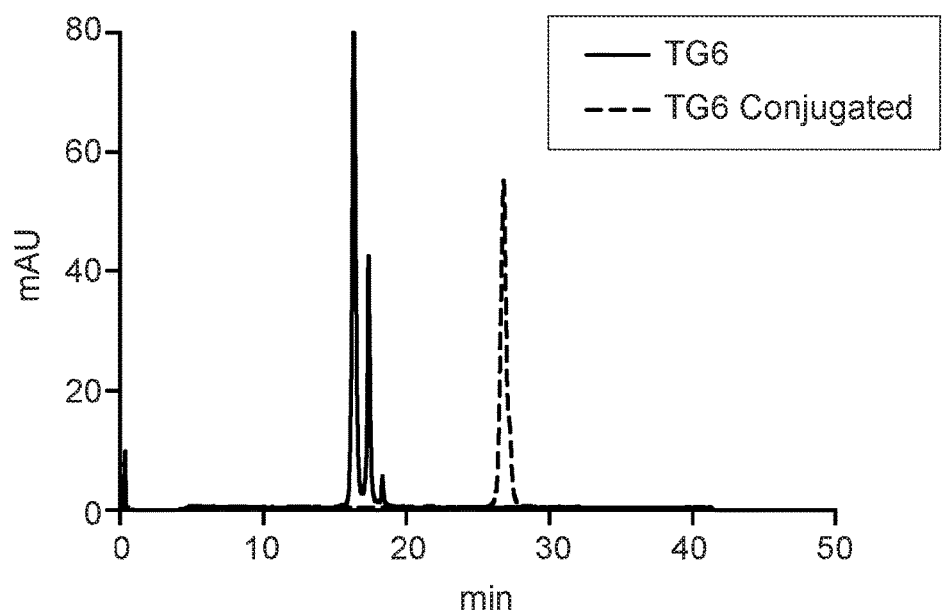
FIGS. 4A-4B show that similar Drug-Antibody-Ratio (DAR) was observed for the glutamine tags TG6 (SEQ ID NO:1) and TG17 (SEQ ID NO:11) in Ab-TG6 and Ab-TG6-AcLys-VC-PABC-0101 (FIG. 4A) and Ab-TG17 and Ab-TG17-AcLys-VC-PABC-0101 (FIG. 4B) using Hydrophobic Interaction Chromatography (HIC).
Figure 4B:
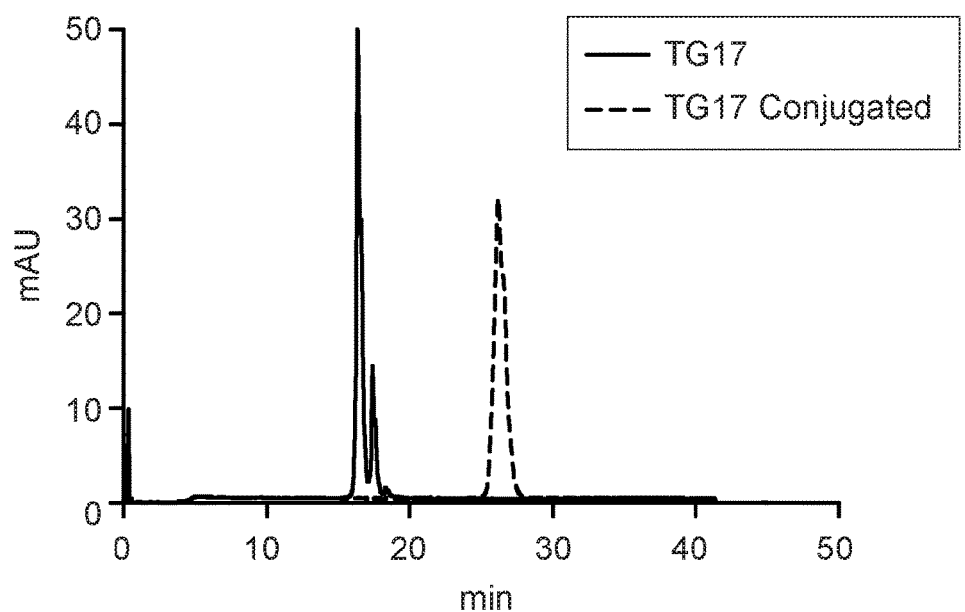
Figure 5A:
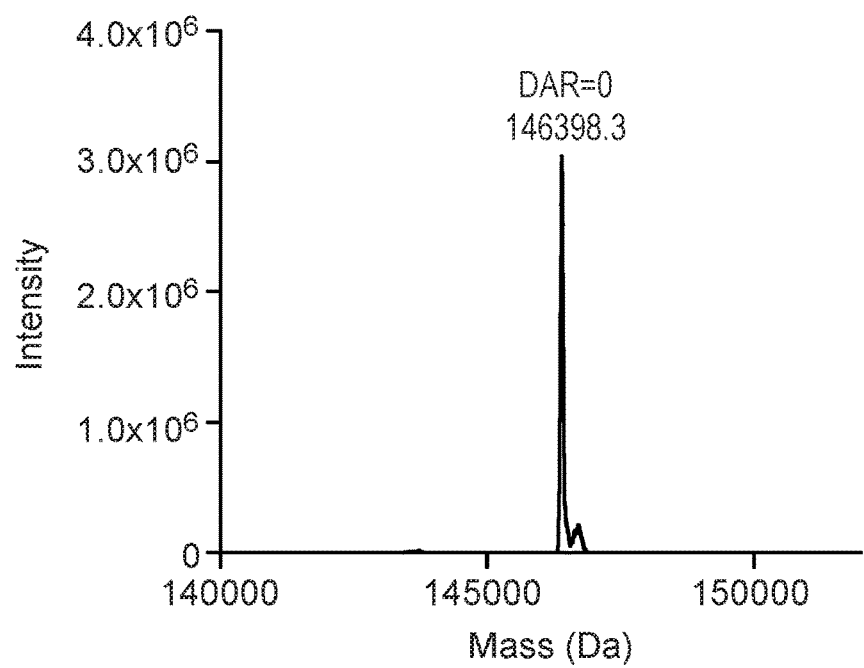
FIGS. 5A-5B show that similar Drug-Antibody-Ratio (DAR) was observed for the glutamine tags TG6 (SEQ ID NO:1) and TG17 (SEQ ID NO:11) in Ab-TG6 and Ab-TG17 (FIG. 5A) and Ab-TG6-AcLys-VC-PABC-0101 and Ab-TG17-AcLys-VC-PABC-0101 (FIG. 5B) using Mass Spectrometry (MS).
Figure 5A:
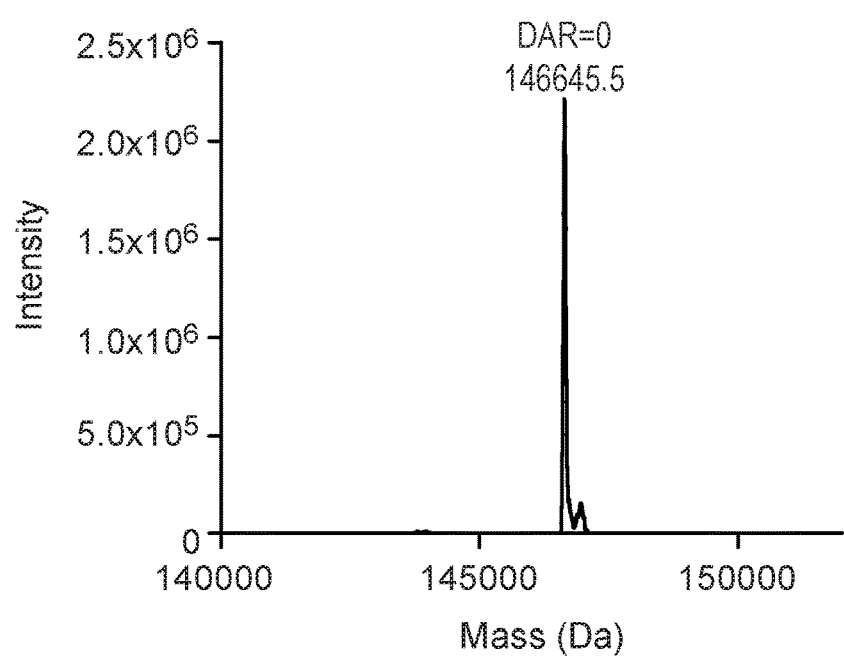
Figure 5B:
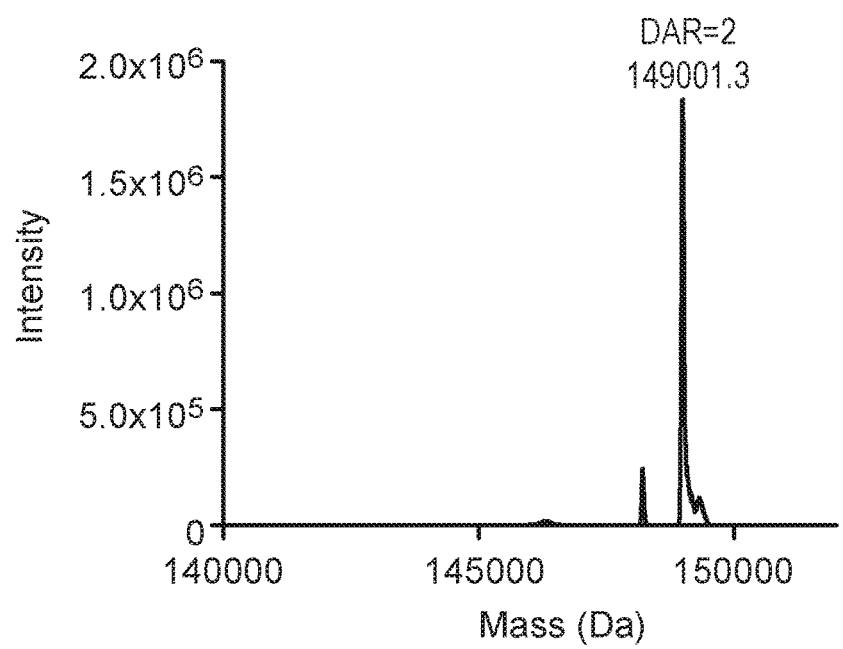
Figure 5B:
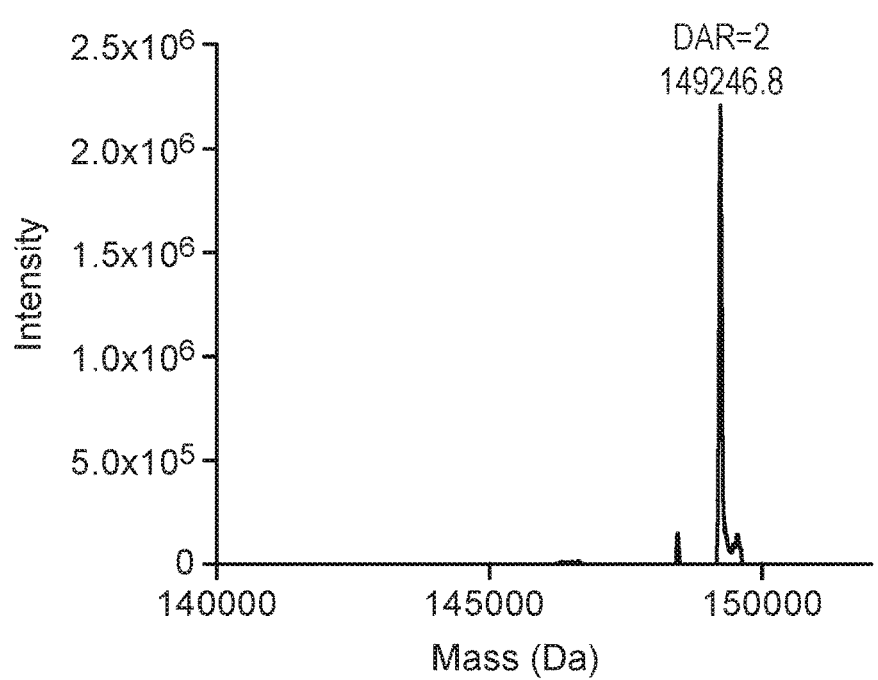

The new acyl donor glutamine-containing tags were validated by comparing the biophysical characteristics of the unconjugated and conjugated TG6 tag and TG17 tag. More specifically, analytical size exclusion chromatography (SEC) showed similar low level of aggregates, and the conjugation efficiency was comparable under the same conditions. FIGS. 3A-3B. In SEC, about 15 ug of samples (antibody-TG6 and antibody-TG17, or antibody-TG6-AcLys-VC-PABC-0101 and antibody-TG6-AcLys-VC-PABC-0101) were injected in a TSKGEL® G3000SW (Tosoh Bioscience LLC, King of Prussia, Pa.) size exclusion chromatography column on an Agilent HP 1100 HPLC (Santa Clara, Calif.) and run at 0.5 mL/min with the mobile phase (170 mM KPi; 210 mM KCl; 15% Isopropanol). The samples were also applied to the HIC (Hydrophobic Interaction Chromatography) column and showed similar DAR (drug antibody ratio) for the TG6 and TG17 tags as well as in mass spectrometry. FIGS. 4A-4B and 5A-5B. For HIC, 20 ug of antibody drug conjugate (e.g., antibody carrying TG6 or TG17 tag and conjugated to AcLys-VC-PABC-0101) in 0.75 M ammonium sulfate was loaded onto a TSKGEL® Butyl-NPR column (Tosoh Bioscience, King of Prussia, Pa.) on an Agilent HP 1100 HPLC (Santa Clara, Calif.). The mobile phase buffer A was 1.5 M ammonium sulfate and 50 mM potassium phosphate at pH=7.0; buffer B was 50 mM potassium phosphate and 20% Isopropanol at pH=7.0. The run was performed at 0.8 mL/min with a 35 minutes linear gradient 0-100% B. For Mass spectrometry (MS), prior to Liquid Chromatography-Mass Spectrometry (LC/MS) analysis, antibody-drug conjugates were deglycosylated with PNGase F (NEB, cat#P0704L) under non-denaturing conditions at 37° C. overnight. ADCs (500 ng) were loaded into a reverse phase column (Michrom-Bruker, Auburn, Calif.). LS/MS analysis was performed using Agilent 1100 series HPLC system coupled to an Orbitrap Velos Pro (Thermo Fisher Scientific, Waltham, Mass.) mass spectrometer. The resulting mass spectra were deconvoluted using ProMass software (Thermo Fisher Scientific). These results demonstrate that the new glutamine tags (e.g., TG17) have similar biophysical characteristics as the TG6 tag.

In Vitro Efficacy in BxPC3 and OVCAR3 Cell Lines

Figure 6A:
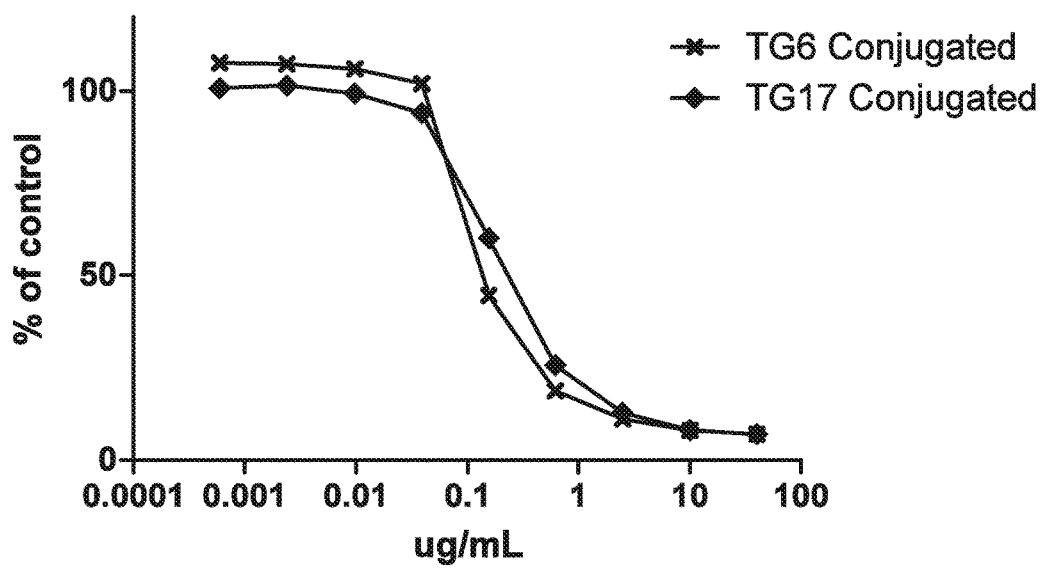
FIGS. 6A-6B show that antibody conjugates Ab-TG6-AcLys-VC-PABC-0101 and Antibody-TG17-AcLys-VC-PABC-0101 had the similar in vitro efficacy for cytotoxicity in BxPC3 cell line (FIG. 6A) and OVCAR3 cell line (FIG. 6B).
Figure 6B:
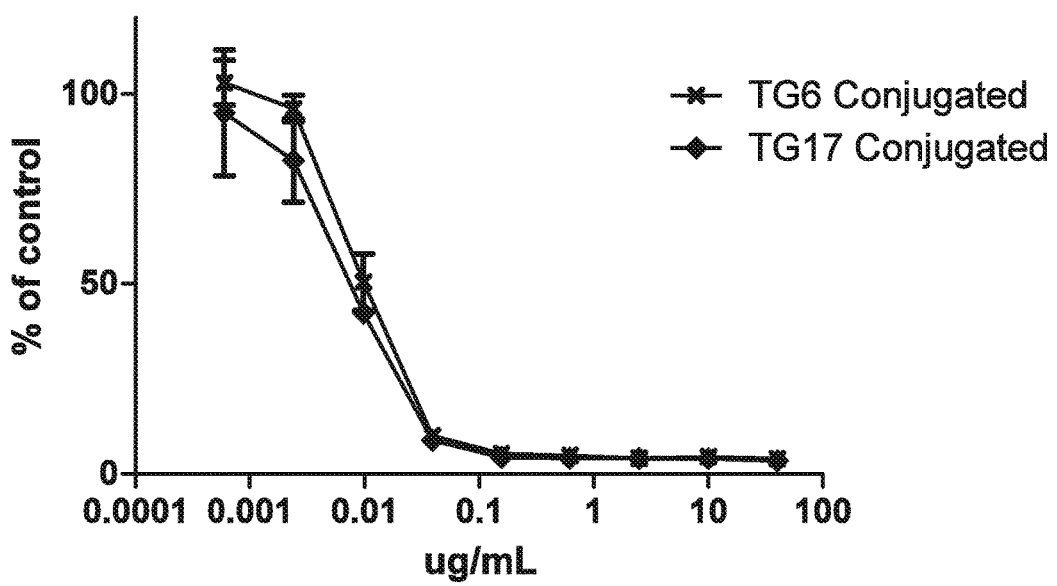

Both antibody conjugates (Antibody-TG6-AcLys-VC-PABC-0101 or Antibody-TG17-AcLys-VC-PABC-0101) were also tested for in vitro efficacy on BxPC3 and OVCAR3 cell lines for cytotoxicity, and the IC50 values obtained were comparable. See Table 2 and FIGS. 6A-6B. More specifically, BxPC3 and OVCAR3 cells at 2000 and 3000 cells/well, respectively, were diluted in 100 uL growth media (serum free DMEM, Cellgro Mediatech, Manassas, Va.). The next day, 25 uL of five times of ADCs (in serum free DMEM) were added. CelltiterGlo assays (Promega, Madison, Wis.) were performed 4 days after treatment. Cells were added with 1:1 diluted reagent after media removal. The plates were read on MSpectraMax M5 plate reader (Molecular Devices, Downingtown, Pa.).

TABLE 2

| Conjugate | DAR | BxPC3 | | OVCAR3 | |
|---|---|---|---|---|---|
| | | Ab-IC50 (ug/mL) | Ab-IC50 (nM) | Ab-IC50 (ug/mL) | Ab-IC50 (nM) |
| Ab-TG6-AcLys-VC-PABC-0101 | 2.00 | 0.164 | 1.093 | 0.010 | 0.068 |
| Ab-TG17-AcLys-VC-PABC-0101 | 2.00 | 0.257 | 1.715 | 0.008 | 0.051 |

Log(inhibitor) vs normalized response - various slopes

These results demonstrate that Antibody-TG6-AcLys-VC-PABC-0101 and Antibody-TG17-AcLys-VC-PABC-0101 have similar in vitro efficacy in BxPC3 and OVCAR3 cell lines for cytotoxicity.

In Vivo Efficacy in Pan0123 Xenograft Model

Figure 7A:
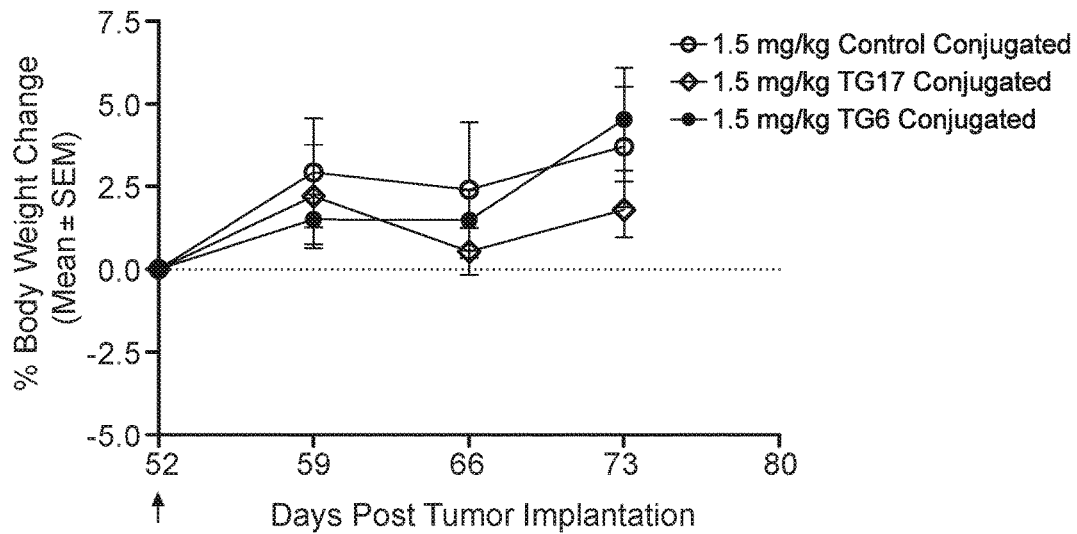
FIGS. 7A-7B show that antibody conjugate (Ab-TG17-AcLys-PABC-0101) having the glutamine tag TG17 (SEQ ID NO: 11) had similar activity in in vivo tumor models (% body weight change in FIG. 7A; and tumor volume in FIG. 7B) in comparison to the antibody conjugate (Ab-TG6-AcLys-PABC-0101) having the glutamine tag TG6 (SEQ ID NO: 1).
Figure 7B:
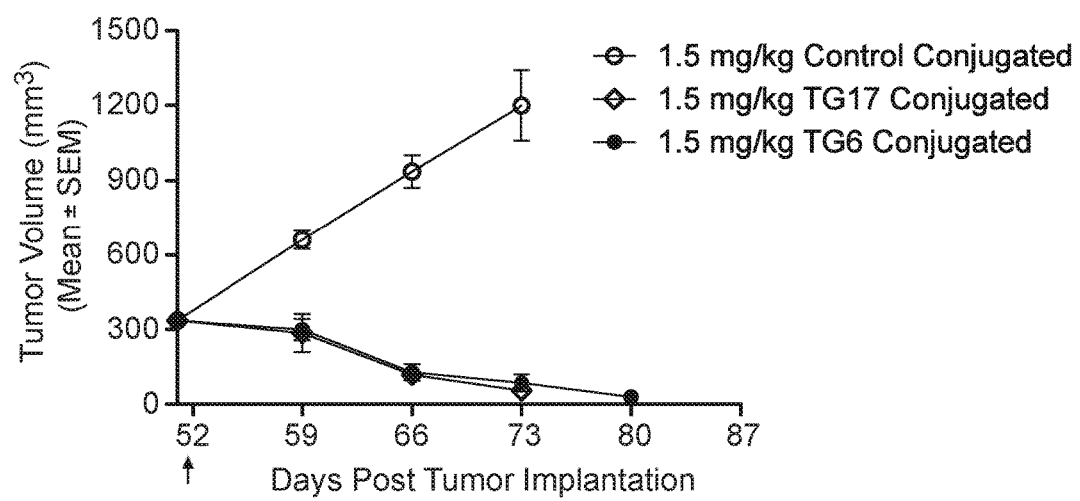

In vivo efficacy studies of the antibody conjugates were performed with antibody-expressing Pancreatic Pan0123 PDX xenograft tumors. 2×2×2 mm$^3$ tumor fragments were implanted subcutaneously into 5-8 weeks old SCID (Severe Combined Immunodeficient) mice until the tumor sizes reached at least 300 mm$^3$. Control antibody conjugate and Trop-2 targeting antibody conjugates (Ab-TG6-AcLys-VC-PABC-0101 and Ab-TG17-AcLys-VC-PABC-0101) were given to the SCID mice at 1.5 mg/kg as single dose bolus injection through tail vein. All experimental animals were monitored for body weight changes weekly. Tumor volume was measured once a week by a Caliper device and calculated with the following formula: Tumor volume=(length× width)/2. The tumor volume and body weight were monitored up to 80 days after tumor implantation. These results demonstrate that antibody conjugate having the TG17 tag had similar activity in comparison to the antibody conjugate having the TG6 tag. FIGS. 7A-7B.

Pharmacokinetics

The PK (pharmacokinetics) was further tested by injecting female rats with a single dose of AB-TG6-AcLys-VC-PABC-0101 or AB-TG17-AcLys-VC-PABC-0101 (174-2) at 5 mg/kg.

The animals were 12 adult Sprague Dawley female rats at approximately 3 months of age. (Harlan, Livermore, Calif.). For PK and plasma stability experiments, compounds were dosed intravenously through the lateral tail vein, and samples were withdrawn from the contralateral tail vein at appropriate time points, except for a terminal bleed which was obtained via cardiac puncture on anesthetized adult rats. Samples from one group of rats were processed for serum while samples from a separate group of rats were processed for plasma. Both sample types were stored frozen at −80° C. until analysis.

Figure 8:
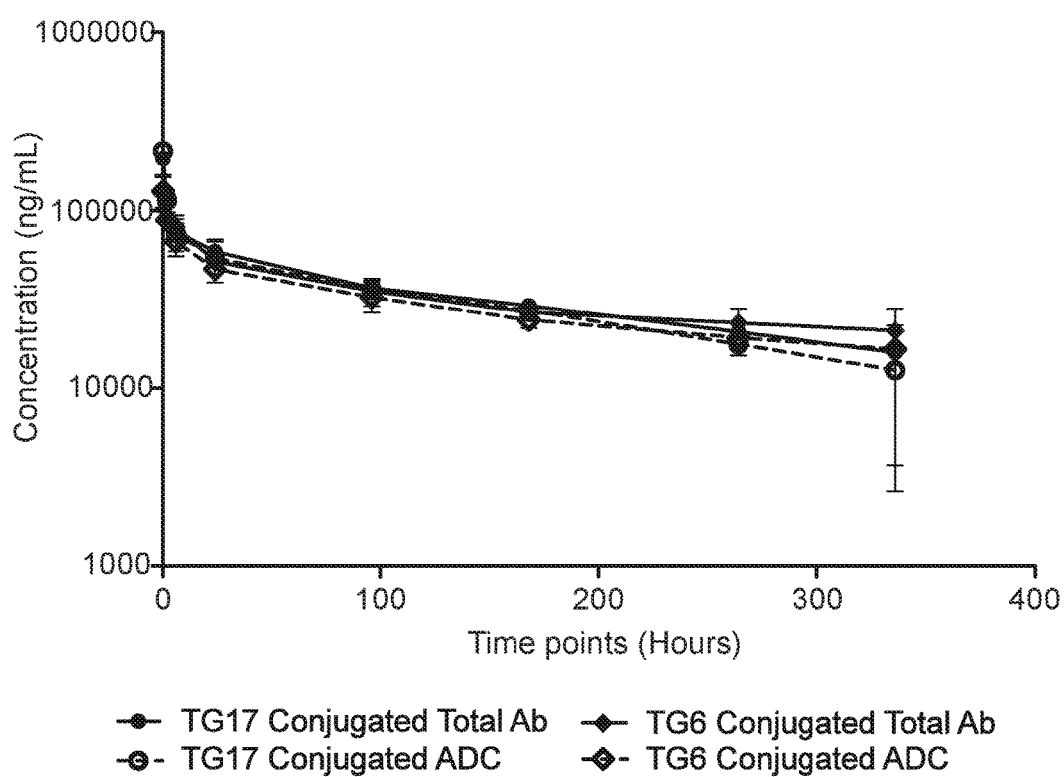
FIG. 8 shows the pharmacokinetics for antibody conjugates Ab-TG6-AcLys-VC-PABC-0101, Antibody-TG17-AcLys-VC-PABC-0101, Ab-TG6, and Ab-TG17.

Serum was collected at 8 time points up to 14 days with 3 rats per group. ELISA (Enzyme-Linked Immunosorbent Assay) was performed to measure total antibody and antibody conjugate in plasma as described by Strop et al. *Chem Biol.* 20(2):161-167 (2013). The results were similar for TG6 and TG17. FIG. 8.

Example 4

Q295N Mutant in the Heavy Chain of the mAb Eliminates Unwanted Conjugation Due to Trace Amounts of Aglycosylated Antibodies Expressed During mAb Expression In addition to conjugation of the antibody and the desired payload at an engineered site, a small amount of aglycosylated antibody present in starting material led to antibody-drug conjugation at position Q295, resulting in approximately 1.3% of off-target conjugation. Such off-target conjugation can be eliminated by the Q295N mutant (EU numbering scheme), which in turn results in highly homogenous antibody-drug conjugates that are better than 99.8% site-specific.

Figure 9A:
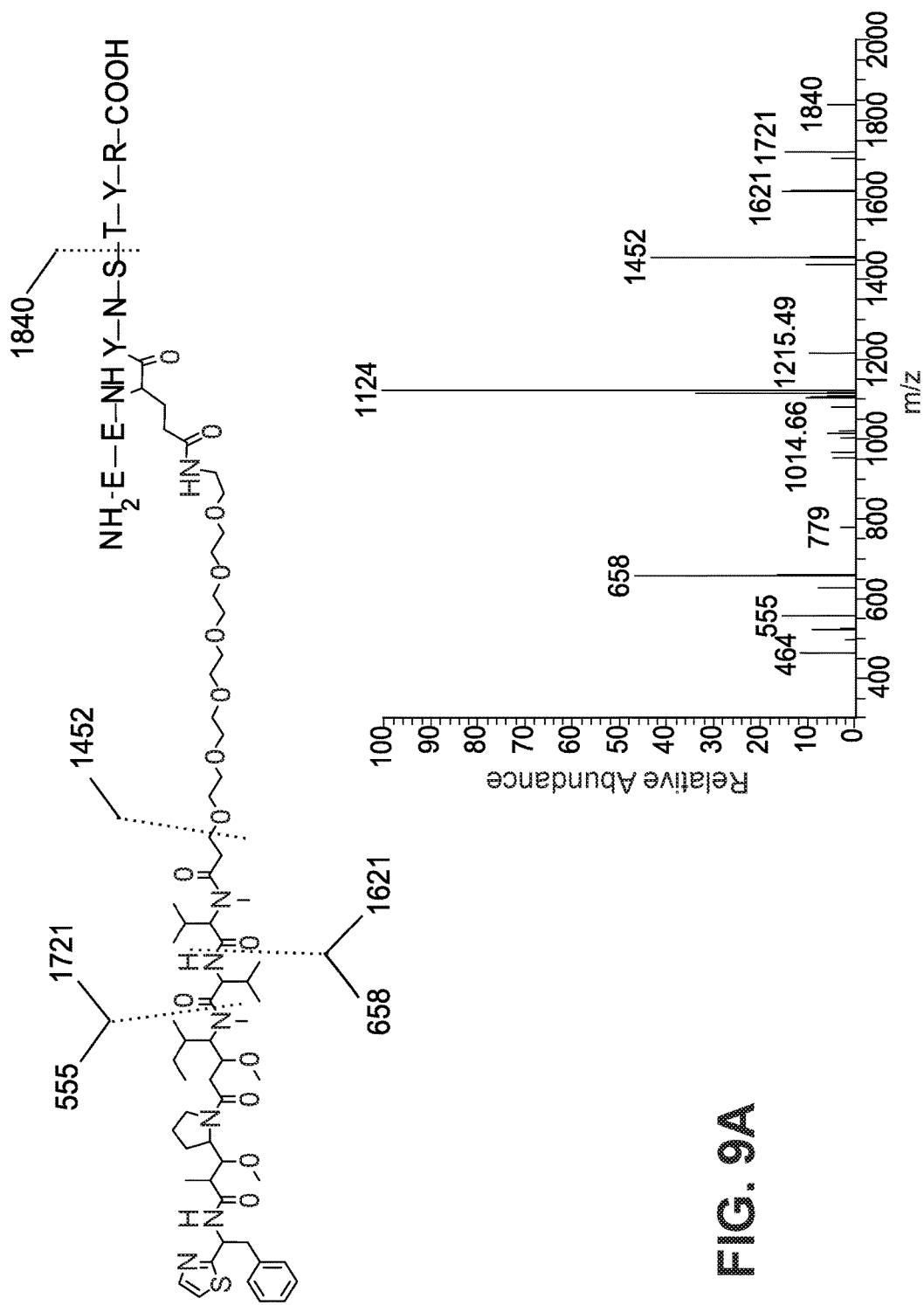
FIG. 9A shows that transglutaminase can recognize Q295 in aglycosylated IgGs, and conjugation can be achieved at this site (conjugation of Amino-PEG6-MMAD to a tryptic peptide (SEQ ID NO:15)).

More specifically, transglutaminase can recognize Q295 in aglycosylated IgGs, and conjugation can be achieved at this site. See MS/MS confirmation of conjugation of AmPEG6-MMAD to tryptic peptide EEQ*YNSTYR (SEQ ID NO:15) in FIG. 9A. When antibodies are expressed in the CHO or HEK293 expression system, most of the produced proteins are gycoyslated at position N297. The presence of glycans at position N297 prevents conjugation to Q295. However, there is typically a small fraction of aglycosylated antibodies that are also produced. It is this contaminating aglycosylated antibody fraction, which is suitable for conjugation at position Q295.

Figure 9B:
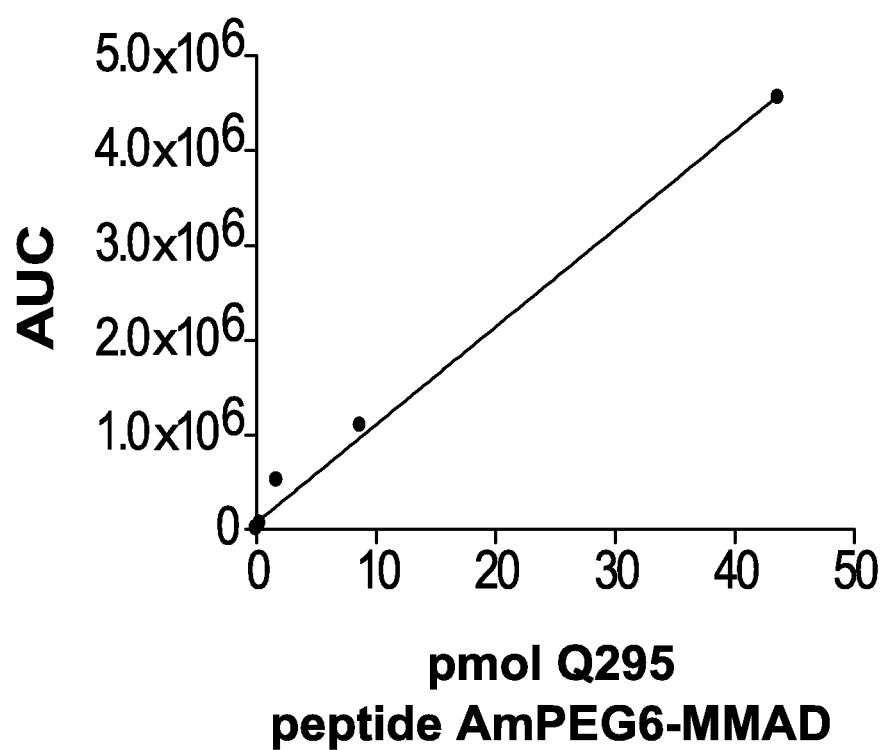
FIG. 9B shows that 1.3% of the total injected Q295 peptide was conjugated with amino-PEG6-MMAD in the heavy chain of the antibody, assuming 100% digestion efficiency.

To estimate the amount of this off-target conjugation to the Q295 site, conjugated EEQ*YNSTYR (SEQ ID NO:15) standard peptide was spiked into a fixed amount (2.5 µg) of unconjugated tryptic digests of mAb1 HC (heavy chain), and a standard curve for quantification was generated. Using the precursor ion extracted chromatogram, it was estimated that 1.3% of the total injected Q295 peptide was conjugated with AmPEG6-MMAD (amino-polyethylene glycol-6 propionyl monomethyl auristatin D) in the mAb1 HC molecule assuming 100% digestion efficiency. FIG. 9B. A single point mutant Q295N was created to abolish the undesired conjugation. The peptide mass fingerprint of the Q295N mutant revealed only conjugation at the designed glutamine tag site for both the mAb1 light chain and heavy chain molecules with no additional identified sites.

Although the disclosed teachings have been described with reference to various applications, methods, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. An engineered antibody conjugate comprising the formula: polypeptide-T-A, wherein the polypeptide comprises a full length antibody heavy chain and an antibody light chain, wherein T is an acyl donor glutamine-containing tag engineered at a specific site, wherein A is an amine donor agent, wherein the amine donor agent is site-specifically conjugated to the acyl donor glutamine-containing tag at a carboxyl terminus, and/or an amino terminus of the antibody heavy chain and/or the antibody light chain, and wherein the acyl donor glutamine-containing tag consists of the amino acid sequence GGLLQGPP (SEQ ID NO:13), wherein the antibody binds to Trop-2.

2. The engineered antibody conjugate of claim 1, wherein the acyl donor glutamine-containing tag is not spatially adjacent to a reactive Lys in the antibody heavy chain and/or the antibody light chain.

3. The engineered antibody conjugate of claim 2, wherein the antibody comprises an amino acid modification at the last amino acid position in the carboxyl terminus of the antibody heavy chain and/or the antibody light chain relative to a wild-type antibody at the same position.

4. The engineered antibody conjugate of claim 1, wherein the acyl donor glutamine-containing tag is located at the carboxyl terminus of the antibody heavy chain, the antibody light chain, or both the antibody heavy chain and the light chain.

5. The engineered antibody conjugate of claim 1, wherein the antibody is a monoclonal antibody, a polyclonal antibody, a human antibody, a humanized antibody, a chimeric antibody, a bispecific antibody, a minibody, a diabody, or an antigen-binding antibody fragment.

6. The engineered antibody conjugate of claim 5, wherein the antibody is an IgG.

7. The engineered antibody conjugate of claim 6, wherein the amine donor agent comprises the formula: X-Y-Z, wherein X is an amine donor unit; Y is a linker; and Z is an agent moiety.

8. The engineered antibody conjugate of claim 7, wherein the amine donor unit-linker (X-Y) is selected from the group consisting of Ac-Lys-Gly, aminocaproic acid, Ac-Lys-β-Ala, amino-PEG2-C2, amino-PEG3-C2, amino-PEG6-C2, Ac-Lys-Val-Cit-PABC, aminocaproyl-Val-Cit-PABC, [(3R,5R)-1-{3 -[2-(2-aminoethoxy)ethoxy]propanoyl}piperidine-3,5-diyl]bis-Val-Cit-PABC, [(3S,5S)-1-{3-[2-(2-aminoethoxy)ethoxy]propanoyl}]piperidine-3,5-diyl]bis-Val-Cit-PABC, putrescine, 2-aminoethoxy-PEG6, and Ac-Lys-putrescine.

9. The engineered antibody conjugate of claim 7, wherein the agent moiety is a cytotoxic agent.

10. The engineered antibody conjugate of claim 9, wherein the cytotoxic agent is selected from the group consisting of anthracycline, an auristatin, a camptothecin, a combretastatin, a dolastatin, a duocarmycin, an enediyne, a geldanamycin, an indolino-benzodiazepine dimer, a maytansine, a puromycin, a pyrrolobenzodiazepine dimer, a taxane, a vinca alkaloid, a tubulysin, a hemiasterlin, a spliceostatin, a pladienolide, and stereoisomers, and isosteres thereof.

11. The engineered antibody conjugate of claim 9, wherein the cytotoxic agent is MMAD (Monomethyl Auristatin D) or 0101 (2-methylalanyl-N-[(3R, 4S, 5S)-3-methoxy-1-{(2S)-2-[(1R, 2R)-1-methoxy-2-methyl-3-oxo-3-{[(1S)-2-phenyl-1-(1,3-thiazol-2-ly)ethyl]amino}propyl]pyrrolidin-1-yl}-5-methyl-1-oxoheptan-4-yl]-N-methyl-L-valinamide).

12. The engineered antibody conjugate claim 7, wherein the amine donor agent is selected from the group consisting of Alexa 488 cadaverine, 5-FITC cadaverine, Alexa 647 cadaverine, Alexa 350 cadaverine, 5-TAMRA cadaverine, 5-FAM cadaverine, SR101 cadaverine, 5,6-TAMRA cadaverine, 5-FAM lysine, Ac-LysGly-MMAD, am ino-PEG3-C2-MMAD, amino-PEG6-C2-MMAD, amino-PEG3-C2-amino-nonanoyl-MMAD, aminocaproyl-Val-Cit-PABC-MMAD, am ino-PEG-C2-Val-Cit-PABC-MMAD, Ac-Lys-Val-Cit-PABC-MMAD, aminocaproyl-MMAD, Ac-Lys-β-Ala-MMAD, amino-PEG2-C2-MMAE, aminocaproyl-MMAE, amino-PEG3-C2-MMAE, aminocaproyl-MMAF, aminocaproyl-Val-Cit-PABC-MMAE, amino-PEG-6-C2-Val-Cit-PABC-MMAE, Ac-Lys-Val-Cit-PABC-MMAE, aminocaproyl-Val-Cit-PABC-MMAF, amino-PEG-6-C2-Val-Cit-PABC-MMAF, Ac-Lys-Val-Cit-PABC-MMAF, Ac-Lys-Val-Cit-PABC-0101, putrescinyl-geldanamycin, Ac-Lys-putrescinyl-geldanamycin, aminocaproyl-3377, amino-PEG6-C2-3377, aminocaproyl-0131, amino-PEG6-C2-0131, aminocaproyl-0121, amino-PEG6-C2-0121, [(3R, 5R) -1-{3-[2-(2-aminoethoxy)ethoxy]propanoyl}piperidine-3, 5-diyl]bis-Val-Cit-PABC-MMAD, [(3R,5R)-1-{3-[2-(2-aminoethoxy)ethoxy]propanoyl}piperidine-3,5-diyl]bis-Val-Cit-PABC-MMAE, and 2-aminoethoxy-PEG6-NODAGA.

13. The engineered antibody conjugate of claim 7, wherein the amine donor unit-linker (X-Y) is a branched unit and the agent moiety comprises at least about 2 agent moieties.

14. The engineered antibody conjugate of claim 1, comprising an amino acid substitution from glutamine to asparagine at position 295 (Q295N; EU numbering scheme).

15. A pharmaceutical composition comprising the engineered antibody conjugate of claim 9, and a pharmaceutically acceptable excipient.

16. A method of treating a cancer in a subject in need thereof, comprising administering to the subject an effective amount of the pharmaceutical composition of claim 15.

17. A method of inhibiting tumor growth or progression in a subject in need thereof, comprising administering to the subject an effective amount of the pharmaceutical composition of claim 15.

* * * * *

```
                        SEQUENCE LISTING

<160> NUMBER OF SEQ ID NOS: 41

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Leu Leu Gln Gly Ala
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Leu Leu Gln Gly Pro Gly Lys
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Leu Leu Gln Gly Pro Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Leu Leu Gln Gly Pro Ala
1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Leu Leu Gln Gly Pro
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic Construct

<400> SEQUENCE: 6

Leu Leu Gln Pro
1

<210> SEQ ID NO 7
<211> LENGTH: 6
<212> TYPE: PRT
<213> ORGANISM: Artificial Sequences
<220> FEATURE:
<223> OTHER INFORMATION: Synthetic Construct

<400> SEQUENCE: 7

Leu Leu Gln Pro Gly Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Leu Leu Gln Gly Ala Pro Gly Lys
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Leu Leu Gln Gly Ala Pro Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

Leu Leu Gln Gly Ala Pro
1               5
```

```
<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

Leu Leu Gln Gly Pro Pro
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct

<400> SEQUENCE: 12

Gly Gly Leu Leu Gln Gly Ala
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct

<400> SEQUENCE: 13

Gly Gly Leu Leu Gln Gly Pro Pro
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: A or P

<400> SEQUENCE: 14

Leu Leu Gln Gly Pro Xaa
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

Glu Glu Gln Tyr Asn Ser Thr Tyr Arg
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16

Leu Leu Gln Gly Gly
```

```
1               5

<210> SEQ ID NO 17
<211> LENGTH: 4
<212> TYPE: PRT
<213> ORGANISM: Artificial Sequence
<220> FEATURE:
<223> OTHER INFORMATION: Synthetic Construct

<400> SEQUENCE: 17

Leu Leu Gln Gly
1

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct

<400> SEQUENCE: 18

Leu Ser Leu Ser Gln Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Gly Gly Gly Leu Leu Gln Gly Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Construct

<400> SEQUENCE: 20

Gly Leu Leu Gln Gly
1               5

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Gly Ser Pro Leu Ala Gln Ser His Gly Gly
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct

<400> SEQUENCE: 22

Gly Leu Leu Gln Gly Gly Gly
1               5
```

<210> SEQ ID NO 23
<211> LENGTH: 6
<212> TYPE: PRT
<213> ORGANISM: Artificial Sequence
<220> FEATURE:
<223> OTHER INFORMATION: Synthetic Construct

<400> SEQUENCE: 23

Gly Leu Leu Gln Gly Gly
1               5

<210> SEQ ID NO 24
<211> LENGTH: 4
<212> TYPE: PRT
<213> ORGANISM: Artificial Sequence
<220> FEATURE:
<223> OTHER INFORMATION: Synthetic Construct

<400> SEQUENCE: 24

Gly Leu Leu Gln
1

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

Leu Leu Gln Leu Leu Gln Gly Ala
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct

<400> SEQUENCE: 26

Leu Leu Gln Gly Ala
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic Construct

<400> SEQUENCE: 27

Leu Leu Gln Tyr Gln Gly Ala
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Construct

<400> SEQUENCE: 28

Leu Leu Gln Gly Ser Gly
1               5

```
<210> SEQ ID NO 29
<211> LENGTH: 6
<212> TYPE: PRT
<213> ORGANISM: Artificial Sequence
<220> FEATURE:
<223> OTHER INFORMATION: Synthetic Construct

<400> SEQUENCE: 29

Leu Leu Gln Tyr Gln Gly
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Leu Leu Gln Leu Leu Gln Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Construct

<400> SEQUENCE: 31

Ser Leu Leu Gln Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Construct

<400> SEQUENCE: 32

Leu Leu Gln Leu Gln
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic Construct

<400> SEQUENCE: 33

Leu Leu Gln Leu Leu Gln
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Construct

<400> SEQUENCE: 34

Leu Leu Gln Gly Arg
1               5
```

-continued

```
<210> SEQ ID NO 35
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa = Leu, Ala, Gly, Ser, Val, Phe, Tyr, His,
      Arg, Asn, Glu, Asp, Cys, Gln, Ile, Met, Pro, Thr, Lys, or Trp
<220> FEATURE:
<221> NAME/KEY: MISC_FEATURE
<222> LOCATION: (4)..(4)
<223> OTHER INFORMATION: Xaa = Leu, Ala, Gly, Ser, Val, Phe, Tyr, His,
      Arg, Asn, Glu, Asp, Cys, Gln, Ile, Met, Pro, Thr, Lys, or Trp

<400> SEQUENCE: 35

Xaa Xaa Gln Xaa
1

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct

<400> SEQUENCE: 36

Leu Gly Gly Gln Gly Gly Gly
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Gly Gly Gly Gln Gly Gly Leu
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa = Gly, Ala, Ser, Leu, Val, Phe, Tyr, Arg,
      Asn, or Glu

<400> SEQUENCE: 38

Gly Xaa Gly Gln Gly Gly Gly
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa = Gly, Ala, Ser, Leu, Val, Phe, Tyr, Arg,
      Asn, or Glu
```

```
<400> SEQUENCE: 39

Gly Gly Xaa Gln Gly Gly Gly
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa = Gly, Ala, Ser, Leu, Val, Phe, Tyr, Arg,
      Asn, or Glu

<400> SEQUENCE: 40

Gly Gly Gly Gln Xaa Gly Gly
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa = Gly, Ala, Ser, Leu, Val, Phe, Tyr, Arg,
      Asn, or Glu

<400> SEQUENCE: 41

Gly Gly Gly Gln Gly Xaa Gly
1               5
```